(12) United States Patent
Hekimi et al.

(10) Patent No.: US 7,132,274 B2
(45) Date of Patent: Nov. 7, 2006

(54) METHOD FOR IDENTIFYING MODULATORS OF CLK-1 AND UBIF ACTIVITY

(75) Inventors: Siegfried Hekimi, Montreal (CA); Abdelmadjid K. Hihi, Montreal (CA); Guy Nadeau, Montreal (CA)

(73) Assignee: McGill University, Montreal (CA)

( * ) Notice: Subject to any disclaimer, the term of this patent is extended or adjusted under 35 U.S.C. 154(b) by 116 days.

(21) Appl. No.: 10/841,316

(22) Filed: May 7, 2004

(65) Prior Publication Data

US 2004/0265989 A1 Dec. 30, 2004

Related U.S. Application Data

(60) Provisional application No. 60/468,707, filed on May 8, 2003.

(51) Int. Cl.
*C12N 1/20* (2006.01)
*C07H 21/02* (2006.01)
*C07K 14/00* (2006.01)

(52) U.S. Cl. .................. 435/252.3; 536/23.1; 530/350

(58) Field of Classification Search ............. 435/252.3; 536/23.1; 530/350
See application file for complete search history.

(56) References Cited

FOREIGN PATENT DOCUMENTS

WO  WO 02/077183  10/2002
WO  WO 03/014383   2/2003

OTHER PUBLICATIONS

Barnham et al., 2004, "Neurodegenerative diseases and oxidative stress," Nat. Rev. Drug Discov. 3(3):205-214.
Berthold et al. 2003, "Screening for functional expression and overexpression of a family of diiron-containing interfacial membrane proteins using the univector recombination system," Protein Sci. 12(1):124-134.
Betarbet et al. 2002, "Animal models of Parkinson's disease," Bioessays 24(4):308-318.
Collis and Grigg 1989 "An *Escherichia coli* mutant resistant to phleomycin, bleomycin, and heat inactivation is defective in ubiquinone synthesis," J. Bacteriol. 171(9):4792-4798.
Dallner and Sindelar, 2000 "Regulation of ubiquinone metabolism," Free Radic. Biol. Med. 29(3-4):285-294.
Desvergne, 2004, "Be fit or be sick: peroxisome proliferator-activated receptors are down the road," Mol. Endocrinol. 18(6):1321-1332.
Ewbank et al., 1997, "Structural and functional conservation of the *Caenorhabditis elegans* timing gene clk-1," Science 275(5302):980-983.
Hihi et al., 2003, "Sensitivity of *Caenorhabditis elegans* clk-1 mutants to ubiquinone side-chain length reveals multiple ubiquinone-dependent processes," J. Biol. Chem. 278(42):41013-41018.
Hihi et al., 2002, "Ubiquinone is necessary for *Caenorhabditis elegans* development at mitochondrial and non-mitochondrial sites," J. Biol. Chem. 277(3):2202-2206.
Jiang et al.. 2001, "Mouse CLK-1 is imported into mitochondria by an unusual process that requires a leader sequence but no membrane potential," J. Biol. Chem. 276(31):29218-29225.
Kwon et al., 2000, "Ubiquinone (coenzyme Q) biosynthesis in *Escherichia coli*: identification of the ubiF gene," FEMS Microbiol Lett. 186(2):157-161.
Li 2002, "Reactive species mechanisms of cellular hypoxia-reoxygenation injury," Am. J. Physiol. Cell Physiol. 282(2):C227-241.
Lusis, 2000, "Atherosclerosis," Nature 407(6801):233-241.
Miyadera et al., 2001, "Altered quinone biosynthesis in the long-lived clk-1 mutants of *Caenorhabditis elegans*," J. Biol. Chem. 276(11):7713-7716.
Rustin et al. 1999, "Effect of idebenone on cardiomyopathy in Friedreich's ataxia: a preliminary study," Lancet 354(9177):477-479.
Shults et al. 2002, "Effects of coenzyme Q10 in early Parkinson disease: evidence of slowing of the functional decline," Arch. Neurol. 59(10):1541-1550.
Steinberg 2002, "Atherogenesis in perspective: hypercholesterolemia and inflammation as partners in crime," Nat. Med. 8(11):1211-1217.
Stenmark et al., 2001, "A new member of the family of di-iron carboxylate proteins. Coq7 (clk-1), a membrane-bound hydroxylase involved in ubiquinone biosynthesis," J. Biol. Chem. 276(36):33297-33300.
Urakawa et al. 2003, "Oxidative stress is associated with adiposity and insulin resistance in men," J. Clin. Endocrinol. Metab. 88(10):4673-4676.
Voos et al., 1999, "Mechanisms of protein translocation into mitochondria," Biochim. Biophys. Acta. 1422(3):235-254.

*Primary Examiner*—Karen Cochrane Carlson
(74) *Attorney, Agent, or Firm*—Jones Day

(57) ABSTRACT

The present invention provides methods for screening modulators of 2-polyprenyl-3-methyl-6-methoxy-1,4-benzoquinone (DMQ) hydroxylation activity, inhibitors and activators of the activity, and methods of using such compounds. More particularly, this invention relates to modulators of and UbiF and CLK-1 enzyme activity and methods of identifying same.

28 Claims, 10 Drawing Sheets

```
        ATGACAAATC AACCAACGGA AATTGCCATT GTCGGCGGAG GAATGGTCGG CGGCGCACTG
  61    GCGCTGGGGC TGGCACAGCA CGGATTTACG GTAACGGTGA TCGAGCACGC AGAACCTGCA
 121    CCGTTTGTCG CTGATAGCCA ACCGGACGTG CGGATCTCGG CGATCAGCGC GGCTTCGGTA
 181    TCATTGCTTA AAGGGTTAGG GGTCTGGGAT GCAGTACAGG CTATGCGTTG CCATCCTTAC
 241    CGCAGACTGG AAACGTGGGA GTGGGAAACG GCGCATGTGG TATTTGACGC AGCCGAATTA
 301    AAGTTGCCGT TGCTTGGCTA TATGGTAGAA AACACTGTCC TGCAACAGGC ATTGTGGCAG
 361    GCGCTGGAAG CGCATCCGAA AGTAACGTTA CGTGTGCCAA CCTCGCTGAT TGCATTACAT
 421    CGAGATAATG ATCTTCAGGA GCTGGAGCTG AAAGGCGGTG AAGTGATTCG CGCGAAGCTG
 481    GTGATTGATG CCGACGGCGC AAATTCGCAG GTGCGGCAGA TGGCGGGAAT TGGCGTTCAT
 541    GCATGGCAGT ATGCGCAGTC GTGCATGTTG ATTAGCGTCC AGTGCGAGAA CGATCCCGGC
 601    GATAGCACCT GGCAGCAATT TACCCCGGAT GGACCGCGCG CGTTTCTGCC GCTGTTTGAT
 661    AACTGGGCAT CGCTGGTGTG GTACGACTCT CCGGCGCGCA TTCGCCAGTT GCAGAATATG
 721    AATATGGCGC AGTTACAGGT GGAAATCGCG AAGCATTTCC CGTCGCGTCT GGGTTACGTT
 781    ACACCGCTTG CCGCTGGTGC GTTTCCGCTG ACACGCCGCC ATGCGTTGCA GTATGTGCAG
 841    CCGGGGCTTG CGCTGGTGGG TGATGCCGCG CACACCATCC ATCCGCTGGC GGGGCAGGGG
 901    GTGAATCTTG GTTATCGTGA TGTCGATGCC CTGATTGATG TTCTGGTGAA TGCCCGCAGC
 961    TACGGCGAAG CGTGGGCCAG TTATCCTGTC CTCAAGCGTT ACCAGATGCG GCGCATGGCG
1021    GATAACTTCA TTATGCAGAG CGGTATGGAT CTGTTTTATG CCGGATTCAG TAATAATCTG
1081    CCGCCGCTGC GTTTTGTGCG TAATCTTGGT TTGATGGCGG CGGAGCGTGC TGGCGTGTTG
1141    AAACGTCAGG CGCTGAAATA TGCGTTAGGG TTGTAG
```

Fig. 3

```
        ATGACAAATC AACCAACGGA AATTGCCATT GTCGGCGGAG GAATGGTCGG CGGCGCACTG
   61   GCGCTGGGGC TGGCACAGCA CGGATTTACG GTAACGGTGA TCGAGCACGC AGAACCTGCA
  121   CCGTTTGTCG CTGATAGCCA ACCGGACGTG CGGATCTCGG CGATCAGCGC GGCTTCGGTA
  181   TCATTGCTTA AAGGGTTAGG GGTCTGGGAT GCAGTACAGG CTATGCGTTG CCATCCTTAC
  241   CGCAGACTGG AAACGTGGGA GTGGGAAACG GCGCATGTGG TATTTGACGC AGCCGAATTA
  301   AAGTTGCCGT TGCTTGGCTA TATGGTAGAA AACACTGTCC TGCAACAGGC ATTGTGGCAG
  361   GCGCTGGAAG CGCATCCGAA AGTAACGTTA CGTGTGCCAA CCTCGCTGAT TGCATTACAT
  421   CGAGATAATG ATCTTCAGGA GCTGGAGCTG AAAGGCGGTG AAGTGATTCG CGCGAAGCTG
  481   GTGATTGGTG CCGACGGCGC AAATTCGCAG GTGCGGCAGA TGGCGGGAAT TGGCGTTCAT
  541   GCATGGCAGT ATGCGCAGTC GTGCATGTTG ATTAGCGTCC AGTGCGAGAA CGATCCCGGC
  601   GATAGCACCT GGCAGCAATT TACCCCGGAT GGACCGCGCG CGTTTCTGCC GCTGTTTGAT
  661   AACTGGGCAT CGCTGGTGTG GTACGACTCT CCGGCGCGCA TTCGCCAGTT GCAGAATATG
  721   AATATGGCGC AGTTACAGGT GGAAATCGCG AAGCATTTCC CGTCGCGTCT GGGTTACGTT
  781   ACACCGCTTG CCGCTGGTGC GTTTCCGCTG ACACGCCGCC ATGCGTTGCA GTATGTGCAG
  841   CCGGGGCTTG CGCTGGTGGG TGATGCCGCG CACACCATCC ATCCGCTGGC GGGGCAGGGG
  901   GTGAATCTTG GTTATCGTGA TGTCGATGCC CTGATTGATG TTCTGGTGAA TGCCCGCAGC
  961   TACGGCGAAG CGTGGGCCAG TTATCCTGTC CTCAAGCGTT ACCAGATGCG GCGCATGGCG
 1021   GATAACTTCA TTATGCAGAG CGGTATGGAT CTGTTTTATG CCGGATTCAG TAATAATCTG
 1081   CCGCCGCTGC GTTTTGTGCG TAATCTTGGT TTGATGGCGG CGGAGCGTGC TGGCGTGTTG
 1141   AAACGTCAGG CGCTGAAATA TGCGTTAGGG TTGTAG
```

Fig. 4

```
ubiF(wt)    MTNQPTEIAIVGGGMVGGALALGLAQHGFAVTVIEHAEPAPFVADSQPDVRISAISAASV
            ||||||||||||||||||||||||||||||||||||||||||||||||||||||||||||
ubiF(411)   MTNQPTEIAIVGGGMVGGALALGLAQHGFAVTVIEHAEPAPFVADSQPDVRISAISAASV 61     SLLKGLGVWDAVQAMRCHPYRRLETWEWETAHVVFDAAELKLPLLGYMVENTVLQQALWQ
            ||||||||||||||||||||||||||||||||||||||||||||||||||||||||||||
     54     SLLKGLGVWDAVQAMRCHPYRRLETWEWETAHVVFDAAELKLPLLGYMVENTVLQQALWQ 121     ALEAHPKVTLRVPGSLIALHRHDDLQELELKGGEVI RAKLVIGADGANSQVRQMAGIGVH
            |||||||||||||||||||||||||||||||||||| ||||||T||||||||||||||||
    114     ALEAHPKVTLRVPGSLIALHRHDDLQELELKGGEVI RAKLVIDADGANSQVRQMAGIGVH.

181     AWQYAQSCMLISVQCENDPGDSTWQQFTPDGPRAFLPLFDNWASLVWYDSPARIRQLQNM
            ||||||||||||||||||||||||||||||||||||||||||||||||||||||||||||
    174     AWQYAQSCMLISVQCENDPGDSTWQQFTPDGPRAFLPLFDNWASLVWYDSPARIRQLQNM

241     NMAQLQAEIAKHFPSRLGYVTPLAAGAFPLTRRHALQYVQPGLALVGDAAHTIHPLAGQG
            ||||||||||||||||||||||||||||||||||||||||||||||||||||||||||||
    234     NMAQLQAEIAKHFPSRLGYVTPLAAGAFPLTRRHALQYVQPGLALVGDAAHTIHPLAGQG

301     VNLGYRDVDALIDVLVNARSYGEAWASYPVLKRYQMRRMADNFIMQ SGMDLFYAGFSNNL
            |||||||||||||||||||||||||||||||||||||||||||||| |||||||||||||
    294     VNLGYRDVDALIDVLVNARSYGEAWASYPVLKRYQMRRMADNFIMQ SGMDLFYAGFSNNL

361     PPLRFMRNLGLMAAERAGVLKRQALKYALGL
            |||||||||||||||||||||||||||||||
    354     PPLRFMRNLGLMAAERAGVLKRQALKYALGL
```

Fig. 5

SEQUENCE LISTING

<160> NUMBER OF SEQ ID NOS: 15

<210> SEQ ID NO 1
<211> LENGTH: 1176
<212> TYPE: DNA
<213> ORGANISM: E. coli
<220> FEATURE:
<223> OTHER INFORMATION: ubiF(411) mutant allele

<400> SEQUENCE: 1

```
atgacaaatc aaccaacgga aattgccatt gtcggcggag gaatggtcgg cggcgcactg    60
gcgctggggc tggcacagca cggatttacg gtaacggtga tcgagcacgc agaacctgca   120
ccgtttgtcg ctgatagcca accggacgtg cggatctcgg cgatcagcgc ggcttcggta   180
tcattgctta aagggttagg ggtctgggat gcagtacagg ctatgcgttg ccatccttac   240
cgcagactgg aaacgtggga gtgggaaacg gcgcatgtgg tatttgacgc agccgaatta   300
aagttgccgt tgcttggcta tatggtagaa aacactgtcc tgcaacaggc attgtggcag   360
gcgctggaag cgcatccgaa agtaacgtta cgtgtgccaa cctcgctgat tgcattacat   420
cgagataatg atcttcagga gctggagctg aaaggcggtg aagtgattcg cgcgaagctg   480
gtgattgatg ccgacggcgc aaattcgcag gtgcggcaga tggcgggaat tggcgttcat   540
gcatggcagt atgcgcagtc gtgcatgttg attagcgtcc agtgcgagaa cgatcccggc   600
gatagcacct ggcagcaatt taccccggat ggaccgcgcg cgtttctgcc gctgtttgat   660
aactgggcat cgctggtgtg gtacgactct ccggcgcgca ttcgccagtt gcagaatatg   720
aatatggcgc agttacaggt ggaaatcgcg aagcatttcc cgtcgcgtct gggttacgtt   780
acaccgcttg ccgctggtgc gtttccgctg acacgccgcc atgcgttgca gtatgtgcag   840
ccggggcttg cgctggtggg tgatgccgcg cacaccatcc atccgctggc ggggcagggg   900
gtgaatcttg gttatcgtga tgtcgatgcc ctgattgatg ttctggtgaa tgcccgcagc   960
tacggcgaag cgtgggccag ttatcctgtc ctcaagcgtt accagatgcg gcgcatggcg  1020
gataacttca ttatgcagag cggtatggat ctgtttttatg ccggattcag taataatctg  1080
ccgccgctgc gttttgtgcg taatcttggt ttgatggcgg cggagcgtgc tggcgtgttg  1140
aaacgtcagg cgctgaaata tgcgttaggg ttgtag                            1176
```

<210> SEQ ID NO 2
<211> LENGTH: 1176
<212> TYPE: DNA
<213> ORGANISM: E. coli
<220> FEATURE:
<223> OTHER INFORMATION: ubiF wildtype allele

<400> SEQUENCE: 2

```
atgacaaatc aaccaacgga aattgccatt gtcggcggag gaatggtcgg cggcgcactg    60
gcgctggggc tggcacagca cggatttacg gtaacggtga tcgagcacgc agaacctgca   120
ccgtttgtcg ctgatagcca accggacgtg cggatctcgg cgatcagcgc ggcttcggta   180
tcattgctta aagggttagg ggtctgggat gcagtacagg ctatgcgttg ccatccttac   240
cgcagactgg aaacgtggga gtgggaaacg gcgcatgtgg tatttgacgc agccgaatta   300
aagttgccgt tgcttggcta tatggtagaa aacactgtcc tgcaacaggc attgtggcag   360
gcgctggaag cgcatccgaa agtaacgtta cgtgtgccaa cctcgctgat tgcattacat   420
cgagataatg atcttcagga gctggagctg aaaggcggtg aagtgattcg cgcgaagctg   480
gtgattggtg ccgacggcgc aaattcgcag gtgcggcaga tggcgggaat tggcgttcat   540
gcatggcagt atgcgcagtc gtgcatgttg attagcgtcc agtgcgagaa cgatcccggc   600
gatagcacct ggcagcaatt taccccggat ggaccgcgcg cgtttctgcc gctgtttgat   660
aactgggcat cgctggtgtg gtacgactct ccggcgcgca ttcgccagtt gcagaatatg   720
aatatggcgc agttacaggt ggaaatcgcg aagcatttcc cgtcgcgtct gggttacgtt   780
acaccgcttg ccgctggtgc gtttccgctg acacgccgcc atgcgttgca gtatgtgcag   840
ccggggcttg cgctggtggg tgatgccgcg cacaccatcc atccgctggc ggggcagggg   900
```

```
gtgaatcttg gttatcgtga tgtcgatgcc ctgattgatg ttctggtgaa tgcccgcagc    960
tacggcgaag cgtgggccag ttatcctgtc ctcaagcgtt accagatgcg gcgcatggcg   1020
gataacttca ttatgcagag cggtatggat ctgttttatg ccggattcag taataatctg   1080
ccgccgctgc gttttgtgcg taatcttggt ttgatggcgg cggagcgtgc tggcgtgttg   1140
aaacgtcagg cgctgaaata tgcgttaggg ttgtag                             1176
```

<210> SEQ ID NO 3
<211> LENGTH: 391
<212> TYPE: PRT
<213> ORGANISM: E. coli
<220> FEATURE:
<223> OTHER INFORMATION: ubiF wildtype allele

<400> SEQUENCE: 3

```
Met Thr Asn Gln Pro Thr Glu Ile Ala Ile Val Gly Gly Met Val
 1               5                  10                  15

Gly Gly Ala Leu Ala Leu Gly Leu Ala Gln His Gly Phe Ala Val Thr
                20                  25                  30

Val Ile Glu His Ala Glu Pro Ala Pro Phe Val Ala Asp Ser Gln Pro
            35                  40                  45

Asp Val Arg Ile Ser Ala Ile Ser Ala Ala Ser Val Ser Leu Leu Lys
        50                  55                  60

Gly Leu Gly Val Trp Asp Ala Val Gln Ala Met Arg Cys His Pro Tyr
65                  70                  75                  80

Arg Arg Leu Glu Thr Trp Glu Trp Glu Thr Ala His Val Val Phe Asp
                85                  90                  95

Ala Ala Glu Leu Lys Leu Pro Leu Leu Gly Tyr Met Val Glu Asn Thr
            100                 105                 110

Val Leu Gln Gln Ala Leu Trp Gln Ala Leu Glu Ala His Pro Lys Val
        115                 120                 125

Thr Leu Arg Val Pro Gly Ser Leu Ile Ala Leu His Arg His Asp Asp
    130                 135                 140

Leu Gln Glu Leu Glu Leu Lys Gly Gly Glu Val Ile Arg Ala Lys Leu
145                 150                 155                 160

Val Ile Gly Ala Asp Gly Ala Asn Ser Gln Val Arg Gln Met Ala Gly
                165                 170                 175

Ile Gly Val His Ala Trp Gln Tyr Ala Gln Ser Cys Met Leu Ile Ser
            180                 185                 190

Val Gln Cys Glu Asn Asp Pro Gly Asp Ser Thr Trp Gln Gln Phe Thr
        195                 200                 205

Pro Asp Gly Pro Arg Ala Phe Leu Pro Leu Phe Asp Asn Trp Ala Ser
    210                 215                 220

Leu Val Trp Tyr Asp Ser Pro Ala Arg Ile Arg Gln Leu Gln Asn Met
225                 230                 235                 240

Asn Met Ala Gln Leu Gln Ala Glu Ile Ala Lys His Phe Pro Ser Arg
                245                 250                 255

Leu Gly Tyr Val Thr Pro Leu Ala Ala Gly Ala Phe Pro Leu Thr Arg
            260                 265                 270

Arg His Ala Leu Gln Tyr Val Gln Pro Gly Leu Ala Leu Val Gly Asp
        275                 280                 285

Ala Ala His Thr Ile His Pro Leu Ala Gly Gln Gly Val Asn Leu Gly
    290                 295                 300

Tyr Arg Asp Val Asp Ala Leu Ile Asp Val Leu Val Asn Ala Arg Ser
```

```
                   305                 310                 315                 320
Tyr Gly Glu Ala Trp Ala Ser Tyr Pro Val Leu Lys Arg Tyr Gln Met
                325                 330                 335

Arg Arg Met Ala Asp Asn Phe Ile Met Gln Ser Gly Met Asp Leu Phe
            340                 345                 350

Tyr Ala Gly Phe Ser Asn Asn Leu Pro Pro Leu Arg Phe Met Arg Asn
                355                 360                 365

Leu Gly Leu Met Ala Ala Glu Arg Ala Gly Val Leu Lys Arg Gln Ala
        370                 375                 380

Leu Lys Tyr Ala Leu Gly Leu
385                 390

<210> SEQ ID NO 4
<211> LENGTH: 391
<212> TYPE: PRT
<213> ORGANISM: E. coli
<220> FEATURE:
<223> OTHER INFORMATION: ubiF(411) mutant allele

<400> SEQUENCE: 4

Met Thr Asn Gln Pro Thr Glu Ile Ala Ile Val Gly Gly Gly Met Val
 1               5                  10                  15

Gly Gly Ala Leu Ala Leu Gly Leu Ala Gln His Gly Phe Ala Val Thr
            20                  25                  30

Val Ile Glu His Ala Glu Pro Ala Pro Phe Val Ala Asp Ser Gln Pro
        35                  40                  45

Asp Val Arg Ile Ser Ala Ile Ser Ala Ala Ser Val Ser Leu Leu Lys
    50                  55                  60

Gly Leu Gly Val Trp Asp Ala Val Gln Ala Met Arg Cys His Pro Tyr
65                  70                  75                  80

Arg Arg Leu Glu Thr Trp Glu Trp Glu Thr Ala His Val Val Phe Asp
                85                  90                  95

Ala Ala Glu Leu Lys Leu Pro Leu Leu Gly Tyr Met Val Glu Asn Thr
            100                 105                 110

Val Leu Gln Gln Ala Leu Trp Gln Ala Leu Glu Ala His Pro Lys Val
        115                 120                 125

Thr Leu Arg Val Pro Gly Ser Leu Ile Ala Leu His Arg His Asp Asp
    130                 135                 140

Leu Gln Glu Leu Glu Leu Lys Gly Gly Glu Val Ile Arg Ala Lys Leu
145                 150                 155                 160

Val Ile Asp Ala Asp Gly Ala Asn Ser Gln Val Arg Gln Met Ala Gly
                165                 170                 175

Ile Gly Val His Ala Trp Gln Tyr Ala Gln Ser Cys Met Leu Ile Ser
            180                 185                 190

Val Gln Cys Glu Asn Asp Pro Gly Asp Ser Thr Trp Gln Gln Phe Thr
        195                 200                 205

Pro Asp Gly Pro Arg Ala Phe Leu Pro Leu Phe Asp Asn Trp Ala Ser
    210                 215                 220

Leu Val Trp Tyr Asp Ser Pro Ala Arg Ile Arg Gln Leu Gln Asn Met
225                 230                 235                 240

Asn Met Ala Gln Leu Gln Ala Glu Ile Ala Lys His Phe Pro Ser Arg
                245                 250                 255

Leu Gly Tyr Val Thr Pro Leu Ala Ala Gly Ala Phe Pro Leu Thr Arg
            260                 265                 270

Arg His Ala Leu Gln Tyr Val Gln Pro Gly Leu Ala Leu Val Gly Asp
```

```
                275                 280                 285
Ala Ala His Thr Ile His Pro Leu Ala Gly Gln Gly Val Asn Leu Gly
    290                 295                 300

Tyr Arg Asp Val Asp Ala Leu Ile Asp Val Leu Val Asn Ala Arg Ser
305                 310                 315                 320

Tyr Gly Glu Ala Trp Ala Ser Tyr Pro Val Leu Lys Arg Tyr Gln Met
                325                 330                 335

Arg Arg Met Ala Asp Asn Phe Ile Met Gln Ser Gly Met Asp Leu Phe
            340                 345                 350

Tyr Ala Gly Phe Ser Asn Asn Leu Pro Pro Leu Arg Phe Met Arg Asn
        355                 360                 365

Leu Gly Leu Met Ala Ala Glu Arg Ala Gly Val Leu Lys Arg Gln Ala
    370                 375                 380

Leu Lys Tyr Ala Leu Gly Leu
385                 390

<210> SEQ ID NO 5
<211> LENGTH: 39
<212> TYPE: DNA
<213> ORGANISM: Artificial Sequence
<220> FEATURE:
<223> OTHER INFORMATION: Primer SHP2224 for site-directed mutagenesis

<400> SEQUENCE: 5
cacaagatta cgtgatgcgg cgcttcatca tcatgatac                    39

<210> SEQ ID NO 6
<211> LENGTH: 39
<212> TYPE: DNA
<213> ORGANISM: Artificial Sequence
<220> FEATURE:
<223> OTHER INFORMATION: Primer SHP2225 for site-directed mutagenesis

<400> SEQUENCE: 6
gtatcatgat gatgaagctc ctcatcacgt aatcttgtg                    39

<210> SEQ ID NO 7
<211> LENGTH: 31
<212> TYPE: DNA
<213> ORGANISM: Artificial Sequence
<220> FEATURE:
<223> OTHER INFORMATION: Primer SHP1511 for verify site-directed
      mutagenesis

<400> SEQUENCE: 7
ggcatatgtt ccgtgtaata acccgtggag c                            31

<210> SEQ ID NO 8
<211> LENGTH: 28
<212> TYPE: DNA
<213> ORGANISM: Artificial Sequence
<220> FEATURE:
<223> OTHER INFORMATION: Primer SHP1513 for verify site-directed
      mutagenesis

<400> SEQUENCE: 8
ggcatatggg aaaagaaggt gcaatggc                                28

<210> SEQ ID NO 9
<211> LENGTH: 35
<212> TYPE: DNA
<213> ORGANISM: Artificial Sequence
<220> FEATURE:
```

<223> OTHER INFORMATION: Primer SHP1514 for verify site-directed
mutagenesis

<400> SEQUENCE: 9 gggatcctc aaattttctc agcaatcgca atagc                                35

<210> SEQ ID NO 10
<211> LENGTH: 564
<212> TYPE: DNA
<213> ORGANISM: C. elegans
<220> FEATURE:
<223> OTHER INFORMATION: C. elegans CLK-1 (Genbank accession number
NM_065727)

<400> SEQUENCE: 10
atgttccgtg taataacccg tggagcacat actgctgctt ctcgtcaagc acttatagag    60
aagatcattc gagttgatca tgctggagag cttggagccg atcggattta cgctggacag   120
ttggctgttt tgcaaggttc atctgttggt tcagtaatca aaagatgtg ggatgaggag    180 aaagaacatt tagatacaat ggaaagatta gctgctaaac acaatgtacc tcatactgtt   240
ttctctccag ttttcagtgt ggctgctta t gctctcggtg tcggttcagc acttctagga   300
aaagaaggtg caatggcttg tacaattgca gttgaagaac tcattggaca acattataat   360
gatcaattga agaactcct tgccgacgat cctgaaacac acaaagaatt gctgaaaatt    420
ctcacaagat tacgtgatga ggagcttcat catcatgata ctggagtaga acacgatgga   480
atgaaggctc cagcctactc ggctctcaaa tggattattc aaactggatg caagggagct   540
attgcgattg ctgagaaaat ttga                                          564

<210> SEQ ID NO 11
<211> LENGTH: 187
<212> TYPE: PRT
<213> ORGANISM: C. elegans
<220> FEATURE:
<223> OTHER INFORMATION: C. elegans CLK-1

<400> SEQUENCE: 11

Met Phe Arg Val Ile Thr Arg Gly Ala His Thr Ala Ala Ser Arg Gln
 1               5                   10                  15

Ala Leu Ile Glu Lys Ile Ile Arg Val Asp His Ala Gly Glu Leu Gly
            20                  25                  30

Ala Asp Arg Ile Tyr Ala Gly Gln Leu Ala Val Leu Gln Gly Ser Ser
        35                  40                  45

Val Gly Ser Val Ile Lys Lys Met Trp Asp Glu Glu Lys Glu His Leu
    50                  55                  60

Asp Thr Met Glu Arg Leu Ala Ala Lys His Asn Val Pro His Thr Val
65                  70                  75                  80

Phe Ser Pro Val Phe Ser Val Ala Ala Tyr Ala Leu Gly Val Gly Ser
                85                  90                  95

Ala Leu Leu Gly Lys Glu Gly Ala Met Ala Cys Thr Ile Ala Val Glu
            100                 105                 110

Glu Leu Ile Gly Gln His Tyr Asn Asp Gln Leu Lys Glu Leu Leu Ala
        115                 120                 125

Asp Asp Pro Glu Thr His Lys Glu Leu Leu Lys Ile Leu Thr Arg Leu
    130                 135                 140

Arg Asp Glu Glu Leu His His His Asp Thr Gly Val Glu His Asp Gly
145                 150                 155                 160

Met Lys Ala Pro Ala Tyr Ser Ala Leu Lys Trp Ile Ile Gln Thr Gly

```
                165                 170                 175
Cys Lys Gly Ala Ile Ala Ile Ala Glu Lys Ile
            180                 185

<210> SEQ ID NO 12
<211> LENGTH: 654
<212> TYPE: DNA
<213> ORGANISM: Homo Sapiens
<220> FEATURE:
<223> OTHER INFORMATION: Human CLK-1 (Genbank accession number
      NM_016138)

<400> SEQUENCE: 12
atgagttgcg ccggggcggc ggcggctccc cgcctttggc ggctgcgccc gggggcccgg      60
cggtccctct cagcttatgg aagaagaacc agtgtcagat ttcgcagttc aggaatgact     120
ttagacaata tcagtcgggc agctgtggat cgaataatcc gggtggatca tgcaggcgaa     180
tatggagcaa accgcatcta tgccgggcag atggctgtcc tgggtcggac cagcgtcggg     240
ccagtcattc agaaaatgtg ggatcaagaa aaggaccatt tgaaaaagtt caatgagttg     300
atggttacgt tcagggtccg gccaacagtt ctgatgccct gtggaacgt gctgggttt      360 gcactggggg cggggaccgc cttgctcggg aaggaaggtg ccatggcctg caccgtggcg     420
gtggaagaga gcatagcaca tcactacaac aaccagatca ggacgctgat ggaggaggac     480
cctgaaaaat acgaggaact tcttcagctg ataaagaaat tcgggatga gagcttgag      540 caccatgaca taggcctcga ccatgatgca gaattggctc cagcctatgc cgtcctgaag     600
agcattatcc aggccggatg cagagtggcg atatatttat cagaaagatt ataa          654

<210> SEQ ID NO 13
<211> LENGTH: 217
<212> TYPE: PRT
<213> ORGANISM: Homo sapiens
<220> FEATURE:
<223> OTHER INFORMATION: Human CLK-1

<400> SEQUENCE: 13

Met Ser Cys Ala Gly Ala Ala Ala Pro Arg Leu Trp Arg Leu Arg
 1               5                  10                  15

Pro Gly Ala Arg Arg Ser Leu Ser Ala Tyr Gly Arg Arg Thr Ser Val
            20                  25                  30

Arg Phe Arg Ser Ser Gly Met Thr Leu Asp Asn Ile Ser Arg Ala Ala
        35                  40                  45

Val Asp Arg Ile Ile Arg Val Asp His Ala Gly Glu Tyr Gly Ala Asn
    50                  55                  60

Arg Ile Tyr Ala Gly Gln Met Ala Val Leu Gly Arg Thr Ser Val Gly
65                  70                  75                  80

Pro Val Ile Gln Lys Met Trp Asp Gln Glu Lys Asp His Leu Lys Lys
                85                  90                  95

Phe Asn Glu Leu Met Val Thr Phe Arg Val Arg Pro Thr Val Leu Met
            100                 105                 110

Pro Leu Trp Asn Val Leu Gly Phe Ala Leu Gly Ala Gly Thr Ala Leu
        115                 120                 125

Leu Gly Lys Glu Gly Ala Met Ala Cys Thr Val Ala Val Glu Glu Ser
    130                 135                 140

Ile Ala His His Tyr Asn Asn Gln Ile Arg Thr Leu Met Glu Glu Asp
145                 150                 155                 160

Pro Glu Lys Tyr Glu Glu Leu Leu Gln Leu Ile Lys Lys Phe Arg Asp
```

-continued

```
                165                 170                 175
Glu Glu Leu Glu His His Asp Ile Gly Leu Asp His Asp Ala Glu Leu
            180                 185                 190
Ala Pro Ala Tyr Ala Val Leu Lys Ser Ile Ile Gln Ala Gly Cys Arg
        195                 200                 205
Val Ala Ile Tyr Leu Ser Glu Arg Leu
        210                 215
```

<210> SEQ ID NO 14
<211> LENGTH: 654
<212> TYPE: DNA
<213> ORGANISM: Mus musculus
<220> FEATURE:
<223> OTHER INFORMATION: Mouse CLK-1 (Genbank accession number
      NM_009940)

<400> SEQUENCE: 14

```
atgagcgccg ccggagccat agcggctgct tccgtgggac gcctgcgcac tggtgtccgg      60
aggcccttct cagagtatgg aagaggcctc atcatcaggt gtcacagttc ggggatgacc     120
ttagacaata ttaaccgggc agccgtggat cgaataattc gggtggatca cgctggtgaa     180
tatggagcaa accgcatcta tgcagggcaa atggccgtgc tcggtcggac cagtgttggc     240
cctgtcattc agaaaatgtg ggatcaagag aagaaccatt tgaaaaagtt caacgagttg     300
atgattgcat tcagggtccg acctacggtt ttgatgccct tgtggaacgt ggcaggcttt     360
gccctggggg caggaactgc cttgctgggg aaggaaggag caatggcctg caccgtggcg     420
gtagaagagt ctatcgctaa tcactacaac aaccagatcc gcatgctgat ggaagaggac     480
cctgagaagt atgaggagct gctgcaggtc atcaagcagt tcgcgatga ggagcttgaa      540
caccacgata caggcctgga ccatgacgca gagctggctc ccgcgtatgc cttgttgaag     600
aggattatcc aggccggatg cagtgcagcc atatatttat cagaaaggtt ttag           654
```

<210> SEQ ID NO 15
<211> LENGTH: 217
<212> TYPE: PRT
<213> ORGANISM: Mus musculus
<220> FEATURE:
<223> OTHER INFORMATION: Mouse CLK-1

<400> SEQUENCE: 15

```
Met Ser Ala Ala Gly Ala Ile Ala Ala Ala Ser Val Gly Arg Leu Arg
  1               5                  10                  15
Thr Gly Val Arg Arg Pro Phe Ser Glu Tyr Gly Arg Gly Leu Ile Ile
            20                  25                  30
Arg Cys His Ser Ser Gly Met Thr Leu Asp Asn Ile Asn Arg Ala Ala
        35                  40                  45
Val Asp Arg Ile Ile Arg Val Asp His Ala Gly Glu Tyr Gly Ala Asn
    50                  55                  60
Arg Ile Tyr Ala Gly Gln Met Ala Val Leu Gly Arg Thr Ser Val Gly
 65                  70                  75                  80
Pro Val Ile Gln Lys Met Trp Asp Gln Glu Lys Asn His Leu Lys Lys
                85                  90                  95
Phe Asn Glu Leu Met Ile Ala Phe Arg Val Arg Pro Thr Val Leu Met
            100                 105                 110
Pro Leu Trp Asn Val Ala Gly Phe Ala Leu Gly Ala Gly Thr Ala Leu
        115                 120                 125
Leu Gly Lys Glu Gly Ala Met Ala Cys Thr Val Ala Val Glu Glu Ser
```

```
               130                 135                 140
Ile Ala Asn His Tyr Asn Asn Gln Ile Arg Met Leu Met Glu Glu Asp
145                 150                 155                 160

Pro Glu Lys Tyr Glu Glu Leu Leu Gln Val Ile Lys Gln Phe Arg Asp
                165                 170                 175

Glu Glu Leu Glu His His Asp Thr Gly Leu Asp His Asp Ala Glu Leu
                180                 185                 190

Ala Pro Ala Tyr Ala Leu Leu Lys Arg Ile Ile Gln Ala Gly Cys Ser
            195                 200                 205

Ala Ala Ile Tyr Leu Ser Glu Arg Phe
210                 215
```

METHOD FOR IDENTIFYING MODULATORS OF CLK-1 AND UBIF ACTIVITY

The application claims priority under 35 U.S.C. § 119(e) to provisional patent application No. 60/468,707, filed May 8, 2003, which is incorporated herein by reference in its entirety.

1. INTRODUCTION

This invention relates to modulators of 2-polyprenyl-3-methyl-6-methoxy-1,4-benzoquinone (DMQ) hydroxylation activity and methods of identifying same. More particularly, this invention relates to modulators of UbiF and CLK-1 enzyme activity and methods of identifying same. This invention also relates to novel compounds identified using such methods.

2. BACKGROUND OF THE INVENTION

2.1 Ubiquinone

Ubiquinone (coenzyme Q, or Q) is a prenylated benzoquinone that is an essential co-factor in the mitochondrial respiratory chain, where its function is best characterized. Q is also found in many other locations in the cell, such as the lysosome and Golgi membranes, as well as in nuclear and plasma membranes. Q is a membrane constituent, whose head group is capable of accepting and donating electrons, and whose lipidic side-chain is composed of a varying number of isoprene subunits. A possible role for Q as a dietary antioxidant for treating conditions that involve altered cellular redox states is being intensely studied in animal experiments, as well as in human clinical trials. Q is also used extensively as a nutritional supplement to combat aging and age-associated diseases.

Nine enzymes have been described in great detail in *E. coli* as participating in Q biosynthesis (FIG. 1). They are all membrane-bound, except the first one, ubiC, which is a soluble chorismate lyase. The next enzyme in the pathway is the prenyltransferase ubiA that attaches the isoprenoid side chain to the quinone ring (8 subunits in *E. coli*). The other enzymes are grouped in three categories: decarboxylases (ubiD and ubiX), monooxygenases (ubiB, uniH, uniF), and methyltransferases (ubiG, ubiE).

Q has numerous functions in the cell. It is involved in electron transport in the inner mitochondrial membrane, the plasma membrane, and the membrane of the lysosome. Q is also a cofactor for several cellular enzymes (e.g. dihydroorotate dehydrogenase, which is necessary for nucleic acid biosynthesis) and other proteins and complexes such as the mitochondrial uncoupling proteins (UCP), which regulate metabolic heat production and the mitochondrial permeability transition pore (MPTP), which regulates programmed cell death. Moreover, Q is also an antioxidant that is able to protect membranes and other cellular constituents from oxidative damage. The length of the Q isoprenoid side-chain is controlled in a species-specific manner by the enzyme polyprenyl-diphosphate synthase. The nematode *C. elegans* produces $Q_9$ (the subscript denotes the chain length), *E. coli* produces $Q_8$, and *S. cerevisiae* $Q_6$. In mammals both $Q_9$ and $Q_{10}$ are found: $Q_9$ is predominant in rats and mice, while $Q_{10}$ is predominant in humans (Dallner and Sindelar, 2000 Regulation of ubiquinone metabolism. *Free Radic Biol Med*, 29, 285–294).

2.2 CLK-1 Function clk-1 encodes an enzyme, CLK-1, which participates in one of the last steps of Q biosynthesis and is responsible for DMQ hydroxylation (similar to ubiF in bacteria, see FIG. 1). clk-1 in eukaryotes and ubiF in most prokaryotes encode enzymes which are responsible for DMQ hydroxylation. Consistent with this, HPLC analysis of the quinone content of *C. elegans* clk-1 mutants, namely qm30, qm51, and e2519, reveals that they accumulate DMQ (FIG. 2). In these mutants, the DMQ levels are comparable to the Q levels found in the wild type. Mouse embryos and mouse embryonic stem cells in which the clk-1 homolog has been knocked out also accumulate DMQ. DMQ is a quinone that is able to transport electrons, although less efficiently than Q. It is able to function in the mitochondrial respiratory chain, in particular in complex I and III and thus is able to sustain respiration at relatively high rates. Indeed, the function of purified mitochondria, and mitochondrial enzymes, from clk-1 mutants appears to be almost intact compared to the wild type. Furthermore, synthetic $DMQ_2$ (the subscript denotes the chain length) is able to function as a co-factor for electron transport from complex I and, albeit more poorly, from complex II. In *E. coli*, $DMQ_8$ is able to sustain respiration in isolated membranes although at a lower rate than $Q_8$. Similarly, $DMQ_9$ is able to sustain electron transport in eukaryotic mitochondria. It has been previously shown that DMQ cannot functionally replace Q everywhere in the cell. In fact, clk-1 mutants are dependent upon the presence of exogenous Q in the bacterial food. However, dietary Q is not sufficient as a quinone source, as *C. elegans* mutants devoid of endogenous Q or DMQ (coq-3 mutants) cannot develop even in the presence of exogenous Q (Hihi et al., 2002 Ubiquinone is necessary for *Caenorhabditis elegans* development at mitochondrial and non-mitochondrial sites. *J Biol Chem*, 277, 2202–2206; Miyadera et al., 2001 Altered quinone biosynthesis in the long-lived clk-1 mutants of *Caenorhabditis elegans*. *J Biol Chem*, 276, 7713–7716) 2.1 clk-1 and the Clk phenotype clk-1 mutants of the nematode *Caenorhabditis elegans* display the Clk phenotype characterized by the deregulation and lengthening of embryonic and post-embryonic development, as well as of adult rhythmic behaviours such as the defecation and pharyngeal pumping cycles. The Clk phenotype also leads to an extended lifespan, as clk-1 mutants live longer than wild-type worms clk-1 encodes a 187 amino acid protein, CLK-1, that is localized in mitochondria, and that is homologous to the yeast protein Coq7p, which has been shown to be required for ubiquinone (coenzyme Q, or Q) biosynthesis (Ewbank et al., 1997 Structural and functional conservation of the *Caenorhabditis elegans* timing gene clk-1. *Science*, 275, 980–983). The lack of CLK-1, as observed in *C. elegans* and mouse embryonic stem cells, leads to decreased reactive oxygen species (ROS) production and modulation of Q levels (WO 03/014383). Recent studies using mimetics of physiological scavenging enzymes like superoxide dismutases and catalases indicated that reduction in ROS levels could bring about therapeutic benefit. Other agents that have been used in clinical studies are antioxidants that are normally found in the body, like ubiquinone or vitamin E. However their pharmacological profile is far from ideal, as they need to be administered in very large amounts for a small benefit to be observed.

In view of the central role of ubiquinone in a variety of biological activities, inhibitors and activators of DMQ hydroxylation enzymes in prokaryotes and eukaryotes are of great interest to many in pharmaceutical research. The present invention provides methods for identifying compounds that modulate DMQ hydroxylation enzymes, and methods of using such compounds.

3. SUMMARY OF THE INVENTION

The present invention relates to the screening of compounds that modulate the activity of enzymes that carry out hydroxylation of demethoxyubiquinone.

In one aspect, the inventors developed drug discovery assays in a prokaryotic cell system based on the complementation of a deficiency in prokaryotic DMQ hydroxylase by an eukaryotic counterpart. Under certain conditions, DMQ hydroxylase is essential to normal growth and proliferation of prokaryotes, and bacteria, in particular. In another aspect, prokaryotic and eukaryotic DMQ hydroxylases apparently share very little structural similarity. The inventors of the present invention recognize that the differences between bacterial and eukaryotic DMQ hydroxylases combined with the ubiquitous and conserved nature of bacterial DMQ hydroxylases in pathogens make bacterial DMQ hydroxylase an attractive target for antibiotic development.

In various embodiments, the invention provides primary screening assays to initially screen inhibitors of DMQ hydroxylase, and secondary assays to characterize the compounds that scored positive in these assays. The assays of the invention are adaptable to high-throughput screening.

In one embodiment, the screening assays of the invention targets a eukaryotic protein that exhibits DMQ hydroxylase activity, generally referred to herein as a CLK-1 protein which participates in mitochondrial respiration. The prokaryotic test cells comprise a target gene construct comprising an expressible genetic sequence encoding a target eukaryotic DMQ hydroxylase. The assay can identify compounds that modulate the activity of CLK-1 protein including but not limited to its DMQ hydroxylase activity, and affect its functions including that of Q biosynthesis. Any eukaryotic CLK-1 homolog can be used in the screening assays. The *C. elegans* CLK-1, mouse CLK-1 and human CLK-1 are preferably used in the methods of the invention. *Escherichia coli* cells that are deficient in DMQ hydroxylation activity are preferably used in the methods.

In another embodiment, the screening assays of the invention targets a prokaryotic DMQ hydroxylase, referred to herein as a UbiF protein, which is unique to prokaryotes and under certain conditions essential for growth. Accordingly, the prokaryotic test cells comprise a target gene construct comprising an expressible genetic sequence encoding a target prokaryotic DMQ hydroxylase. The assay can identify compounds that modulate the enzymatic activity of a UbiF protein and affect its function in Q biosynthesis. Any prokaryotic UbiF protein can be used in the screening assays. Generally, bacterial UbiF protein are preferred. *Escherichia coli* cells that are deficient in UbiF activity can also be used in these methods of the invention.

Secondary assays are provided to evaluate hits identified in the primary assays. Such assays are used to determine toxicity, and to confirm that inhibitors identified in the primary assays act specifically against one type of DMQ hydroxylases or act against DMQ hydroxylases of a broad spectrum of organisms. Compounds identified in the primary assay based on growth inhibition of a test species can be tested for efficacy against other bacterial pathogens to confirm that the positive compounds are effective against a broad range of microorganisms. The high-throughput screening assays is an effective method for identifying compounds that interfere with DMQ hydroxylation function.

The methods of the invention have a high probability of identifying useful drugs for several reasons. First, the screening system targets an essential factor that is ubiquitous and conserved throughout the bacterial kingdom. The target is highly selective as the mammalian counterpart shows very low amino acid similarities to the bacterial enzymes. The high-throughput primary screen of the invention allows for the easy visible identification of positive hits. Compounds testing positive in this whole cell growth assay have penetrated the cell permeability barrier and are functional in the intracellular environment.

In accordance with one embodiment of the present invention there is provided a method of identifying a compound which modulates enzymatic activity of a protein capable of carrying out 2-polyprenyl-3-methyl-6-methoxy-1,4-benzoquinone (DMQ) hydroxylation comprising determining a first level of DMQ hydroxylation activity in the absence of the compound; and determining a second level of DMQ hydroxylation activity in the presence of the compound, wherein a difference between the first and second levels of DMQ hydroxylation activity is indicative of the compound being a modulator of activity of an enzyme capable of carrying out DMQ hydroxylation.

In a preferred method of the present invention, the enzyme is selected from the group consisting of CLK-1, a homolog of CLK-1, a functional mutant of CLK-1, an enzymatically functional fragment of CLK-1, an enzymatically functional fragment of a homolog of CLK-1, an enzymatically functional fragment of a functional mutant of CLK-1, UbiF, a homolog of UbiF, a functional mutant of UbiF, an enzymatically functional fragment of UbiF, an enzymatically functional fragment of a homolog of UbiF, and an enzymatically functional fragment of a functional mutant of UbiF.

In accordance with another embodiment of the present invention there is provided a method of identifying a compound which is a CLK-1-specific modulator comprising determining a difference between a first level of CLK-1 activity in the absence of the compound and a second level of CLK-1 activity in the presence of the compound, and determining a difference between a first level of activity of an analog of the CLK-1 in the presence of the compound and a second level of activity of an analog of the CLK-1 in the absence of the compound, wherein a difference between the first and second levels of CLK-1 activity and a lack of difference between the first and second levels of activity of the analog is indicative of the compound being a CLK-1-specific modulator.

In accordance with another embodiment of the present invention there is provided a method of identifying a compound which is a UbiF-specific modulator comprising determining a difference between a first level of UbiF activity in the absence of the compound and a second level of UbiF activity in the presence of the compound, and determining a difference between a first level of activity of an analog of the UbiF in the presence of the compound and a second level of activity of an analog of the UbiF in the absence of the compound, wherein a difference between the first and second levels of UbiF activity and a lack of difference between the first and second levels of activity of the analog is indicative of the compound being a UbiF-specific modulator.

In accordance with another embodiment of the present invention there is provided a method of identifying a compound which is a UbiF-specific modulator comprising determining a difference between a first level of UbiF activity in the absence of the compound and a second level of UbiF activity in the presence of the compound, and determining a difference between a first level of activity of an analog of the UbiF in the presence of the compound and a second level of activity of an analog of the UbiF in the absence of the compound, wherein a difference between the first and second levels of UbiF activity and a lack of difference between the first and second levels of activity of the analog is indicative of the compound being a UbiF-specific modulator.

In accordance with another embodiment of the present invention there is provided a kit for identifying a compound which modulates activity of an enzyme capable of carrying out DMQ hydroxylation. For example, the kit can include *E. coli* strain containing a mutation that impairs UbiF function, a DNA sequence encoding for a eukaryotic CLK-1, and/or a DNA sequence encoding for a UbiF.

4. BRIEF DESCRIPTION OF DRAWINGS

FIG. 3 illustrates the DNA sequence of the ubiF(411) mutant allele.

FIG. 4 illustrates the DNA sequence of the ubiF wildtype allele.

FIG. 5 illustrates a comparison of the wild type UbiF sequence and UbiF(411) sequence, showing the point mutation in the UbiF sequence (the site of the mutation is underlined) of JF496 (UbiF), as compared to the wild type.

Figure 8:
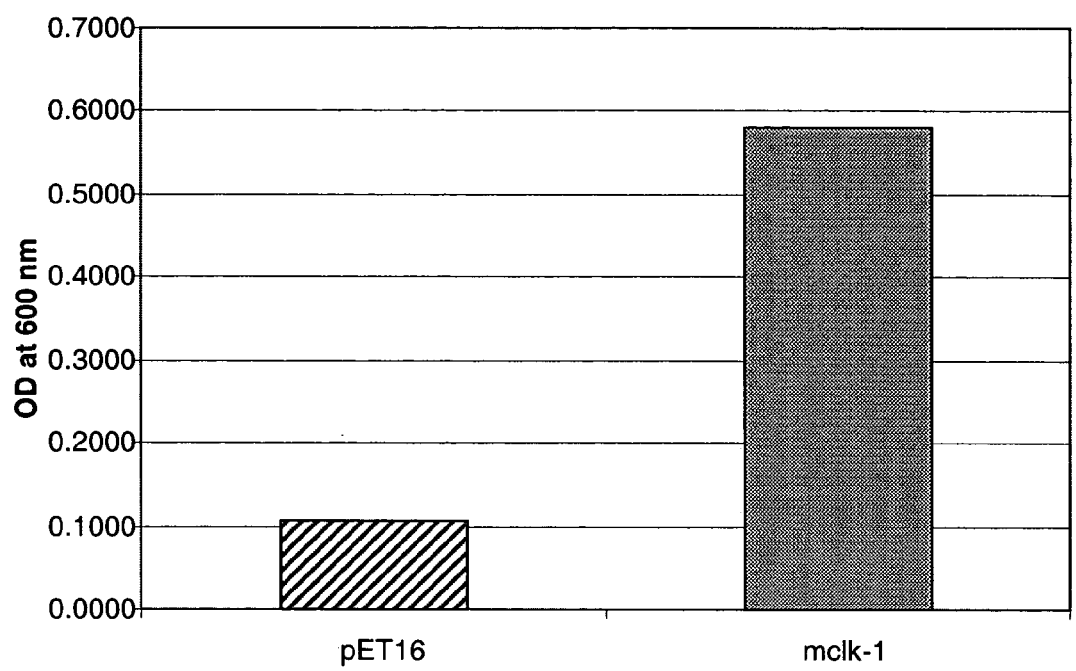

FIG. 8. Mouse CLK-1 complements JF496 growth.

Figure 9:
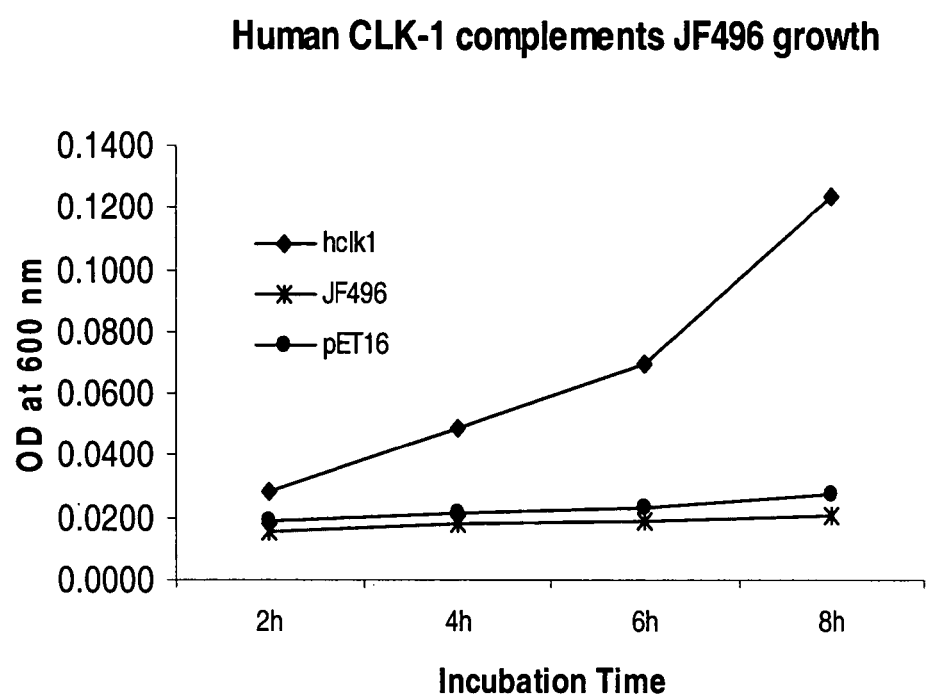

FIG. 9. Human CLK-1 complements JF496 growth.

Figure 10:
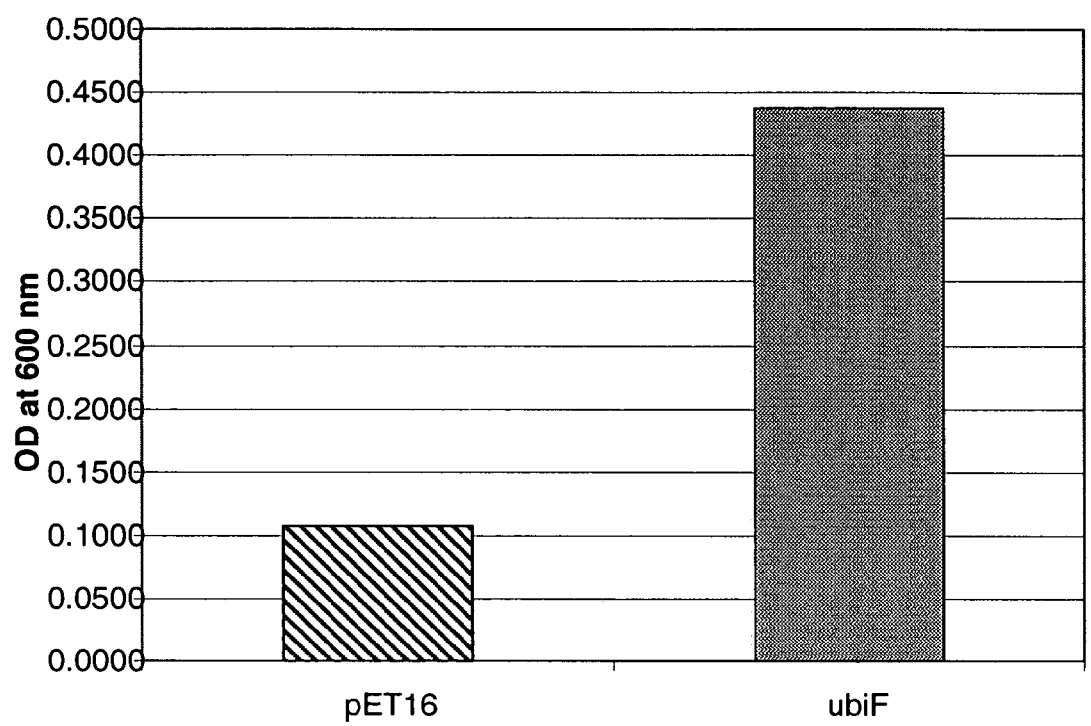

FIG. 10. UbiF complements JF496 growth. The UbiF activity is provided by expression from a recombinant gene construct comprising the *E. coli* ubiF coding sequence.

5. DETAILED DESCRIPTION OF THE INVENTION

The present invention relates to the screening of compounds that modulate the activity of enzymes that are involved in ubiquinone biosynthesis in eukaryotes and prokaryotes, in particular, enzymes that carry out hydroxylation of demethoxyubiquinone. The methods of the invention are used to identify therapeutic compounds useful in the treatment of a variety of diseases and conditions, including metabolic diseases and infectious diseases.

As used herein, the term "Q" refers to ubiquinone, which is also known as coenzyme Q. The term includes ubiquinones of any polyprenyl side chain length. Typically, the side chain length ranges from 6 to 10 isoprenoid groups. To indicate a ubiquinone having a specific length of polyprenyl side chain, a subscript is used, e.g., $Q_9$ denotes ubiquinone having a side chain of 9 isoprenoid groups which is found in *C. elegans* and humans; $Q_8$ has a side chain of 8 isprenoid groups and is found in *E. coli*.

As used herein, the term "DMQ" refers to 2-polyprenyl-3-methyl-6-methoxy-1,4-benzoquinone, also known as demethoxyubiquinone, and includes demethoxyubiquinones of any polyprenyl side chain length. Typically, the side chain length ranges from 6 to 10 isoprenoid groups. Similar to the nomenclature for ubiqunones, a DMQ having a specific length of isoprenoid side chain is indicated by a subscript, e.g., $DMQ_9$ denotes DMQ having a side chain of 9 isoprene groups which is found in humans and *C. elegans*; $DMQ_8$ has a side chain of 8 isprenoid groups and is found in *E. coli*.

As used herein, the term "DMQ hydroxylase" refers to an enzyme that converts DMQ to 2-polyprenyl-3-methyl-5-hydroxy-1,4-benzoquinone (also known as 3-hydroxy ubiquinone or 3-hydroxy Q). This enzyme adds a hydroxy (—OH) group to the 5'0 position of the benzoquinone.

In one aspect, the inventors discovered that eukaryotic DMQ hydroxylase can complement a deficiency in prokaryotic DMQ hydroxylase activity which is apparently essential to normal growth and proliferation of prokaryotic cells. Based on this finding, screening assays are designed that use growth characteristics and phenotypes of prokaryotic test cells as an indicator of the activity of an eukaryotic protein that exhibits DMQ hydroxylase activity. These assays are relatively inexpensive and advantageously adaptable to high-throughput screening formats of the industry. Accordingly, the invention provides convenient and high throughput cell-based assays that employ prokaryotic test cells comprising an eukaryotic DMQ hydroxylase as a drug target. Direct DMQ or Q measurements in eukaryotic cells can be used subsequently in validating the activity of compounds identified by the assays based on prokaryotic cells. Lead compounds identified by these assays are used in development of drugs for treatment of a range of diseases and conditions associated with oxidative stress.

In another aspect, the invention provides the use of a prokaryotic DMQ hydroxylase as a drug target. In eukaryotes, the DMQ hydroxylation step is carried out by enzymes encoded by clk-1 homologs and, in most bacteria by ubiF homologs. However, protein sequence comparison of CLK-1 and UbiF proteins from various species reveals that these two enzymes are highly divergent (Table 1). For example, there is only 3% amino acids identity between hCLK-1 and UbiF from *E. coli* K-12, and the identity drops to 2% when compared to the enterohemorrhagic *E. coli* O157:H7 strain, and to 1.5% compared to *Salmonella typhimurium*. Although some of the fundamental mechanisms and components of cellular metabolism have been highly conserved throughout evolution, significant adaptive changes in the process have occurred independently in bacteria and eukaryotes. The enzymes required for hydroxylation of demethoxyubiquinone appear to be the results of this divergent evolution.

TABLE 1 ubiF and clk-1 are analogous genes

| | Amino acid identity of encoded protein (%) | | |
|---|---|---|---|
| | *E. coli* UbiF | *H. sapiens* hCLK-1 | *C. elegans* CLK-1 |
| *E. coli* K-12 UbiF | 100 | 3.3 | 1.6 |
| *E. coli* O157:H7 UbiF | 98.5 | 1.9 | 1.7 |
| *S. typhimurium* UbiF | 85.9 | 1.5 | 1.9 |
| *Y. pestis* UbiF | 62.8 | 1.9 | 1.9 |
| *H. sapiens* CLK-1 | 3.3 | 100 | 45.7 |
| *C. elegans* CLK-1 | 1.6 | 45.7 | 100 |
| *M. musculus* CLK-1 | 3.2 | 85.2 | 46.5 |
| *S. cerevisiae* CLK-1 | | 26.1 | 26.1 |
| *S. pombe* CLK-1 | | 36.1 | 36.1 |

CLK-1 does not share obvious structural features with UbiF. The CLK-1 protein lacks a consensus monooxygenase domain, is smaller in size (21 kDa instead of 46 kDa), and the few shared amino acids are dispersed within the sequence, and are not clustered. In addition, CLK-1 is a member of the di-iron carboxylate family of proteins. It has a putative iron binding consensus sequence (<n> indicates that the adjacent amino acids are separated by other amino acids): E<n>EXXH<n>E<n>EXXH. This sequence is found in some monooxygenases and hydroxylases. However it is absent from the sequence of UbiF. Apparently, UbiF is the only gene involved in Q biosynthesis that is structurally dissimilar to its eukaryotic counterpart. All the other enzymes in Q biosynthesis (encoded by the other ubi genes) in bacteria shares a high degree of structural similarity with eukaryotic enzymes.

The present invention contemplates exploiting this divergence in amino acid sequences of DMQ hydroxylases in eukaryotes and prokaryotes in discovering drugs that target the eukaryotic clk-1 gene or CLK-1 protein, or conversely, selectively act on the prokaryotic ubiF gene or UbiF protein. Compounds that act specifically against bacteria, which include pathogens, represent a new class of antibiotics. UbiF is widely found and conserved throughout the bacterial kingdom. Thus, it is likely that any compounds which are effective at inhibiting UbiF of one bacterial species will have an inhibitory effect on the UbiF or its functional equivalents in a related species, and possibly in a wide spectrum of bacteria. Because UbiF has no structural equivalent in eukaryotic cells, the target for the antibiotic compounds identified by screening assays of the invention, is absent in a subject's cells. As a result, the potential toxicity of the compounds is likely to be low. The compounds identified by the methods of the invention are likely to be highly selective against prokaryotic pathogens, and preferably effective against a broad range of such pathogens, such as bacteria. Compounds that inhibit UbiF activity are useful as antibiotics for treatment of infectious diseases caused by bacteria in animals or plants, bacteriocidal agents for sterilization of bacteria-contaminated objects and materials, or bacteriostatic agents that prevent the spread of bacteria.

As used herein, the term "CLK-1" refers generically to a protein comprising DMQ hydroxylase activity that shares sequence homology with the amino acid sequence of C. elegans CLK-1 as set forth in SEQ ID NO: 11, human CLK-1 as set forth in SEQ ID NO: 13, mouse CLK-1 as set forth in SEQ ID NO: 15 or other DMQ hydroxylases in eukaryotes that share structural features with proteins of the di-iron carboxylate family. One such feature is the presence of a putative iron binding consensus sequence: E<n>EXXH<n>E<n>EXXH (<n> indicates that the adjacent amino acids are separated by other amino acids). Preferably, the CLK-1 proteins of the invention share at least 25%, 40%, 50%, 60%, 70%, 80%, 90%, 95%, 99% amino acid sequence identity, with any one of C. elegans, human or mouse CLK-1. The term "clk-1" refers to any polynucleotide that encode a CLK-1 protein and includes genomic DNA, cDNA, as well as RNA.

As used herein, the term "UbiF" refers generically to a DMQ hydroxylase that shares sequence homology with the amino acid sequence of E. coli UbiF as set forth in SEQ ID NO: 3 and other DMQ hydroxylases in prokaryotes that share structural features, such as the presence of a monooxygenase motif, with the bacterial proteins. Preferably, the UbiF proteins of the invention share at least 25%, 40%, 50%, 60%, 70%, 80%, 90%, 95%, 99% amino acid sequence identity, with any one of E. coli, E. coli O157:H7, S. typhimurium or Y. pestis UbiFs. The term "ubiF" refers to any nucleic acid that encode a UbiF, and includes genomic DNA, cDNA, as well as RNA. The target gene sequences useful in the invention are described in details in Section 5.1.

The term "target DMQ hydroxylase" refers to a protein exhibiting a DMQ hydroxylase activity that is being tested in an assay of the invention to identify modulators of the activities of the protein, and depending on the nature of the assay, encompasses either a CLK-1 or a UbiF protein. It is contemplated that a target DMQ hydroxylase may have additional activities which are not necessarily related to ubiquinone biosynthesis. Therefore, the term as used herein are not limited to proteins that exhibit solely DMQ hydroxylase activity. The target DMQ hydroxylase can be from a vertebrate animal, a mammal, a primate, or a human.

As used herein, the phrase "target DMQ hydroxylase gene expression", refers to transcription of a clk-1 or ubiF gene which produces clk-1 or ubiF pre-mRNA, clk-1 or ubiF mRNA, and/or translation of clk-1 or ubiF mRNA to produce CLK-1 or UbiF protein. The terms "clk-1 gene expression", or "ubiF gene expression" refer to transcription of the respective gene which produces the respective pre-mRNA, the respective mRNA, and/or translation of the respective mRNA to produce CLK-1 or UbiF protein. The gene constructs that enable target DMQ hydroxylase gene expression and test cells comprising target DMQ hydroxylase are described in details in Section 5.2 and 5.3.

Accordingly, the invention provides primary assays for identifying compounds that increase or decrease the activity of a target protein comprising DMQ hydroxylase activity which is expressed in a test cell that is deficient in DMQ hydroxylase and that provides a means for assessing the activity of the target protein. The target DMQ hydroxylase complements the deficiency of the test cells and allow the cells to grow at a relatively higher rate. Thus, in a preferred embodiment, the invention provides a method of screening for a test compound that modulates the activity of a CLK-1 protein, comprising contacting a test cell with a test compound for a time sufficient to allow said test compound to modulate the activity of a CLK-1 protein in said test cell, wherein said test cell is deficient in endogenous DMQ hydroxylase activity and comprises an expressible polynucleotide encoding said CLK-1 protein; and detecting a change in DMQ hydroxylase activity, wherein an increase or decrease in DMQ hydroxylase activity in the test cell contacted with the test compound relative to the DMQ hydroxylase activity in a test cell not contacted with the test compound, indicates that the test compound modulates the activity of said CLK-1 protein.

In another preferred embodiment, the invention provides a method of screening for a test compound that inhibits a target DMQ hydroxylase activity, comprising contacting test cells with a test compound for a time sufficient to allow the test compound to modulate DMQ hydroxylase activity in said test cells, wherein said test cells are deficient in endogenous DMQ hydroxylase activity and comprise an expressible polynucleotide encoding a target DMQ hydroxylase; and determining the growth rate of said test cells under selective condition, wherein a decrease in growth rate of said test cells relative to test cells under the same selective condition and not contacted with said test compound, indicates that said test compound inhibits said target DMQ hydroxylase.

In yet another preferred embodiment, the invention provides a method of screening for a test compound that enhances a target DMQ hydroxylase activity, comprising contacting test cells with a test compound for a time sufficient to allow the test compound to modulate DMQ hydroxylase activity in said test cells, wherein said test cells are deficient in endogenous DMQ hydroxylase activity and comprise an expressible polynucleotide encoding a target DMQ hydroxylase; and determining the growth rate of said test cells under selective condition, wherein an increase in growth rate of said test cells relative to test cells under the same selective condition and not contacted with said test compound, indicates that said test compound inhibits said target DMQ hydroxylase. Detailed description of the steps of the primary assays are provided in Section 5.5. Kit for screening test compound that modulates the activity of a target DMQ hydroxylase are described in Section 5.7.

Test compounds scoring positive in the screening assays of the invention are putative agents that inhibit DMQ hydroxylase activity of the target protein and/or other activities of the target protein, and, as such, may be useful as lead compounds for the development of therapeutic agents useful for the treatment of metabolic or infectious diseases. Anti-infective drugs based on such lead compounds are likely to be effective in controlling growth in a broad spectrum of bacteria while causing minimal side effects to the treated subject.

The invention further provides secondary assays which are used to further characterize the test compounds which produced positive results in the primary screening assays of the invention. Such assays are described in Section 5.6. During the evaluation of positive compounds of the invention and selection of leads for further development, the two main considerations will be biological activity and chemical structure. To be considered for further development, a compound should act specifically to the target protein. For example, a candidate antibiotic compound that inhibits UbiF activity should prefereably have no or little inhibitory effect on CLK-1. The chemical structure should preferebly be amenable to further chemical modification, so that analogs and derivatives can be synthesized and analyzed for structure-activity relationship and other preclinical studies, such as toxicology, pharmacokinetics, and drug metabolism.

The invention further provides methods of uses of the compounds identified by the methods of the invention, such as but not limited to treating or preventing a disease or medical condition in a subject. In various such methods, a subject is administered an effective amount of a compound that inhibits CLK-1 activity, wherein said disease or medical condition is atherosclerosis, ischemia, a vascular complication of diabetes, cancer, or obesity.

In other embodiments, the invention provides methods of treating or preventing a disease or medical condition in a subject comprising administering to a subject an effective amount of a compound that enhances CLK-1 activity, wherein said disease or medical condition is Parkinson's disease or Friedreich's ataxia.

In other embodiments, the invention provides methods for treating a subject with an infectious disease caused by bacteria comprising administering to the subject a therapeutically effective amount of a compound that inhibits UbiF activity in said bacteria.

Preferably, the subject receiving the compound is human, a companion animal or a livestock animal.

In further embodiments, the invention provides methods for sterilizing bacteria-contaminated object or material comprising contacting the bacteria-contaminated object or material with a compound that inhibits UbiF activity in said bacteria.

5.1 Polynucleotides Encoding DMQ Hyroxylases

Polynucleotides encoding DMQ hydroxylases, i.e., CLK-1s and UbiFs of the invention, can be obtained by any method known in the art. A polynucleotide is intended to include DNA molecules (e.g., cDNA, genomic DNA), RNA molecules (e.g., hnRNA, pre-mRNA, mRNA), and DNA or RNA analogs generated using nucleotide analogs. The polynucleotide can be single-stranded or double-stranded. An isolated polynucleotide is one which is distinguished from other polynucleotides that are present in the natural source of the polynucleotide.

The CLK-1 amino acid sequence and nucleotide sequence for, inter alia, human, mouse, yeast and *C. elegans* are available in the public databases (e.g. Genbank). The amino acid sequences for human CLK-1, mouse CLK-1, and *C. elegans* CLK-1 are set forth in SEQ ID NOS: 13, 15 and 11, respectively. The use of clk-1 polynucleotides encoding human CLK-1, mouse CLK-1 and *C. elegans* CLK-1 are preferred. The invention also provides the use of clk-1 polynucleotides encoding other CLK-1 proteins that share at least 25%, 40%, 50%, 60%, 70%, 80%, 90%, 95%, 99% amino acid sequence identity, with any of *C. elegans*, human, or mouse CLK-1, and share structural features of the di-iron carboxylate protein family. Examples of sequences of CLK-1 homologs, and their accession numbers in public databases are provided in Table 2. It is contemplated that any of these CLK-1 proteins and their coding sequences can be used in the methods of the invention.

TABLE 2

Exemplary CLK-1 sequences and their accession numbers in the database of the United States National Center for Biotechnology Information (NCBI) which is accessible by internet.

| Species | Cross Reference | Accession No. |
|---|---|---|
| Homo sapiens | gi\|25453484\|ref\|NP_057222.2\| | NP_057222 |
| Homo sapiens | gi\|13112023\|gb\|AAH03185.1\| | AAH03185 |
| Homo sapiens | gi\|12643397\|sp\|Q99807\|COQ7_HUMAN | Q99807 |
| Homo sapiens | gi\|5456747\|gb\|AAD43648.1\| | AAD43648 |
| Homo sapiens | gi\|10436638\|dbj\|BAB14876.1\| | BAB14876 |
| Homo sapiens | gi\|12052820\|emb\|CAB66582.1\| | CAB66582 |
| Homo sapiens | gi\|20385593\|gb\|AAM21346.1\| | AAM21346 |
| Mus musculus | gi\|20587962\|ref\|NP_034070.1\| | NP_034070 |
| Mus musculus | gi\|5921833\|sp\|P97478\|COQ7_MOUSE | P97478 |
| Mus musculus | gi\|25518277\|pir\|\|JC7756 | JC7756 |
| Mus musculus | gi\|3415017\|gb\|AAC31572.1\| | AAC31572 |
| Mus musculus | gi\|5456749\|gb\|AAD43649.1\| | AAD43649 |
| Mus musculus | gi\|24217460\|gb\|AAH38681.1\| | AAH38681 |
| Homo sapiens | gi\|3811295\|gb\|AAC69451.1 | AAC69451 |
| Mus musculus | gi\|3806019\|gb\|AAC69179.1\| | AAC69179 |
| Rattus norvegicus | gi\|25453396\|ref\|NP_036917.1\| | NP_036917 |
| Rattus norvegicus | gi\|2851472\|sp\|Q63619\|COQ7_RAT | Q63619 |
| Rattus norvegicus | gi\|7446711\|pir\|\|T10806 | T10806 |
| Rattus norvegicus | gi\|1932725\|gb\|AAB51656.1\| | AAB51656 |
| Rattus norvegicus | gi\|7446710\|pir\|\|S71353 | S71353 |
| Mus musculus | gi\|20380261\|gb\|AAH28276.1 | AAH28276 |
| Mus musculus | gi\|1841536\|gb\|AAC53055.1\| | AAC53055 |

Also used in the methods of the invention are clk-1 polynucleotides that encode variants of CLK-1, examples of which are provided in Section 7.2. For some variants, the sequence variation(s) results in partial activity or inactivation of the enzyme. Such functionally impaired variants are referred to as clk-1 mutants or CLK-1 mutants.

Nucleic acids encoding UbiF can be obtained by any method known in the art. The UbiF amino acid and nucleotide sequences for, inter alia, *E. coli* K-12, *E. coli* O157:H7, *S. typhimurium*, *Y. pestis* are available in the public databases. The amino acid and nucleotide sequences for wild type *E. coli* UbiF are set forth in SEQ ID NOS: 3 and 2, respectively. Preferably, the invention provides the use of ubiF polynucleotides encoding other UbiF proteins that share at least 25%, 40%, 50%, 60%, 70%, 80%, 90%, 95%, 99% amino acid sequence identity, with any one of *E. coli* K-12, *E. coli* O157:H7, *S. typhimurium*, *S. aureus*, *M. tuberculosis*, or *Y. pestis* UbiF protein.

In various embodiments, the invention contemplates using ubiF polynucleotides encoding UbiF homologs of various prokaryotes, preferably animal or plant pathogens, more preferably bacteria, and most preferably bacterial pathogens that cause human diseases. Non-limiting examples of UbiFs that are used as target DMQ hydroxylase can be derived from various groups of bacteria including but not limited to, gram positive cocci, such as *Staphylococci* (e.g., *S. aureus*), *Streptococci* (e.g., *S. pneumoniae*, *S. pyrogens*, *S. faecalis*, *S. viridans*); gram positive bacilli, such as *Bacillus* (e.g., *B. anthracis*), *Corynebacterium* (e.g., *C. diphtheriae*), *Listeria* (e.g., *L. monocytogenes*); gram negative cocci, such as *Neisseria* (e.g., *N. gonorrhoeae*, *N. meningitidis*); gram negative bacilli, such as *Haemophilus* (e.g. *H. influenzae*), *Pasteurella* (e.g., *P. multocida*), *Proteus* (e.g., *P. mirabilis*), *Salmonella* (e.g., *S. typhimurium*), *Shigella* (e.g. *Shigella flexneri*), *Escherichia* (e.g., *E. coli*, and *E. coli* O157:H7), *Klebsiella* (e.g., *K. pneumoniae*), *Serratia* (e.g. *S. marcescens*), *Yersinia* (e.g., *Y. pestis*), *Providencia* species, *Enterobacter* species, *Bacteroides* (e.g., *fragilis*), *Acinetobacter* species, *Campylobacter* (e.g., *C. jejuni*), *Pseudomonas* (e.g., *P. aeruginosa*), *Bordetella* (e.g., *B. pertussis*), *Brucella* species, *Fracisella* (e.g., *F. tularensis*), *Clostridia* (e.g., *C. perfriugens*), *Helicobacter* (e.g., *H. pylori*), *Vibrio* (e.g., *V. cholerae*), *Mycoplasma* (e.g., *M. pneumoniae*), *Legionella* (e.g., *L. pneumophila*), *Spirochetes* (e.g. *Treponema*, *Leptospira* and *Borrelia*), *Mycobacteria* (e.g., *M. tuberculosis*), *Nocardia* (e.g., *N. asteroides*), and *Chlamydia* (e.g., *C. trachomatis*).

Examples of ubiF polynucleotides encoding UbiF homologs, and their accession numbers in public databases are provided in Table 3. It is contemplated that these ubiF polynucleotides and UbiF proteins can be used as a drug target without any limitation in any drug screening assays for identifying antibiotic compounds against the organism from which the target is derived. Preferably, these drug targets are used in the primary and secondary assays of the invention. It is also contemplated that the ubiF polynucleotides can be used to mutate or delete a native gene encoding UbiF in an organism by techniques known in the art so as to create a UbiF-deficient host cells of that particular organism. Such host cells can be used to develop test cells useful in the methods of the invention.

TABLE 3

Exemplary UbiF homologs and their designations.

| Species | ORF/gene designation |
|---|---|
| *Mycobacterium tuberculosis* H37Rv | Mtub0:Rv1751 |
| *Mycobacterium tuberculosis* CDC1551 | Mtub1:MT1794 |
| *Mycobacterium bovis* subsp. *bovis* AF2122/97 | Mbov0:Mb1780 |
| *Streptomyces coelicolor* A3(2) | scoe0:SCO0249_SCJ9A.28c |
| *Gloeobacter violaceus* PCC 7421 | gvio0:gll2827 |
| *Staphylococcus aureus* Mu50 | saur0:SAV2306 |
| *Staphylococcus aureus* N315 | saur1:SA2099 |
| *Staphylococcus aureus* MW2 | saur2:MW2225 |
| *Brucella melitensis* 16M | bmel0:BMEI0165 |
|  | bmel0:BMEII0694 |
|  | bmel0:BMEI1017 |
| *Bordetella bronchiseptica* RB50 | bbro0:CAE34983.1 |
|  | bbro0:CAE34361.1 |
|  | bbro0:CAE31394.1 |
|  | bro0:CAE32275.1 |
| *Bordetella parapertussis* | bpar0:CAE39430.1 |
|  | bpar0:CAE38847.1 |
|  | bpar0:CAE37624.1 |
|  | bpar0:CAE40220.1 |
| *Bordetella pertussis* Tohama I | Bper0:CAE43535.1 |
|  | bper0:CAE43676.1 |
|  | bper0:CAE42236.1 |
|  | bper0:CAE43398.1 |
| *Ralstonia solanacearum* GMI1000 | rsol0:RSc2893_RS00205 |
|  | rsol0:RSp0702_RS01747 |
| *Chromobacterium violaceum* ATCC 12472 | cvio0:ubiF |
| *Neisseria meningitidis* MC58 | Nmen0:NMB0323 |
| *Neisseria meningitidis* Z2491 | Nmen1:NMA2164 |
| *Shewanella oneidensis* MR-1 | sone0:SO1183 |
|  | sone0:SO0778 |
| *Escherichia coli* K-12 MG1655 | ecol0:ubiF |
|  | ecol0:visC |
| *Escherichia coli* O157:H7 | ecol1:ECs0700 |
|  | ecol1:ECs3777 |
|  | ecol1:ECs3778 |
| *Escherichia coli* O157:H7 EDL933 | ecol2:yleB |
|  | ecol2:visC |
| *Escherichia coli* CFT073 | ecol3:yleB |
|  | ecol3:visC |
| *Salmonella typhi* CT18 | styp0:yleB_STY0717 |
|  | styp0:STY3212 |
|  | styp0:STY3213_visB |
| *Salmonella typhimurium* LT2 | styp1:ubiF |
|  | styp1:visC |
|  | styp1:STM1546 |
| *Salmonella enterica* subsp. *enterica* serovar *Typhi* Ty2 3 | styp2:yleB |
|  | styp2:t2974 |
|  | styp2:visB |
| *Shigella flexneri* 2a 301 | sfle0:ubiF |
|  | sfle0:visC |
| *Shigella flexneri* 2a str. 2457T | sfle1:yleB |
|  | sfle1:visC |
| *Yersinia pestis* CO92 | ypes0:ubiF_YPO2621 |
|  | ypes0:visC_YPO0908 |
| *Yersinia pestis* KIM | ypes1:y1196 |
|  | ypes1:visC |
| *Candidatus Blochmannia floridanus* | bflo0:ubiF |
| *Coxiella burnetii* RSA 493 | cbur0:visC |
| *Haemophilus ducreyi* 35000HP | hduc0:ubiF |
| *Pseudomonas aeruginosa* PAO1 | paer0:visC |
|  | paer0:pobA |
| *Pseudomonas putida* KT2440 | pput0:ubiF |
|  | pput0:pobA |
| *Pseudomonas syringae* pv. tomato str. DC3000 | psyr0:ubiF |
|  | psyr0:pobA |
| *Vibrio cholerae* N16961 | vcho0:VC0963 |
|  | vcho0:VC2474 |
|  | vcho0:VC2475 |
| *Vibrio parahaemolyticus* RIMD 2210633 | vpar0:VP0735 |
|  | vpar0:VP2586 |
|  | vpar0:VP2587 |
| *Vibrio vulnificus* CMCP6 | vvul0:VV10265 |
|  | vvul0:VV11553 |
|  | vvul0:VV11552 |
| *Vibrio vulnificus* YJ016 | vvul1:VV0918 |
|  | vvul1:VV2845 |
|  | vvul1:VV2846 |

TABLE 3-continued

Exemplary UbiF homologs and their designations.

| Species | ORF/gene designation |
| --- | --- |
| *Xanthomonas axonopodis* pv. *citri* 306 | xaxo0:visC |
| *Xanthomonas campestris* pv. *campestris* ATCC 33913 3 | xcam0:visC.1 |
| | xcam0:visC.2 |
| | xcam0:pobA |
| *Xylella astidiosa* 9a5c | xfas0:XF0834 |
| | xfas0:XF0835 |

The present invention also encompasses uses of clk-1 or ubiF antisense polynucleotides, i.e., molecules which are complementary to a sense nucleic acid encoding a DMQ hydroxylase, e.g., complementary to the coding strand of a double-stranded cDNA molecule or complementary to an mRNA sequence. For example, ubiF antisense polynucleotides can be used to modulate or inhibit the expression of a UbiF in a cell. The antisense nucleic acid can be complementary to an entire coding strand, or to only a portion thereof, e.g., all or part of the protein coding region (or open reading frame). An antisense polynucleotide can be antisense to all or part of a non-coding region of the coding strand of a nucleotide sequence encoding a polypeptide of the invention. The non-coding regions are the 5' and 3' sequences which flank the coding region and are not typically translated into amino acids. The antisense oligonucleotides of the invention can be DNA or RNA or chimeric mixtures, derivatives, or variants thereof. The oligonucleotide can be modified at the base moiety, sugar moiety, or phosphate backbone, which can, for example, improve the oligonucleotide's pharmacokinetics and/or affect an oligonucleotide's hybridization to the target mRNA. An antisense oligonucleotide can be, for example, about 8, 10, 15, 20, 25, 30, 35, 40, 45 or 50 nucleotides or more in length. In one embodiment, the antisense oligonucleotide comprises sequences complementary to the 5' untranslated region or the 3' untranslated region. An antisense nucleic acid of the invention can be constructed using chemical synthesis and enzymatic ligation reactions using procedures known in the art.

The clk-1 or ubiF polynucleotides may be obtained by standard procedures known in the art from cloned DNA (e.g., a DNA "library"), by chemical synthesis, by cDNA cloning, or by the cloning of genomic DNA, or fragments thereof, purified from the desired cell (see, for example, Sambrook et al., 1989, Molecular Cloning, A Laboratory Manual, 2d Ed., Cold Spring Harbor Laboratory Press, Cold Spring Harbor, N.Y.; Glover, D. M. (ed.), 1985, DNA Cloning: A Practical Approach, MRL Press, Ltd., Oxford, U.K. Vol. I, II.) Clones derived from eukaryotic genomic DNA may contain regulatory and intron DNA regions in addition to coding regions; clones derived from cDNA will contain only exon sequences. Clones derived from prokaryotic genomes may contain multiple control elements and genes arranged in a polycistronic unit. Whatever the source, the gene should be molecularly cloned into a suitable vector for propagation of the gene and expression in the test cells.

A preferred method for isolating a clk-1 or ubiF gene is by the polymerase chain reaction (PCR), which can be used to amplify the desired sequence in a genomic or cDNA library. Synthetic oligonucleotides based on conserved sequences may be utilized as primers to amplify by PCR sequences from a source (RNA or DNA), preferably a cDNA library. One can choose to synthesize several different degenerate primers for use in the PCR reactions. It is also possible to vary the stringency of hybridization conditions used in priming the PCR reactions, to allow for greater or lesser degrees of nucleotide sequence similarity between the known nucleotide sequence and the nucleic acid of a clk-1 or ubiF being isolated. For cross species hybridization, low stringency conditions are preferred. For same species hybridization, moderately stringent conditions are preferred. After successful amplification of a segment of clk-1 or ubiF, that segment may be molecularly cloned and sequenced, and utilized as a probe to isolate a complete cDNA or genomic clone. This, in turn, will permit the determination and isolation of the gene's complete nucleotide sequence.

Additionally, a portion of the clk-1 or ubiF gene or its specific RNA, or a fragment thereof, can be purified or synthesized, and labeled, the generated DNA fragments may be screened by nucleic acid hybridization to the labeled probe (Benton, W. and Davis, R., 1977, Science 196:180; Grunstein, M. And Hogness, D., 1975, Proc. Natl. Acad. Sci. U.S.A. 72:3961). Those DNA fragments with substantial homology to the probe will hybridize. clk-1 or ubiF nucleic acids can be also identified and isolated by expression cloning using, for example, anti-clk-1 or anti-ubiF antibodies for selection.

Alternatives to obtaining the clk-1 or ubiF DNA by cloning or amplification include, but are not limited to, chemically synthesizing the gene sequence itself from the known clk-1 or ubiF sequence or making cDNA to the mRNA which encodes the CLK-1 or UbiF protein. Other methods are possible and within the scope of the invention.

Nucleic acids which are hybridizable to a clk-1 or ubiF nucleic acid (e.g., having sequence SEQ ID NO: 12 or 2), can be isolated by nucleic acid hybridization under conditions of low, high, or moderate stringency. By way of example and not limitation, procedures using such conditions of low stringency are as follows (see also Shilo and Weinberg, 1981, Proc. Natl. Acad. Sci. USA 78:6789 6792): filters containing DNA are pretreated for 6 h at 40° C. in a solution containing 35% formamide, 5×SSC, 50 mM Tris HCl (pH 7.5), 5 mM EDTA, 0.1% PVP, 0.1% Ficoll, 1% BSA, and 500 µg/ml denatured salmon sperm DNA. Hybridizations are carried out in the same solution with the following modifications: 0.02% PVP, 0.02% Ficoll, 0.2% BSA, 100 µg/ml salmon sperm DNA, 10% (wt/vol) dextran sulfate, and 5 20×106 cpm 32P labeled probe is used. Filters are incubated in hybridization mixture for 18 20 h at 40° C., and then washed for 1.5 h at 55° C. in a solution containing 2×SSC, 25 mM Tris HCl (pH 7.4), 5 mM EDTA, and 0.1% SDS. The wash solution is replaced with fresh solution and incubated an additional 1.5 h at 60° C. Filters are blotted dry and exposed for autoradiography. If necessary, filters are washed for a third time at 65 to 68° C. and reexposed to film. Other conditions of low stringency which may be used are well known in the art (e.g., as employed for cross-species hybridizations).

By way of example and not limitation, procedures using such conditions of high stringency are as follows: prehybridization of filters containing DNA is carried out for 8 h to overnight at 65° C. in buffer composed of 6×SSC, 50 mM Tris HCl (pH 7.5), 1 mM EDTA, 0.02% PVP, 0.02% Ficoll, 0.02% BSA, and 500 µg/ml denatured salmon sperm DNA. Filters are hybridized for 48 h at 65° C. in prehybridization mixture containing 100 µg/ml denatured salmon sperm DNA. Washing of filters is done at 37° C. for 1 h in a solution containing 2×SSC, 0.01% PVP, 0.01% Ficoll, and 0.01% BSA. This is followed by a wash in 0.1×SSC at 50°

C. for 45 min before autoradiography. Other conditions of high stringency which may be used are well known in the art.

For example, but not limited to, procedures using such conditions of moderate stringency are as follows: Filters containing DNA are pretreated for 6 h at 55° C. in a solution containing 6×SSC, 5× Denhart's solution, 0.5% SDS and 100 μg/ml denatured salmon sperm DNA. Hybridizations are carried out in the same solution. Filters are incubated in hybridization mixture for 18–20 h at 55° C., and then washed twice for 30 minutes at 60° C. in a solution containing 1×SSC and 0.1% SDS. Filters are blotted dry and exposed for autoradiogtaphy. Other conditions of moderate stringency which may be used are well-known in the art. Washing of filters is done at 37° C. for 1 h in a solution containing 2×SSC, 0.1% SDS.

Alternatively, a database may be searched to determine whether any amino acid sequences or nucleotide sequences display a certain level of homology or sequence identity with respect to the enzyme gene or enzyme. A variety of such databases are available to those skilled in the art, including GenBank and GenSeq. In various embodiments, the databases are screened to identify nucleic acids with at least 97%, at least 95%, at least 90%, at least 85%, at least 80%, at least 70%, at least 60%, at least 50%, or at least 40% nucleotide sequence identity to an enzyme gene sequence, or a portion thereof. In other embodiments, the databases are screened to identify polypeptides having at least 99%, at least 95%, at least 90%, at least 85%, at least 80%, at least 75%, at least 70%, at least 65%, at least 60%, at least 55%, at least 50%, at least 40% or at least 25% amino acid identity or similarity to a polypeptide encoded by the enzyme genes of the invention.

The determination of percent identity between two sequences can be accomplished using a mathematical algorithm. A preferred, non-limiting example of a mathematical algorithm utilized for the comparison of two sequences is the algorithm of Karlin and Altschul (1990, Proc Natl Acad Sci. 87:2264–2268), modified as in Karlin and Altschul (1993, Proc Natl Acad Sci. 90:5873–5877). Such an algorithm is incorporated into the NBLAST and XBLAST programs of Altschul et al. (1990, J. Mol. Biol. 215:403–410). BLAST nucleotide searches can be performed with the NBLAST program, score=100, wordlength=12 to obtain nucleotide sequences homologous to a polynucleotides of the invention. BLAST protein searches can be performed with the XBLAST program, score=50, wordlength=3 to obtain amino acid sequences homologous to a protein molecules of the invention. To obtain gapped alignments for comparison purposes, Gapped BLAST can be utilized as described in Altschul et al. (1997, Nucleic Acids Res. 25:3389–3402). Alternatively, PSI-Blast can be used to perform an iterated search which detects distant relationships between molecules. When utilizing BLAST, Gapped BLAST, and PSI-Blast programs, the default parameters of the respective programs (e.g., XBLAST and NBLAST) can be used. See the home page of web site of United States National Center for Biotechnology Information.

Another preferred, non-limiting example of a mathematical algorithm utilized for the comparison of sequences is the algorithm of Myers and Miller, (1988, CABIOS 4:11–17). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Additional algorithms for sequence analysis are known in the art and include ADVANCE and ADAM as described in Torellis and Robotti (1994, Comput. Appl. Biosci. 10:3–5); and FASTA described in Pearson and Lipman (1988, Proc Natl Acad Sci. 85:2444–2448). Within FASTA, ktup is a control option that sets the sensitivity and speed of the search. If ktup=2, similar regions in the two sequences being compared are found by looking at pairs of aligned residues; if ktup=1, single aligned amino acids are examined. ktup can be set to 2 or 1 for protein sequences, or from 1 to 6 for DNA sequences. The default if ktup is not specified is 2 for proteins and 6 for DNA. The percent identity between two sequences can be determined using techniques similar to those described above, with or without allowing gaps. In calculating percent identity, only exact matches are counted.

In addition, the invention also encompass polynucleotides encoding functional equivalents of CLK-1 and UbiF proteins. "Functional equivalent" as the term is utilized herein, refers to a polypeptide capable of interacting with DMQ in a manner substantially similar to the way in which wild type CLK-1 or UbiF would interact with DMQ, and preferably exhibiting at least a minimally detectable level of an activity that converts DMQ to 3-hydroxy Q.

Such functionally equivalent gene products include, but are not limited to, natural and genetically engineered variants of the polypeptides having an amino acid sequence set forth in SEQ ID NO: 3 or 13. Such equivalents gene products can contain, e.g., deletions, additions or substitutions of amino acid residues within the amino acid sequences encoded by the enzyme gene sequences described above, but which result in a silent change, thus producing a functionally equivalent product. Amino acid substitutions can be made on the basis of similarity in polarity, charge, solubility, hydrophobicity, hydrophilicity and/or the amphipathic nature of the residues involved. For example, nonpolar (i.e., hydrophobic) amino acid residues can include alanine (Ala or A), leucine (Leu or L), isoleucine (Ile or I), valine (Val or V), proline (Pro or P), phenylalanine (Phe or F), tryptophan (Trp or W) and methionine (Met or M); polar neutral amino acid residues can include glycine (Gly or G), serine (Ser or S), threonine (Thr or T), cysteine (Cys or C), tyrosine (Tyr or Y), asparagine (Asn or N) and glutamine (Gln or Q); positively charged (i.e., basic) amino acid residues can include arginine (Arg or R), lysine (Lys or K) and histidine (His or H); and negatively charged (i.e., acidic) amino acid residues can include aspartic acid (Asp or D) and glutamic acid (Glu or E). It will be apparent to those skilled in the art that such substitutions can be made outside the regions critical to the function of the molecule and still result in an active polypeptide. Examples of functionally equivalent variants and functionally impaired mutants of C. elegans CLK-1 are described in Section 7.2.

clk-1 or ubiF polynucleotides encoding polypeptides corresponding to one or more domains of the enzyme gene products (e.g., signal sequences, active sites, or substrate-binding domains), truncated or deleted enzymes (e.g., polypeptides in which one or more domains of the enzyme are deleted), and fusion proteins (e.g., proteins in which a full length or truncated or deleted enzyme, or a peptide or polypeptide corresponding to one or more domains of an enzyme is fused to an unrelated protein) are also within the scope of the present invention. Polynucleotides encoding fusion proteins can be made by ligating the appropriate nucleic acid sequences encoding the desired amino acid sequences to each other by methods known in the art, in the proper coding frame. Exemplary fusion proteins include, but are not limited to a luminescent protein, such as green fluorescent protein, which can provide a marker function. Preferably, such fusion proteins are also functional equivalents of CLK-1 or UbiF proteins.

5.2 Recombinant Gene Construct

In the present invention, a target DMQ hydroxylase gene sequence is inserted into a vector to obtain expression of the target DMQ hydroxylase in cells. Accordingly, an aspect of the invention pertains to vectors, preferably expression vectors, comprising a clk-1 or ubiF polynucleotide, nucleic acid sequence encoding a CLK-1 or UbiF polypeptide, a functionally equivalent thereof or a mutant thereof.

The term "target gene constructs" refers to a vector known in the art that has been manipulated by insertion or incorporation of target gene sequences. As used herein, the term "vector" refers to a polynucleotide capable of transporting another nucleic acid to which it has been linked. For example, one type of vector is a plasmid, which refers to a circular double stranded DNA loop into which additional DNA segments can be introduced. Another type of vector is a viral vector, wherein additional DNA segments can be introduced into the viral genome.

Such target gene constructs of the invention are preferably plasmids which contain a promoter sequence that is operably associated with the inserted target gene sequence. It typically contains an origin of replication as well as specific genes which allow phenotypic selection of the transformed cells. The term "operably-associated" or "operably-linked" refers to an association in which a promoter and a target gene sequence are joined and positioned in such a way as to permit transcription. Two or more sequences, such as a promoter and any other nucleic acid sequences are operably-associated if transcription commencing in the promoter will produce an RNA transcript of the operably-associated sequences.

A target gene construct useful in the invention may also contain selectable or screenable marker genes for initially isolating, identifying or tracking recombinant cells that contain target gene construct DNA. A reporter gene may also be inserted into the construct such that the growth characteristics of cells containing the target gene construct can be assayed by different means.

Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. In general, expression vectors of utility in recombinant DNA techniques are often in the form of plasmids. However, the invention is intended to include such other forms of expression vectors, such as viral vectors (e.g., replication defective retroviruses, adenoviruses and adeno-associated viruses).

The term "regulatory sequence" is intended to include promoters, enhancers and other expression control elements (e.g., terminators and polyadenylation signals). Such regulatory sequences are described, for example, in Goeddel, Gene Expression Technology: Methods in Enzymology, (1990) Academic Press, San Diego, Calif., p. 185. Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The recombinant expression vectors of the invention can be designed for expression of a polypeptide of the invention in prokaryotic (e.g., E. coli) or eukaryotic cells (e.g., nematode cells, yeast cells or mammalian cells).

Expression of proteins in prokaryotes is most often carried out in E. coli with vectors comprising constitutive or inducible promoters directing the expression of either fusion or non-fusion proteins. Fusion vectors add a number of amino acids to a protein encoded therein, usually to the amino terminus of the recombinant protein. Examples may include but are not limited to pBR322, pASI, pUC7–19, pKK (223-3, 233-2, 177-3, 240-11), pTrc99A-C, pDR540, pDR720, pPL-lambda, pKC30, pSK(+/−), Pin-iii, pCZ198, pTTQ$_{8,9,18,19}$ and 181, pGEMEX-1 and 2, pET1 to pET16 series, pT7-3-7 and the like. Details of exemplary inducible non-fusion E. coli expression vectors can be found in Arnann (pTrc; 1988, Gene 69:301–315) and Studier (pET 11d; 1990, Gene Expression Technology: Methods in Enzymology 185, Academic Press, San Diego, Calif. p. 60–89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21 (DE3) or HMS 174(DE3) from a resident λ prophage harboring a T7 gn1 gene under the transcriptional control of the lacUV 5 promoter.

The most commonly employed, and those generally preferred for use in the present invention, are the trp, lac (or hybrids of these such as the lac UV5 tac and trc promoters), λP$_L$, as well as promoters found in the genes of other E. coli viruses such as T7 or T3. The tac promoter has also proved to be particularly beneficial. The use of a bacterially compatible ribosome binding site is also contemplated especially when an eukaryotic clk-1 polynucleotide is being expressed in bacteria. Generally speaking, it is believed that most known ribosome binding sites, and their associated spacer regions, may be employed to some advantage in connection with this invention. Numerous such ribosome binding sites are known (Gren, 1984, Biochimie, 66:1–29, 1984).

The use of a bacterial transcription terminator is also desirable. In general, it is believed that one may employ virtually any bacterial terminator sequence. Generally speaking, simple bacterial terminators are characterized by a series of thymidine residues at the 3' end of the gene, preceded by a GC-rich region of dyad symmetry in the DNA. Some terminators have a run of adenines (preceding the GC-rich region) that can apparently provide a symmetric counterpart to the uridine-encoding region, and should thus function in both directions. This has been demonstrated for rho indepedant terminators and for the rrnB operon. Terminators seem to be important in the stability of plasmids carrying strong promoters. The terminators which are most frequently used in expression vectors are the trp or the ribosomal terminators, rrnB. Terminator sequences from T7 phage have also been used frequently in expression vectors since they contain RNase III cleavage sites which leave a stem-loop structure at the 3' ends of mRNAs that apparently slows down the degradation of these messages in E. coli.

While the present invention is exemplified through use of a C. elegans clk-1 gene, it is believed that the techniques disclosed herein will be generally applicable to human clk-1 and all other eukaryotic clk-1 polynucleotides, which have similar structural and functional characteristics. Moreover, although the present invention is exemplified in terms of an *E. coli* bacterial host, other types of bacteria can also be employed in place of *E. coli*. Of course, it may be necessary to modify the eukaryotic clk-1 polynucleotide and the expression vector to take into account the considerations of an appropriate ribosomal binding site and effective promoter, but also of the removal of introns and other non-translated sequences for improving bacterial expression of an eukaryotic clk-1 sequence.

In another embodiment, the expression vector is a yeast expression vector. Examples of vectors for expression in yeast *S. cerevisiae* include pYepSec1 (Baldari et al., 1987, EMBO J. 6:229–234), pMFa (Kurjan and Herskowitz, 1982, Cell 30:933–943), pJRY88 (Schultz et al., 1987, Gene 54:113–123), pYES2 (Invitrogen Corp., San Diego, Calif.), and pPicZ (Invitrogen Corp., San Diego, Calif.).

In yet another embodiment, a clk-1 or ubiF nucleic acid of the invention is expressed in mammalian cells using a mammalian expression vector. Examples of mammalian expression vectors include pCDM8 (Seed, 1987, "An LFA-3 cDNA encodes a phospholipid-linked membrane protein homologous to its receptor CD2", Nature. 840–842) and pMT2PC (Kaufman et al., 1987, "Translational efficiency of polycistronic mRNAs and their utilization to express heterologous genes in mammalian cells", EMBO J. 6:187–193). When used in mammalian cells, the expression vector's control functions are often provided by viral regulatory elements. For example, commonly used promoters are derived from polyoma, Adenovirus 2, cytomegalovirus and Simian Virus 40.

In another embodiment, the mammalian expression vector is capable of directing expression of the clk-1 or ubiF nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al., 1987, Genes Dev. 1:268–277), lymphoid-specific promoters (Calame and Eaton, 1988, Adv. Immunol. 43:235–275), in particular promoters of T cell receptors (Winoto and Baltimore, 1989, EMBO J. 8:729–733) and immunoglobulins (Baneiji et al., 1983, Cell 33:729–740; Queen and Baltimore, 1983, Cell 33:741–748), neuron-specific promoters (e.g., the neurofilament promoter; Byrne and Ruddle, 1989, Proc Natl Acad Sci. 86:5473–5477), pancreas-specific promoters (Edlund et al., 1985, Science 230:912–916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss, 1990, Science 249:374–379) and the α-fetoprotein promoter (Campes and Tilghman, 1989, Genes Dev. 3:537–546).

The invention further provides a recombinant expression vector comprising a polynucleotide of the invention cloned into the expression vector in an antisense orientation. That is, the DNA molecule is operably linked to a regulatory sequence in a manner which allows for expression (by transcription of the DNA molecule) of an RNA molecule which is antisense to the mRNA encoding a polypeptide of the invention. Regulatory sequences operably linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid into a host cell, including calcium phosphate or calcium chloride co-precipitation, DEAE-dextran-mediated transfection, lipofection, or electroporation. Suitable methods for transforming or transfecting host cells can be found in laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin and methotrexate. Cells stably transfected with the introduced nucleic acid can be identified by drug selection (e.g., cells that have incorporated the selectable marker gene will survive, while the other cells die).

5.3 Test Cells of the Invention

In the present invention, a target DMQ hydroxylase is produced in a cell for testing with potential drug candidates. Thus, another aspect of the invention pertains to providing test cells for use in the assays of the invention.

As used herein, the term "host cells" refers to prokaryotic or eukaryotic cells that is deficient or has a reduced activity of a native enzyme that converts DMQ to 3-hydroxy Q. Preferably, a host cell has no detectable level of the enzyme activity. The negligble or reduced enzyme activity results in the inability of such host cells to grow normally under certain nutritional or environmental conditions. Alternatively, the negligble or reduced enzyme activity results in a characteristic observable phenotype in the host cells. The host cells are deficient in DMQ hydroxylase activity when they have less enzymatic activity than wild type cells, such as when the host cells exhibit less than 70%, 60%, 50%, 40%, 30%, 20%, 10%, 5%, 2%, 1%, or 0.1% of the wild type level of DMQ hydroxylase activity.

The terms "test cells", "test prokaryotic cells", and "test eukaryotic cells" are used herein to refer to prokaryotic and/or eukaryotic cells used in an assay which comprises a target DMQ hydroxylase, such as a heterologous CLK-1 or UbiF protein, or a functional equivalent thereof. The activity of the target DMQ hydroxylase complements the deficiency of native/endogenous DMQ hydroxylase in the test cells such that the test cells can growth and proliferate in certain nutritional and environmental conditions. The presence of target DMQ hydroxylase activity complements the deficiency and allows the test cells to exhibit under such conditions a growth rate that is about 10%, 20% 30% 40%, 50%, 60%, 70%, 80%, 90%, 100%, 110%, 120%, 150%, 200%, or 250% of that of a wild type cell. When the activity of the target DMQ hydroxylase in the test cells is reduced, such as in the presence of an inhibitor of the target enzyme, the growth characteristics of the test cells under certain nutritional or environmental conditions will be affected and can serve as an indicator of the activity of the target DMQ hydroxylase. The phenotype of such test cells will resemble that of the host cells which is deficient in DMQ hydroxylase. In certain assays, the test cells comprise a copy of the endogenous DMQ hydroxylase gene sequence on the target gene construct. In other assays, the test cells comprise an expressible polynucleotide encoding a variant of a target DMQ hydroxylase or a mutant DMQ hydroxylase. In other assays, such as in control experiments, the test cells comprise only the vector sequences that are used in making a target gene construct.

It is understood that such terms refer not only to the particular subject cell but to the progeny or potential progeny of such a cell. A host cell or test cell can be any prokaryotic (e.g., *E. coli*) or eukaryotic cell (e.g., nematode cells, yeast cells, mammalian cells, mouse cells, or human cells), including transgenic mammalian cells, and embryonic stem cells, and cells in an animal such as a *C. elegans* nematode.

In one embodiment, the present invention relates to uses of host cells that are deficient at the ubiF locus or its equivalent, i.e., cells that have low or zero background DMQ hydroxylase activity. Some of such host cells or strains (also referred to as "host strains") are known in the art. *E. coli* strain JF496 (ubiF411 asnB50::Tn5) is a preferred host strain. These cells lack or produce less DMQ hydroxylase activity which is required for Q biosynthesis. As a result, insufficient quantities of Q are present in the cells to allow the cells to grow and proliferate normally under certain physiological conditions, such as using succinate or glucose as the sole carbon source. The ubiF locus or its equivalent in these cells may either be deleted or mutated to the extent that the gene product is no longer produced or functional. To make a UbiF negative (UbiF⁻) bacterial strain, the ubiF gene or its equivalent in wild type bacteria may be mutagenized or deleted by genetic methods or recombinant DNA techniques, or blocked by antisense oligonucleotides or RNAi techniques well known in the art.

In a related embodiment, the host strain can comprise additional mutations that provide beneficial features to the assays of the invention. The host strain may have a mutation in polyprenyl-diphosphate synthase, the enzyme that controls the polyprenyl side chain length of DMQ, and a rescuing gene construct which comprises an enzyme that produce a polyprenyl side chain of different length. For example, in *E. coli* where there are 8 isoprene groups in the side chain, the enzyme, octaprenyl-diphosphate synthase, is encoded at the ispB locus. In *Rhodobacter capsulatus*, the enzyme, solanesyl-diphosphate synthase, is encoded at the sdsA locus. By such manipulations, DMQ of a specific chain length particular for a target DMQ hydroxylase can be synthesized in the host cells in which the target enzyme will be tested.

To make test cells of the invention, a target gene construct is introduced into host cells. Accordingly, in another embodiment, the invention provides test cells or test cell strains that are deficient in UbiF activity but comprise an expressible genetic sequence encoding a target DMQ hydroxylase.

In a specific embodiment, the test cells are prokaryotic cells, including but not limited to bacterial cells, preferably *E. coli* cells, and most preferably, *E. coli* JP496 cells comprising a target gene construct. In a more specific embodiment, in these prokaryotic test cells, the target gene construct comprises a clk-1 polynucleotide, a polynucleotide encoding a CLK-1, a functionally equivalent thereof, or a mutant thereof, as described in Section 5.1 and 5.2. Preferably, the CLK-1 expressed in the prokaryotic test cells is an eukaryotic CLK-1, including but not limited to a nematode CLK-1, a vertebrate CLK-1, a mammalian CLK-1, a rodent CLK-1, a mouse CLK-1, a primate CLK-1, or a human CLK-1. Preferred examples include *E. coli* JP496 cells comprising pET16-clk-1 (*C. elegans* clk-1), *E. coli* JP496 cells comprising pET16-mclk-1 (mouse clk-1), and *E. coli* JP496 cells comprising pET16-hclk-1 (human clk-1).

In another more specific embodiment, in these prokaryotic test cells, the target gene construct comprises a ubiF polynucleotide, a polynucleotide encoding a UbiF protein, a functionally equivalent thereof, or a mutant thereof, as described in Section 5.1 and 5.2. Preferably, the UbiF expressed in the prokaryotic test cells is a protein that is produced by a pathogen, preferably a bacterial pathogen that infects plants and/or animals, more preferably, a bacterial pathogen that infects vertebrates, mammals, rodents, mice, or primates, and most preferably, a bacterial pathogen that infects humans.

In yet another embodiment, the test cells are eukaryotic cells, including but not limited to nematode cells, vertebrate cells, mammalian cells, rodent cells, mouse cells, primate cells, or human cells. In these eukaryotic test cells, the target gene construct comprises a ubiF polynucleotide, a polynucleotide encoding a UbiF protein, a functionally equivalent thereof, or a mutant thereof, as described in Section 5.1 and 5.2. Preferably, the UbiF expressed in the prokaryotic test cells is a protein that is present in a pathogen, preferably a bacterial pathogen that infects plants and/or animals, more preferably, a bacterial pathogen that infects vertebrates, mammals, rodents, mice, or primates, and most preferably, a bacterial pathogen that infects humans.

In yet another embodiment, the test cells are eukaryotic cells, including but not limited to nematode cells, vertebrate cells, mammalian cells, rodent cells, mouse cells, primate cells, or human cells. In these eukaryotic test cells, the target gene construct comprises a clk-1 polynucleotide, a polynucleotide encoding a CLK-1, a functionally equivalent thereof, or a mutant thereof, as described in Section 5.1 and 5.2. Preferably, the CLK-1 expressed in the prokaryotic test cells is an eukaryotic CLK-1, including but not limited to a nematode CLK-1, a vertebrate CLK-1, a mammalian CLK-1, a rodent CLK-1, a mouse CLK-1, a primate CLK-1, or a human CLK-1.

In yet another embodiment, the test cells comprise a target gene construct comprising a genetic sequence encoding a target DMQ hydroxylase, wherein the genetic sequence is operably linked to an inducible or repressible promoter. The transcriptional activity of such promoters can be regulated positively or negatively by the presence or level of certain chemicals in the test cells.

In various embodiments, a target gene construct of the invention can include any additional genetic sequence, preferably DNA sequence which encodes a detectable gene product (i.e., a peptide or polypeptide). Genetic sequences encoding detectable reporter gene products are well known to those of skill in the art. The reporter gene sequence does not encode necessarily a detectable peptide or polypeptide, since the messenger RNAs of the reporter gene sequence can be detected and quantified.

Polynucleotides encoding DMQ hydroxylases from various prokaryotic or eukaryotic species can be cloned into and expressed in a host cell strain to show complementation of the host cell's CLK-1 or UbiF deficiency. A host cell strain can thus be used to make multiple test strains for experiments with different DMQ hydroxylases. Any UbiF bacterial cells that can express a target DMQ hydroxylation may be used to make test cells of the invention. Bacterial host cells may be obtained from private laboratory deposits, public culture collections such as the American Type Culture Collection, or from commercial suppliers. For example, *Escherichia coli* can be used as a model of many pathogenic bacteria. Genetic sequences encoding target DMQ hydroxylases of various pathogenic species can be expressed in a *E. coli* host cell strain to show complementation of the host cell's UbiF deficiency. Test compounds that specifically inhibit the activity of a target DMQ hydroxylase in *E. coli* test cells are expected to have a similar inhibitory effect on the target DMQ hydroxylase in a pathogenic bacterial species. It is desirable to use bacteria which have been developed for drug screening processes, and that conditions for their growth, maintenance, and manipulations are known. Other preferred bacterial species may include but not limited to *Bacillus subtilis*, and *Pseudomonas aeuroginosa*.

Introduction of the target gene construct into prokaryotic cells may be carried out by conventional techniques well known to those skilled in the art, such as transformation, conjugation, and transduction. For example, where the host is *E. coli*, competent cells which are capable of DNA uptake can be prepared from cells harvested after exponential growth and subsequently treated by the $CaCl_2$ method using procedures well known in the art. Alternatively, $MgCl_2$ or RbCl could be used.

In addition to conventional chemical methods of transformation, a target gene construct of the invention may be introduced into a test cell by physical means, such as by electroporation or microinjection. Electroporation allows transfer of the target gene construct by high voltage electric impulse, which creates pores in the plasma membrane of the host and is performed according to methods well known in the art. Additionally, target gene construct can be introduced into host cells by protoplast fusion, using methods well known in the art.

The test cells which contain the target gene sequence and which express the target DMQ hydroxylase may be identified by at least four general approaches; (a) DNA-DNA or DNA-RNA hybridization; (b) the presence or absence of reporter gene functions (e.g., resistance to antibiotics); (c) assessing the level of transcription as measured by the expression of target DMQ hydroxylase mRNA transcripts in the test cell; and (d) detection of the target DMQ hydroxylase as measured by immunoassay, by its biological activity, or by detecting changes in the level of substrate and product.

The test cells may be cultured under standard conditions of temperature, incubation time, optical density, plating density and media composition corresponding to the nutritional and physiological requirements of the bacteria. However, conditions for maintenance and growth of the test cell may be different from those for assaying candidate test compounds in the screening methods of the invention. Any techniques known in the art may be applied to establish the optimal conditions for growth or for assaying.

Test cell strains, cell cultures, cell lines generated by the above-described methods for the screening assays may be expanded, stored and retrieved by any techniques known in the art that is appropriate to the test cell. For example, the test cells of the invention can be preserved by stab culture, plate culture, or in glycerol suspensions and cryopreserved in a freezer (at −20° C. to −100°C.) or under liquid nitrogen (−176° C. to −196° C.).

The term "reporter gene" as used herein refers to any genetic sequence that is detectable and distinguishable from other genetic sequences present in test cells. Preferably, the reporter gene sequence encodes a protein that is readily detectable either by its presence, or by its activity that results in the generation of a detectable signal. A reporter gene can be used in the invention to monitor and report the DMQ hydroxylase activity or a marker of the activity in test cells.

A reporter gene encodes a reporter molecule which is capable of directly or indirectly generating a detectable signal. Generally, although not necessarily, the reporter gene encodes RNA and detectable protein that are not otherwise produced by the test cells. Many reporter genes have been described, and some are commercially available for the study of gene regulation. See, for example, Alam and Cook, 1990, Anal. Biochem. 188:245–254, the disclosure of which is incorporated herein by reference.

Any antigenic peptide or protein that can be detected by an antibody can be used as a reporter, for example, growth hormone (Selden et al., Mol. Cell Biol., 6:3173). To facilitate detection by antibody binding in immunoassays, antigenic reporter molecules that are secreted or attached on the test cell surface are preferred. For convenience and efficiency, enzymatic reporters and light-emitting reporters are preferred for the screening assays of the invention. Accordingly, the invention encompasses histochemical, colorimetric and fluorometric assays. A variety of enzymes may be used as a reporter which includes but are not limited to β-galactosidase (Nolan et al. 1988, Proc. Natl. Acad. Sci. USA 85:2603–2607), chloramphenicol acetyltransferase (CAT; Gorman et al., 1982, Mol Cell Biol, 2:1044; Prost et al., 1986, Gene 45:107–111), β-lactamase, β-glucuronidase and alkaline phosphatase (Berger et al., 1988, Gene 66:1–10; Cullen et al., 1992, Methods Enzymol; 216:362–368). Transcription of the reporter gene leads to production of the enzyme in test cells. The amount of enzyme present can be measured via its enzymatic action on a substrate resulting in the formation of a detectable reaction product. The methods of the invention provides means for determining the amount of reaction product, wherein the amount of reaction product generated or the remaining amount of substrate is related to the amount of enzyme activity. For some enzymes, such as β-galactosidase, β-glucuronidase and β-lactamase, fluorogenic substrates are available that allow the enzyme to covert such substrates into detectable fluorescent products (see, for example, U.S. Pat. No. 5,070,012, and WO 96/30540).

A commonly used reporter gene is the LacZ gene encoding *E. coli* β-galactosidase. The enzyme is very stable and has a broad specificity so as to allow the use of different chromogenic or fluorogenic substrates, such as but not limited to lactose 2,3,5-triphenyl-2H-tetrazolium (lactose-tetrazolium), 5-bromo-4-chloro-3-indolyl-β-D-galactoside (X-gal), and fluorescein galactopyranoside (Molecular Probes, Org.). See, Nolan et al. 1988, Proc. Natl. Acad. Sci. USA 85:2603–2607. Another commonly used reporter gene is the *E. coli* β-glucuronidase gene (GUS; Gallagher, 1992, in "GUS protocols", Academic Press) which can be used with various histochemical and fluorogenic substrates, such as X-glucuronide, and 4-methylumbelliferyl glucuronide. A variety of bioluminescent, chemiluminescent and fluorescent proteins can also be used as light-emitting reporters in the invention. One type of such reporters, which are enzymes and require cofactor(s) to emit light, include but are not limited to, the bacterial luciferase (luxAB gene product) of *Vibrio harveyi* (Karp, 1989, Biochim. Biophys. Acta 1007:84–90; Stewart et al. 1992, J Gen Microbiol, 138: 1289–1300), and the luciferase from firefly, *Photinus pyralis* (De Wet et al. 1987, Mol. Cell. Biol. 7:725–737). Another type of light-emitting reporter, which does not require substrates or cofactors, includes but are not limited to the wild type green fluorescent protein (GFP) of *Victoria aequoria* (Chalfie et al. 1994, Science 263:802–805), and modified GFPs (Heim et al. 1995, Nature 373:663–4; PCT publication WO 96/23810). Transcription and translation of this type of reporter gene leads to the accumulation of the fluorescent protein in test cells, which can be measured by a device, such as a fluorimeter, or a flow cytometer. Methods for performing assays on fluorescent materials are well known in the art and are described in, e.g., Lackowicz, J. R., 1983, Principles of Fluorescence Spectroscopy, New York:Plenum Press.

Depending on the screening technique and nature of the signal used to assay the reporter gene expression, a reporter regimen can be used to aid directly or indirectly the generation of a detectable signal by a reporter molecule. A reporter regimen comprises compositions that enable and support signal generation by the reporter, such as substrates and cofactors for reporter molecules that are enzymes; e.g., lactose-tetrazolium medium. Such compositions are well known in the art. Components of a reporter regimen may be supplied to the test cells during any step of the screening assay.

5.4 Transgenic Animals

The clk-1 or ubiF polynucleotides can also be used to produce nonhuman transgenic animals. For many non-human animals, a fertilized oocyte or an embryonic stem cell into which a sequence encoding a CLK-1 or UbiF polypeptide has been introduced can be used to create transgenic animals. Such animals are useful for studying the function and/or activity of the heterologous CLK-1 or UbiF polypeptide and for identifying and/or evaluating modulators of enzyme activity. In addition to particular gene expression and/or polypeptide expression phenotypes, the transgenic animals of the invention can exhibit many of the phenotypes (e.g., processes, disorder symptoms and/or disorders), that are known in the art. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, nematodes (such as *C. elegans*) etc. A transgene is exogenous DNA which is integrated into the genome of a cell from which a transgenic animal develops and which remains in the genome of the mature animal, thereby directing the expression of an encoded gene product in one or more cell types or tissues of the transgenic animal. For example, transgenic *C. elegans* can be constructed acccording to Jin Y. (1999) Transformation. In *C. elegans*, A practical approach. (Edited by Oxford University Press) p. 69–95, which is incorporated herein by reference in its entirety.

A transgenic animal of the invention can be created by introducing nucleic acid encoding a CLK-1 or UbiF polypeptide of the invention (or a functionally equivalent thereof) into the male pronuclei of a fertilized oocyte, e.g., by microinjection, retroviral infection, and allowing the oocyte to develop in a pseudopregnant female foster animal. Intronic sequences and polyadenylation signals can also be included in the transgene to increase the efficiency of expression of the transgene. A tissue-specific regulatory sequence(s) can be operably linked to the transgene to direct expression of the polypeptide of the invention to particular cells. Methods for generating transgenic animals via embryo manipulation and microinjection, particularly animals such as mice, have become conventional in the art (see, e.g., U.S. Pat. Nos. 4,736,866; 4,870,009; 4,873,191; Hogan, 1986, Manipulating the Mouse Embryo, Cold Spring Harbor Laboratory Press, Cold Spring Harbor, N.Y.; Wakayama et al., 1999, Proc Natl Acad Sci. 96:14984–14989). Similar methods are used for production of other transgenic animals. A transgenic founder animal can be identified based upon the presence of the transgene in its genome and/or expression of mRNA encoding the transgene in tissues or cells of the animals. A transgenic founder animal can then be used to breed additional animals carrying the transgene. Moreover, transgenic animals carrying the transgene can further be bred to other transgenic animals carrying other transgenes.

To create an homologous recombinant animal, a vector is prepared which comprises at least a portion of a gene encoding a polypeptide of the invention into which a deletion, addition or substitution has been introduced to thereby alter, e.g., functionally disrupt, the gene. In a preferred embodiment, the vector is designed such that, upon homologous recombination, the endogenous gene is functionally disrupted (i.e., no longer encodes a functional protein; also referred to as a "knock out" vector). Alternatively, the vector can be designed such that, upon homologous recombination, the endogenous gene is mutated or otherwise altered but still encodes functional protein (e.g., the upstream regulatory region can be altered to thereby alter the expression of the endogenous protein). In the homologous recombination vector, the altered portion of the gene is flanked at its 5' and 3' ends by additional nucleic acid of the gene to allow for homologous recombination to occur between the exogenous gene carried by the vector and an endogenous gene in an embryonic stem cell. The additional flanking polynucleotides are of sufficient length for successful homologous recombination with the endogenous gene. Typically, several kilobases of flanking DNA (both at the 5' and 3' ends) are included in the vector (See, e.g., Thomas and Capecchi, 1987, Cell 51:503 for a description of homologous recombination vectors). The vector is introduced into an embryonic stem cell line (e.g., by electroporation) and cells in which the introduced gene has homologously recombined with the endogenous gene are selected (See, e.g., Li et al., 1992, Cell 69:915). The selected cells are then injected into a blastocyst of an animal (e.g., a mouse) to form aggregation chimeras (see, e.g., Bradley in Teratocarcinomas and Embryonic Stem Cells: A Practical Approach, Robertson, ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley (1991, Current Opinion in BioTechnology 2:823–829) and in PCT Publication Nos. WO 90/11354, WO 91/01140, WO 92/0968 and WO 93/04169.

In another embodiment, transgenic non-human animals can be produced which contain selected systems which allow for regulated expression of the transgene. One example of such a system is the cre/loxP recombinase system of bacteriophage P1 (see, e.g., Lakso et al., 1992, Proc Natl Acad Sci. 89:6232–6236). Another example of a recombinase system is the FLP recombinase system of *Saccharomyces cerevisiae* (O'Gorman et al., 1991, Science 251:1351–1355. If a cre/loxP recombinase system is used to regulate expression of the transgene, animals comprising transgenes encoding both the Cre recombinase and a selected protein are required. Such animals can be provided through the construction of "double" transgenic animals, e.g., by mating two transgenic animals, one comprising a transgene encoding a selected protein and the other comprising a transgene encoding a recombinase.

Clones of the non-human transgenic animals described herein can also be produced, for example, according to the methods described in Wilmut et al., 1997, Nature 385: 810–813 and PCT Publication Nos. WO 97/07668 and WO 97/07669.

5.5 The Primary Assays

The primary assays of the invention are used to screen initially for compounds that inhibit or activate the activity of a CLK-1 protein or a UbiF protein in test cells. Generally, the screening assays comprise contacting a test compound with test cells for a time sufficient to allow the test compound to cause inhibition or activation of the target protein, and determining the effect in the test cells.

In one embodiment, the primary assays use prokaryotic host cells to screen for compounds that modulate the activity of an eukaryotic target DMQ hydroxylase, such as CLK-1. In another embodiment, the primary assays use prokaryotic host cells to screen for compounds that modulate the activity of a prokaryotic target DMQ hydroxylase, such as UbiF. Detailed description of test cells are provided in Section 5.3 hereinabove.

The test cells provide a source of a target protein characterized by having DMQ hydroxylase, and a cellular environment that has a lower than normal or negligible level of endogenous/background DMQ hydroxylase activity. Because the prokaryotic host cells used to make the test cells are deficient in endogenous DMQ hydroxylase activity, and this endogenous enzyme is essential to cellular metabolism under certain selective nutritional and/or environmental conditions, the host cells cannot grow or grow slowly or poorly under such conditions. In the test cells, the presence of a target protein having DMQ hydroxylase, either a CLK-1 protein or a heterologous UbiF protein, complements the deficiency, and allows the test cells to grow or grow at or near their normal rate, when cultured under selective conditions. Hence, the growth characteristics of the test cells can be used as an indicator of the level of activity of the target protein in the test cells. Although a test compound may modulate the activity of a target protein distinct from DMQ hydroxylation, it is contemplated that the interaction of the test compound and the target protein can affect the DMQ hydroxylase activity of the target protein to an extent which can be detected by the methods of the invention.

In the presence of a test compound which inhibits CLK-1 or UbiF activity, the ability of CLK-1 or UbiF to complement the DMQ hydroxylase deficiency in the test cells is impaired. As a result, an accumulation or increased level of DMQ, and/or a depletion or decreased level of Q is observed or expected in the cells. Accordingly, the invention provides a method for screening for test compounds that modulate the activity of a target protein, such as CLK-1 or UbiF, comprising:

(a) contacting a test cell with a test compound for a time sufficient to allow the test compound to modulate CLK-1 or UbiF activity in the test cell, wherein the test cell comprises a polynucleotide encoding a CLK-1 or UbiF operably linked to a promoter which is expressible in the test cell, and wherein the test cell is deficient in DMQ hydroxylase activity; and (b) detecting a change in CLK-1 or UbiF activity, wherein an increase or decrease in CLK-1 or UbiF activity in the test cell contacted with the test compound relative to the CLK-1 or UbiF activity in a test cell not contacted with the test compound, indicates that the test compound modulates CLK-1 or UbiF activity in the test cell.

Any method known in the art for detecting a change in CLK-1 or UbiF activity, including but not limited to measurements of the levels of intermediates of ubiquinone biosynthesis, such as but not limited to DMQ, Q, and 3-hydroxy ubiquinone including intermediates with different isoprenoid side chains, are applicable in this invention. For example, cell extracts may be subjected to high performance liquid chromatography (HPLC), see section 8.

Depending on whether a test compound has an inhibitory or activating effect on the target protein, a test compound may modulate the ubiquinone level to about 1%, 2%, 5%, 10%, 20% 30% 40%, 50%, 60%, 70%, 80%, 90%, 95%, 105%, 110%, 120%, 125%, 130%, 140%, 150%, 175%, 200%, 250%, 300%, 400%, or 500% of that of test cells without contact with the compound; and in various embodiments, a test compound may modulate the DMQ level to about 1%, 2%, 5%, 10%, 20% 30% 40%, 50%, 60%, 70%, 80%, 90%, 95%, 105%, 110%,120%, 125%, 130%, 140%, 150%, 175%, 200%, 250%, 300%, 400%, or 500% of that of test cells without contact with the test compound.

Without being bound by any theory, the changes in the levels of intermediates in the Q biosynthetic pathway cause a plurality of phenotypic changes in the test cells. One of the most convenient phenotype for determining the activity of a target protein is its DMQ hydroxylase activity which impacts the growth characteristics of the test cells under selective nutritional and/or environmental conditions. Thus, whether a test compound modulates CLK-1 or UbiF activity can be detected by a change in the growth characteristics of the test cells or in the presence of the test compound after the cells have been contacted with the test compound. Accordingly, the invention provides a method for screening for test compounds that modulate a target protein, such as CLK-1 or UbiF, comprising:

(a) contacting a test cell with a test compound for a time sufficient to allow the test compound to modulate CLK-1 or UbiF activity in the test cell, wherein the test cell comprises a polynucleotide encoding a CLK-1 or UbiF operably linked to a promoter which is expressible in the test cell, and wherein the test cell is deficient in DMQ hydroxylase activity; and (b) detecting a change in the number of test cells over a period of time or a change in the growth characteristics of test cells, under selective nutritional and/or environmental conditions, (i) wherein a decrease or stasis in the number of test cells, or a decrease in growth rate of the test cells contacted with the test compound relative to the test cells under the same selective nutritional and/or environmental conditions and not contacted with the test compound, indicates that the test compound inhibits CLK-1 or UbiF activity in the test cell;

or (ii) wherein an increase in the number of test cells or an increase in growth rate of the test cells contacted with the test compound relative to the test cells under the same selective nutritional and/or environmental conditions and not contacted with the test compound, indicates that the test compound activates CLK-1 or UbiF activity in the test cell. In certain embodiments, the target DMQ hydroxylase gene in test cells acts as a selection marker which is necessary for the survival of the test cells when the test cell is grown under the appropriate selection condition. In various embodiments, a test compound may decrease the growth rate to about 0%, 5%, 10%, 20% 30% 40%, 50%, 60%, 70%, 80%, 90%, or 95% of that of test cells without contact with the compound. In various embodiments, a test compound may increase the growth rate to about 105%, 110%, 120%, 125%, 130%, 140%, 150%, 175%, 200%, 250%, 300%, 400%, or 500% of that of test cells without contact with the test compound.

Any technique or combination of techniques known in the art to assess the number of cells or the growth characteristics of cells can be applied in the methods of the invention. Accordingly, the invention further provides that the number or growth rate of the test cells be determined by colony counting, measurements of optical density or light scattering of a liquid culture, dry or wet weight of cells, respiration rates of cells, etc. Alternatively, the number or growth characteristics of the test cells can be assessed by measurements based on a reporter molecule, or signals generated by a reporter molecule.

Selection nutritional conditions that may be used include but are not limited to the availability of a single carbon source in a minimal culture medium. Examples of such media, not by way of limitation, include medium containing glucose or succinate as the sole carbon source in a minimal salt medium. For example, the concentration of such carbon source can range from 0.05% to 5%, preferably 0.1% to 1%, and most preferably at about 0.5%. Since the increase or decrease of enzyme activity may be small, the primary assays are designed to be sensitive enough to detect even small changes in the level of CLK-1 or UbiF activity. The sensitivity of the assay can be enhanced by including a selective environmental condition, such as the presence of oxidative stress. An exemplary source of oxidative stress is hydrogen peroxide, and copper sulfate, such as 5 mM $CuSO_4$, as described by Soballe, B and Poole, R (2000). Microbiology 146: 787–796. Survival of bacteria in the presence of oxidative stress creates further demand for Q which is an anti-oxidant. The stress serves to amplify the differences in phenotypes between cells that may have impaired DMQ hydroxylase activity. For example, and without limitation, about 0.01 mM, 0.1 mM, 0.2 mM, 0.5 mM, 1 mM, 2 mM, 5 mM, or 10 mM hydrogen peroxide may be used in the assay culture medium. The desired concentration of the sole carbon source or oxidative stress can be determined empirically by titrating the growth of the test cell against dilutions of the carbon source or oxidative stress under various growth conditions. Alternatively, a range of concentration of sole carbon source or oxidative stress, such as a dilution series or concentration gradient, may be used in the assay.

In various embodiment, the contacting of the test compounds and cells may be effected in any vehicle and by any means using standard protocols, such as serial dilution, and the use of wells, or disks impregnated with a solution or suspension of a test compound. The amount of time allowed for the test compound to modulate target DMQ hydroxylase activity in the test cells may be determined empirically, such as by running a time course and monitoring the effect of change in target DMQ hydroxylase activity as a function of time. For example, the test cells may be grown in culture to reach a certain phase or optical density, and then the test cells are exposed to a test compound; or alternatively, the test cells may be grown continuously in the presence of a test compound. The culture of test cells may be grown in normal or rich medium up to just before or just after contact with a test compound; or the culture is grown under selective nutritional and/or environmental conditions during the entire period of the assay.

In a preferred embodiment, the invention provides a method for screening for test compounds that inhibit CLK-1 activity comprising:
(a) providing *E. coli* test cells which are deficient in UbiF activity and which comprises an expressible polynucleotide encoding CLK-1 or a functional equivalent thereof;
(b) contacting the *E. coli* test cells with a test compound for a time sufficient to allow the test compound to inhibit CLK-1 activity in the test cells; and
(c) detecting growth of the test cells under the selection condition as described above, wherein a specific decrease in growth of the test cells contacted with the test compound relative to the growth of test cells not contacted with the test compound, indicates that the test compound inhibits CLK-1 activity in the test cells. In more preferred embodiments, the CLK-1 protein expressed in the *E. coli* test cells is a nematode CLK-1, such as *C. elegans* CLK-1, a vertebrate CLK-1, a mammalian CLK-1, a rodent CLK-1, such as mouse CLK-1, a primate CLK-1, or a human CLK-1, or functional equivalents thereof.

In another preferred embodiment, the invention provides a method for screening for test compounds that activates or enhances CLK-1 activity comprising:
(a) providing *E. coli* test cells which are deficient in UbiF activity and which comprises an expressible polynucleotide encoding CLK-1 or a functional equivalent thereof;
(b) contacting the *E. coli* test cells with a test compound for a time sufficient to allow the test compound to activate or enhance CLK-1 activity in the test cells; and
(c) detecting growth of the test cells under the selection condition as described above, wherein an increase in growth of the test cells contacted with the test compound relative to the growth of test cells not contacted with the test compound, indicates that the test compound activates or enhances CLK-1 activity in the test cells. The CLK-1 protein expressed in the *E. coli* test cells can be a nematode CLK-1, such as *C. elegans* CLK-1, a vertebrate CLK-1, a mammalian CLK-1, a rodent CLK-1, such as mouse CLK-1, a primate CLK-1, or a human CLK-1, or functional equivalents thereof. In various embodiments, the CLK-1 protein expressed in the test cells may be a variant that is less active than the wild type CLK-1, such as but not limited to, CDB725 and the likes as provided in Section 7.2.

In yet another preferred embodiment, the invention provides a method for screening for antibiotics or anti-infective compounds that inhibit UbiF activity of a pathogen comprising:
(a) providing *E. coli* test cells which are deficient in *E. coli* UbiF activity and which comprises an expressible polynucleotide encoding a UbiF protein of a pathogen, or a functional equivalent thereof;
(b) contacting the *E. coli* test cells with a test compound for a time sufficient to allow the test compound to inhibit the UbiF activity in the test cells; and
(c) detecting growth of the test cells under the selection condition as described above, wherein a specific decrease in growth of the test cells contacted with the test compound relative to the growth of test cells not contacted with the test compound, indicates that the test compound inhibits UbiF activity in the test cells. In more preferred embodiments, the UbiF protein expressed in the *E. coli* test cells is a bacterial UbiF.

In another embodiment, the primary assays uses eukaryotic host cells to test compounds that modulate the activity of an eukaryotic target DMQ hydroxylase, such as a heterologous CLK-1. In yet another embodiment, the primary assays uses eukaryotic host cells to test compounds that modulate the activity of a prokaryotic target DMQ hydroxylase, such as UbiF. Detailed description of test cells are provided in Section 5.3 hereinabove.

The eukaryotic test cells of the invention provide a source of the target DMQ hydroxylase, and preferably, a cellular environment that has a lower than normal or negligible level of endogenous/background DMQ hydroxylase activity. As described above, Q is an antioxidant, and an important cofactor in cellular metabolism. Hence, many cellular phenotypes sensitive to changes in oxidative stress levels and the growth characteristics of the test cells can be used as an indicator of the level of DMQ hydroxylase activity in the test cells. Preferably, the test cell is deficient in DMQ hydroxylase activity.

In the presence of a test compound which modulates CLK-1 or UbiF activity, an accumulation or increased level of DMQ, and/or a depletion or decreased level of Q is the result in the eukaryotic test cells. Accordingly, the invention provides a method for screening for test compounds that modulate a target DMQ hydroxylase, such as CLK-1 or UbiF, comprising:

(a) contacting a eukaryotic test cell with a test compound for a time sufficient to allow the test compound to modulate CLK-1 or UbiF activity in the test cell, wherein the test cell comprises a polynucleotide encoding a CLK-1 or UbiF operably linked to a promoter which is expressible in the eukaryotic test cell; and (b) detecting a change in CLK-1 or UbiF activity, wherein an increase or decrease in CLK-1 or UbiF activity in the test cell contacted with the test compound relative to the CLK-1 or UbiF activity in a test cell not contacted with the test compound, indicates that the test compound modulates CLK-1 or UbiF activity in the test cell.

Any method known in the art for detecting a change in CLK-1 or UbiF activity, including but not limited to measurements of the levels of intermediates of ubiquinone biosynthesis, such as but not limited to DMQ, Q, and 3-hydroxy ubiquinone is applicable in this invention.

In a preferred embodiment, the invention provides a method for testing antibiotics or anti-infective compounds that inhibit UbiF activity of a pathogen comprising:

(a) providing mammalian test cells which have lower than normal or negligible DMQ hydroxylase activity and which comprises an expressible polynucleotide encoding a UbiF protein of a pathogen, or a functional equivalent thereof;

(b) contacting the test cells with a test compound for a time sufficient to allow the test compound to inhibit the UbiF activity in the test cells; and (c) detecting survival or growth of the test cells, wherein a decrease in the number of test cells or a decrease in the growth of the test cells contacted with the test compound relative to the growth of test cells not contacted with the test compound, indicates that the test compound inhibits UbiF activity in the test cells. In various embodiments, the mammalian test cells can be cultured under selective conditions, such as the presence of oxidative stress. In more specific embodiments, instead of detecting survival or changes in growth rates, a cellular phenotype that reflects DMQ hydroxylase activity can be observed. In various embodiments, the UbiF protein expressed in the test cells is a bacterial UbiF.

For clarity of discussion, the invention is described in the example sections below by way of example of *E. coli*. However, the principles may be applied to other prokaryotic or eukaryotic test cells which are deficient in a protein functionally equivalent to CLK-1 or UbiF.

5.6 Secondary Assays

In another embodiment, the invention provides secondary assays that are preferably used to further characterize the positive compounds identified in the primary assays. The secondary assays described in the following sections can be used in combination with each other, and can employ any of the techniques described above to determine cell number, cell density, metabolic activities, presence and/or amount of reporter molecules, signals generated by reporter molecules, and the levels of intermediates of ubiquinone biosynthesis. This embodiment of the invention is described below by way of example of UbiF-deficient *E. coli* cells comprising a CLK-1 expression construct. However, the principles may be applied to other prokaryotic or eukaryotic test cells and other target CLK-1 or UbiF.

In one embodiment, the invention provides an assay that determines whether a test compound which scored positive in a primary assay for an inhibitor acts specifically against a target DMQ hydroxylase. The assay uses a test cell which is deficient in DMQ hydroxylase activity and comprises either a blank expression vector, or a target gene construct comprising a polynucleptide encoding an inactive target DMQ hydroxylase. The method comprises (a) contacting a test cell with the test compound for a time sufficient to allow the test compound to enter the test cell; (b) adding ubiquinone or a synthetic mimic (such as $Q_1$) to the cells; and (c) detecting a change in the number of test cells over a period of time or a change in the growth characteristics of test cells under selective nutritional and/or environmental conditions, (i) wherein an increase or stasis in the number of test cells over a period of time or an increase in growth rate of the test cells contacted with the test compound relative to the test cells under the same selective nutritional and/or environmental conditions and not contacted with the test compound, indicates that the test compound is a potential CLK-1 or UbiF inhibitor in the test cell; or (ii) wherein a decrease in the number of test cells, or a decrease in growth rate of the test cells contacted with the test compound relative to the test cells under the same selective nutritional and/or environmental conditions and not contacted with the test compound, indicates that the test compound does not act on the target DMQ hydroxylase, or acts non-specifically, or is generally toxic to the test cell. In preferred embodiments, the test cells are *E. coli* cells deficient in UbiF activity and comprise an expression vector without an inserted polynucleotide, such as JF496+pET16; and the selective conditions are M9-LB medium without hydrogen peroxide.

In another embodiment, the invention provides an assay that determines whether a test compound which scored positive in a primary assay for an inhibitor acts against a specific target DMQ hydroxylase. The assay uses a test cell which is deficient in DMQ hydroxylase activity and comprises a target gene construct comprising a polynucleotide encoding an alternative DMQ hydroxylase. The method comprises (a) contacting a test cell with the test compound for a time sufficient to allow the test compound to enter the test cell; and (b) detecting a change in the number of test cells over a period of time or a change in the growth characteristics of test cells under selective nutritional and/or environmental conditions, (i) wherein an increase or stasis in the number of test cells over a period of time or an increase in growth rate of the test cells contacted with the test compound relative to the test cells under the same selective nutritional and/or environmental conditions and not contacted with the test compound, indicates that the test compound is an inhibitor specific to the target DMQ hydroxylase in the test cell; or (ii) wherein a decrease in the number of test cells, or a decrease in growth rate of the test cells contacted with the test compound relative to the test cells under the same selective nutritional and/or environmental conditions and not contacted with the test compound, indicates that the test compound does not act specifically on the target DMQ hydroxylase, and is likely targeting a mechanism common to both the target DMQ hydroxylase and the alternative DMQ hydroxylase. In preferred embodiments, the test cells are $E.$ $coli$ cells deficient in UbiF activity and comprise an expression vector containing a polynucleotide encoding the $E.$ $coli$ UbiF, such as JF496+ubiF.

In yet another embodiment, the invention provides assays that characterize the interactions of a test compound which scored positive in a primary assay with a target DMQ hydroxylase. The assays use test cells which are deficient in DMQ hydroxylase activity and comprises a target gene construct comprising a polynucleotide encoding a functional fragment or variant of the target DMQ hydroxylase. The method comprises (a) contacting a test cell with the test compound for a time sufficient to allow the test compound to enter the test cell; and (b) detecting a change in the number of test cells over a period of time or a change in the growth characteristics of test cells under selective nutritional and/or environmental conditions, (i) wherein an increase or stasis in the number of test cells over a period of time or an increase in growth rate of the test cells contacted with the test compound relative to the test cells under the same selective nutritional and/or environmental conditions and not contacted with the test compound, indicates that the interaction involves a portion of or certain amino acid residues on the target DMQ hydroxylase which is not present in the test cells; or (ii) wherein a decrease in the number of test cells, or a decrease in growth rate of the test cells contacted with the test compound relative to the test cells under the same selective nutritional and/or environmental conditions and not contacted with the test compound, indicates that the test compound interacts with the fragment or variant of the target DMQ hydroxylase in the test cell. In preferred embodiments, the test cells are $E.$ $coli$ cells deficient in UbiF activity and comprise an expression vector containing a polynucleotide encoding functional variants of $C.$ $elegans$ CLK-1 which complemented the DMQ hydroxylase deficiency in the cells. Examples of such variants are described in Section 7.2.

In yet another embodiment, inhibitors of ubiF gene expression or UbiF enzyme activity of a given pathogen can be tested on JF496 bacteria transformed with ubiF from other pathogens and which show UbiF enzyme activity. Growth inhibition is tested on a minimal medium containing succinate or glucose as a carbon source. This cross-inhibition study distinguishes ubiF gene expression inhibitors and UbiF enzyme activity inhibitors that are truly specific to a given pathogen, from ubiF gene expression inhibitors and UbiF enzyme activity inhibitors that are able to target two or more ubiF gene products, and thus represent potential broad-spectrum antibiotics. Each inhibitor of ubiF gene expression or UbiF enzyme activity of a given pathogen is also tested on the corresponding bacterial pathogen from which the ubiF gene was obtained in order to rank the inhibitors according to their capacity of slowing down the growth of the pathogen.

In yet another embodiment, a plurality of ubiF gene from selected human bacterial pathogens is expressed in $C.$ $elegans$ transgenic lines. A DNA sequence encoding a mitochondrial targeting sequence is cloned in frame with the ubiF gene for proper targeting to mitochondria, under the control of clk-1 promoter. For example, the CLK-1 mitochondria import sequence is discussed in Jiang et al. 2001, J Biol Chem 276, pp. 29218–25, and the general mechanism in Voos et al., 1999, Biochim Biophys Acta, 1422:235–54. Many mitochondrial import sequences are known and software programs have been used to identify such sequences in mammalian proteins: see MitoProt, Claros et al., Eur. J. Biochem. 241, 779–786 (1996) and Psort II (Horton and Nakai, Intellig. Syst. Mol. Biol. 5, 147–152 (1997).

First the activity of the ubiF variants in clk-1(qm30) is evaluated. The effect of ubiF on the phenotypes displayed by clk-1(qm30), such as slow growth, slow adult behaviours, and sterility when growing on Q-deficient bacteria is measured. Then the effects of a given ubiF gene expression inhibitor or UbiF enzyme activity inhibitor on worms transformed with ubiF and showing UbiF enzyme activity is evaluated, and compared to clk-1(qm30) mutants. The compounds that only affect those worms that express the ubiF gene, but not the non-transgenic ones (i.e., no detrimental effects on the non-transgenic worms) are selected.

General techniques and methodology for performing in vivo assays using the nematode worm $Caenorhabditis$ $elegans$ ($C.$ $elegans$) as a model organism have been described in the art, such as but not limited to Rand and Johnson, Chapter 8, Vol. 84 "$Caenorhabditis$ $elegans$: Modern Biological Analysis of An Organism", Ed. Epstein and Shakes, Academic Press, 1995, WO 98/51351, WO99/37770, WO 00/34438, WO/00/01846, WO 00/63427, WO 00/63425, WO 00/63426, WO 01/88532, and WO 01/94627, each of which is incorporated herein by reference in its entirety. As described in these applications, one of the main advantages of assays involving the use of $C.$ $elegans$ is that such assays can be carried out in multi-well plate format (with each well usually containing a sample of between 1 and 100 nematodes).

Generally, in the assays described below, the nematodes are incubated in suitable vessel or compartment, such as a well of a multi-well plate, on a suitable medium which may be a solid, semi-solid, viscous or liquid medium, with liquid and viscous media usually being preferred for assays in multi-well plate format. The medium is also seeded with bacteria which serves as food for the nematodes. In assays, where the nematodes are contacted with one or more test compounds, the compound can be added to the medium on or in which the nematodes grow, or the nematodes can be soaked in a solution containing the compound for various time intervals. After a suitable incubation time (i.e., sufficient for the compound to have its effect, if any, on the nematodes), the nematodes are then subjected to detection or measurement by visual inspection or by one or more techniques appropriate to the phenotype of interest. Since the nematodes can move around in the medium, the nematodes may optionally be killed or paralyzed prior to the analysis; this additional step may be used to keep the distribution of nematodes in the compartment or well uniform for signal detection. A change in the phenotype as compared to a control not contacted with the test compound is an indication of the influence of the compound on the nematode. Many of the manipulations can be automated such as by using suitable robotics and high throughput assay technologies known in the art. Preferably, in automated assays, techniques involving a non-visual detection method, such as measurement of fluorescence or nucleic acid hybridization can be used.

In yet another embodiment, a plurality of ubiF gene from selected human bacterial pathogens is expressed in transgenic mice, of a wild-type or a clk-1 −/− background. A DNA sequence encoding a mitochondrial targeting sequence is cloned in frame with the ubiF gene (for proper targeting in the mitochondria), under the control of any appropriate promoter. First, the activity of the ubiF variants in mice is evaluated. Then, the effects of a given ubiF gene expression inhibitor or UbiF enzyme activity inhibitor on mice expressing ubiF is evaluated and compared to non-transgenic animals. The compounds that only affect those mice that express the ubiF gene, and not the non-transgenic ones (i.e., no detrimental effects on the non-transgenic mice) are selected.

In yet another embodiment, a heterologous clk-1 gene including hclk-1, is expressed under the control of the clk-1 promoter or any other appropriate promoter, in *C. elegans* transgenic lines. First, the activity of the clk-1 variants, including hclk-1 in clk-1(qm30) are evaluated. The effect of clk-1 on the phenotypes displayed by clk-1(qm30), such as slow growth, slow adult behaviours, and sterility when growing on Q-deficient bacteria is measured. Then, the effects of a given clk-1 gene expression inhibitor or CLK-1 enzyme activity inhibitor on worms expressing clk-1 is evaluated and compared to clk-1(qm30) mutants. The compounds that only affect those worms that express the clk-1 gene, and that are not otherwise toxic to worms (i.e., no detrimental effects on the worms) are selected.

In yet another embodiment, a heterlogous clk-1 gene including hclk-1, is expressed in transgenic mice under the control of an appropriate promoter. Transgenic mice are generated in the wild-type and in the clk-1 −/− background. First, the activity of the clk-1 variants, including hclk-1, in mice is evaluated. Then, the effects of a given clk-1 gene expression inhibitor or CLK-1 enzyme activity inhibitor on transgenic mice expressing clk-1 is evaluated and compared to non-transgenic mice. The compounds that only affect those mice that express the clk-1 gene, and not non-transgenic ones and are otherwise not toxic to mice (i.e., no detrimental effects on the non-transgenic mice) are selected.

In various embodiments, the clk-1 and CLK-1 inhibitors found in the primary screens can be assayed in relevant in vivo disease models such as models of disease due to oxidative stress and free-radical damage, including but not exclusively, models of cancer, atherosclerosis, diabetes, Parkinson's disease, ischemia, and models in which free-radical detoxifying enzymes are non-functional. The assay includes examining the delay of disease onset and development. The effects of the clk-1 gene expression inhibitors and CLK-1 enzyme activity inhibitors in relevant cellular models can also be assayed, including by evaluating the effect of these clk-1 and CLK-1 inhibitors on proliferation of cells derived from tumors.

A test compound that scored positive in both primary and secondary assays can be a lead compound for further development. As it is well known that toxicity does not always arise from the same mechanism of action as is responsible for growth inhibition in the targeted microorganism; therefore, the selectivity of the target should not be assessed solely on the basis of the results of the above described secondary assays. Cytotoxity can be measured by methods known in the art. One such method is based on assessing growth of mammalian cells in the presence of the test compound. The assay measures the metabolic reduction by viable cells, of colorless XTT tetrazolium to yield orange XTT formazan, which is measurable by conventional colorimetric techniques (Weislow et al. 1989, J. Natl. Cancer Inst., 81:577–586; which is incorporated by reference in its entirety).

In yet another embodiment, relating to antibiotics candidates, the minimum inhibitory concentration (MIC) against bacterial organisms is determined for each compound that is positive in both the primary assays and secondary assays. Methods known in the art may be used such as broth microdilution testing, using a range of concentrations of each test compound (1993, National Committee for Clinical Laboratory Standards, Methods for Dilution Antimicrobial Susceptibility Tests For Bacteria That Grow Aerobically—Third Edition: Approved Standard, M7-A3, which is incorporated by reference herein in its entirety). The MIC against a variety of pathogens are determined using the same method. Pathogenic species to be tested generally include, but are not limited to: *E. coli, Enterococcus faecium, Enterococcus faecalis, Streptococcus pneumoniae, Staphylococcus aureus, Klebsiella pneumoniae, Pseudomonas aeruginosa, Staphylococcus epidermis, Shigella flexneri*, and *Salmonella typhimurium*.

5.7 Kits

In another embodiment, the present invention provides a kit for screening for compounds that modulate activity of an enzyme capable of carrying out DMQ hydroxylation. The kit can comprise one or more aliquots of test cells which are deficient in endogenous DMQ hydroxylation and comprises a target DMQ hydroxylase. Preferably, the target DMQ hydroxylase complements the activity of the endogenous DMQ hydroxylase. The kit comprises one or more aliquots of an *E. coli* strain comprising a mutation that impairs UbiF function and a DNA sequence encoding for a eukaryotic CLK-1; or an *E. coli* strain comprising a mutation that impairs UbiF function and a DNA sequence encoding for UbiF of a pathogen.

Optionally, the kit comprises instructions on using the test cells in screening methods. Optionally, the kit comprises host cells which lack the target DMQ hydroxylase, gene expression constructs comprising a clk-1 polynucleotide, a ubiF polynucleotide, or a polynucleotide encoding a target DMQ hydroxylase, positive control compounds, such as but not limited to anti-CLK-1 antibodies, or anti-UbiF antibodies, etc. Optionally, the kit can also comprise cell growth media, agents for setting up selective condition (e.g., hydrogen peroxide), reagents (e.g., ubiquinone analogs), and devices for measuring cell growth, respiration rates; and reagents and devices for detecting reporter molecules or signal generated by reporter molecules.

5.8 Compounds Identified by Methods of the Invention

In another aspect, by practice of the methods of the invention, novel therapeutic compounds are discovered. The primary screening assays can be used to screen chemical compound libraries at high-throughput. Such libraries contain single compounds, mixtures of compounds with known structures, and natural product extracts. Mixtures of compounds can be deconvoluted to identify the active compound. The active component(s) in natural product extracts that test positive in the assay can be separated and identified.

In one embodiment, compounds that inhibit an eukaryotic DMQ hydroxylase, such as human CLK-1, can be useful for treating diseases and clinical conditions caused in part by or exacerbated by oxidative stress and/or free radical damage, such as but not limited to cancer, cardiovascular diseases (atherosclerosis, reperfusion ischemia), diabetic complications, obesity, and dyslipidemia. In another embodiment, compounds that activate an eukaryotic DMQ hydroxylase, such as human CLK-1, can be useful for treating diseases or clinical conditions associated with low ubiqunone levels, such as but not limited to Friedreich's ataxia, Parkinson's disease. In yet another embodiment, compounds that inhibit a prokaryotic DMQ hydroxylase, such as a UbiF or its equivalent in pathogens, can be useful for treating infectious diseases.

The compounds used in the screen can be a derivative of any compound involved in electron transport in membranes, or in oxidative stress modulation. The compounds can be obtained from random or focused combinatorial libraries, or Q and/or DMQ analogs generated by chemical modifications. The compounds can be antibodies to CLK-1 or UbiF, and derivatives thereof; or polynulceotides, such as but not limited to antisense oligonucleotides or RNAi molecules. Antibodies against murine CLK-1 and *C. elegans* CLK-1 have been described in Jiang et al. (2001) J. Biol Chem 276: 29218–29225, and Hihi et al. (2003 J. Biol Chem 278: 41013–41018, respectively; antibodies against *C. elegans CLK*-1 are also commercially available from Santa Cruz Biotechnology (cat# sc-9255 and sc-9256, Santa Cruz, Calif.). The compounds can also be derived from natural products. The hits found in the screen will serve as leads in chemistry approaches to generate better inhibitors or activators, using the same criteria as previously mentioned.

By "effective amount" is meant an amount of a compound that relieves (to some extent) one or more symptoms of the disease or condition in the subject. Additionally, by "effective amount" is meant an amount that returns to normal, either partially or completely, physiological or biochemical parameters associated with or causative of a disease or condition.

5.8.1 Inhibitors of CLK-1

The present invention encompasses methods for decreasing production of reactive oxygen species (ROS). The inhibitors can be useful in the context of diseases where excess ROS is a causative agent in triggering the disease and in disease progression. Examples of such diseases or clinical conditions include but are not limited to atherosclerosis, ischemia, vascular complications of diabetes, cancer, and obesity.

In one embodiment, inhibitors of CLK-1 such as compounds identified by the methods of the invention can be used in the treatment of atherosclerosis, ischemia, vascular complications of diabetes, cancer, and obesity. In a related embodiment, the present invention relates to uses of CLK-1 inhibitors for the prevention of and/or a patient's self-management of atherosclerosis, ischemia, vascular complications of diabetes, cancer, and obesity.

CLK-1 inhibitors can be used to treat and prevent atherosclerosis and to modulate the development and progression of atherosclerotic lesions. Oxidative stress has been shown to play an important role in the inflammation of the vessel wall as well as synthesis of oxidized low density lipoprotein (LDL) which triggers formation of foam cells. A detailed explanation of the mechanisms of atherosclerosis where ROS is implicated as a causative agent is provided in Lusis (2000, Nature, 407:233–241), and Steinberg (2002, Nat Med 8:1211–7), which are incorporated herein by reference in their entireties.

CLK-1 inhibitors can also be used to treat ischemia and in particular, to mitigate or prevent hypoxia-reoxygenation injuries to cells and tissues. Many such injuries that are known to be mediated in part by ROS occur during or after circulatory shock, myocardial ischemia, hepatic ischemia, intestinal ischemia, cerebral ischemia, renal ischemia, stroke, or transplantation of organs. A detailed description of ROS-mediated reoxygenation injuries is found in Li (2002, Am J Physiol Cell Ohysiol 282:C227–41).

CLK-1 inhibitors can also be used to treat and/or prevent vascular complications of diabetes. ROS is involved in four pathways that lead to hyperglycaemia-induced damage: increased polyol pathway flux, increased advanced glycation end-product formation, activation of protein kinase C, and increased hexosamine pathway. CLK-1 inhibitors can be used to simultaneously prevent the activation of any of these four pathways.

In cancer, multiple mutations are present which suggest that they are not generated suddenly by a single event, but instead are generated early and accumulate continuously during tumor progression. Endogenous cellular processes may damage DNA and serve as a source of mutations that initiate tumorigenesis and that produce multiple mutations during tumor progression, particularly in the presence of diminished DNA repair.

As in the case of DNA damage by environmental chemicals, damage by endogenous processes would need to occur at a sufficiently high frequency to exceed the capacity of the cell for DNA repair. Based on variations in populations, approximately 50% of human cancer deaths have been shown to be associated with environmental agents (predominantly smoking). However, for a number of major sporadic human cancers the age-specific incidence does not vary extensively in different populations and thus, may be the result of normal endogenous cellular processes. Amongst these cancers are carcinomas of the pancreas, ovary and colon.

A number of human cancers arise on a history of prolonged inflammation; in fact, chronic inflammatory diseases may be a primary factor in the development of up to one-third of all cancers. Chronic infections that elicit an inflammatory response are potent generators of ROS. Neutrophils produce oxygen bursts of superoxide radical and hydrogen peroxide, which can subsequently interact via the Haber-Weiss reaction to form the potent hydroxyl radical. Phagocytes recruited to the site of chronic infection abundantly generate reactive oxidants, such as nitric oxide and hypochlorite to inactivate the bacteria. However, these reactive oxidants can cause damage to host cells and DNA, as well as the invading bacterium, and this chronic damage can contribute to the development of a tumor.

ROS may also play a critical role in the pathogenesis of viral infections. Viral infection may activate phagocytic cells to release ROS and pro-oxidant cytokines, and may affect the pro-oxidant/antioxidant balance in host cells, including inhibition of antioxidant enzymes, such as superoxide dismutase. Finally, ROS may mediate release of the host cell nuclear transcription factor-B from the inhibitory Ik-B protein, and result in increased viral replication. Gastritis, chronic hepatitis, ulcerative colitis and pancreatitis are among those conditions associated with chronic inflammation and a high incidence of associated malignancies.

Accordingly, CLK-1 inhibitors can be used to treat, prevent, and/or manage cancer. In particular, CLK-1 inhibitors can be used to modulate the development and proliferation of pre-cancerous cells. Cancer describes a disease state in which a healthy cells are transformed into abnormal cells, which is followed by an invasion of adjacent tissues by these abnormal cells, and which may be followed by lymphatic or blood-borne spread of these abnormal cells to regional lymph nodes and/or distant sites, i.e., metastasis. Abnormal cell regulation may lead to tumor growth such that the tissue mass is increased because of greater cell numbers as a result of faster cell division and/or slower rates of cell death. The invention contemplates uses of CLK-1 inhibitors to reduce the incidence of ROS-mediated damage to DNA in cells, to halt the accumulation of mutations in DNA of cells, to inhibit the growth and spread of pre-cancerous and cancer cells, to slow the transformation of normal or pre-cancerous cells to malignancy, to slow the spread of metastases, to lessen or reduce the number of pre-cancerous and/or cancer cells in the body, or to ameliorate or alleviate the symptoms of cancer.

CLK-1 inhibitors can also be used to treat obesity, and to treat or prevent obesity-associated metabolic complications. Fat accumulation has pleiotropic effects on the energy balance of a subject. Medical complications due to excess fat include dyslipidemia (high lipid concentrations in the serum), insulin resistance, hyperglycemia, and hypertension. Overall, the occurrence of these disorders in obese patients is also known as the metabolic syndrome or syndrome X, as reviewed by Desvergne, Michalik and Wahli (Apr. 15 2004, Molecular Endocrinology, "Be fit or be sick: PPARs are down the road").

A medical study conducted by Urakawa et al. (2003, J Clin Endocrinol Metab, 88:4673–4676) investigated the relationship of oxidative stress with obesity and insulin resistance in men. PGF2α, which is indicative of oxidative stress, was measured in obese patients and compared to non-obese ones in relation to insulin resistance. The results indicate that obesity contributes to oxidative stress, and that oxidative stress triggers the development of insulin resistance. CLK-1 inhibitor can be used to diminish oxidative stress, and alleviate the onset of complications linked to a high oxidative status and obesity.

Neurodegenerative diseases such as but not limited to Alzheimer's disease (AD), and amyotrophic lateral sclerosis (ALS), are characterized by progressive loss of specific neuronal cell populations and are associated with protein aggregates. A common feature of these diseases is extensive evidence of oxidative stress, which might be responsible for the dysfunction or death of neuronal cells that contributes to disease pathogenesis. See review by Bainham et al., 2004, Nature Reviews Drug Discovery, 3: 205–14. Apparently, high oxygen consumption, relatively low antioxidant levels and low regenerative capacity result in brain tissue being susceptible to oxidative damage. It is contemplated that CLK-1 inhibitors can be used to reduce ROS production in the brain, thereby preventing or slowing the degeneration of neuronal cells and tissues.

In a related embodiment of the invention, an inhibitor of CLK-1 (such as but not limited to small organic compounds, natural products, anti-CLK-1 antibodies or derivatives thereof, antisense polynucleotides) is administered to a subject who has symptoms of atherosclerosis, dyslipidemia, ischemia, stroke, diabetes, abnormal cell proliferation, cancer, and obesity, or a subject who is diagnosed with these disease or medical conditions. A CLK-1 inhibitor can be administered to a subject who is about to undergo or has undergone organ transplantation or surgery. A CLK-1 inhibitor can also be administered to a subject who is prone to or predisposed to these disease or medical conditions, usually as a result of genetic factors and/or environmental factors, such as but not limited to exposure to carcinogens, radiation, source of ROS or free radicals; high caloric or fat intake; and smoking. The invention also includes novel pharmaceutical compositions which comprise compounds discovered as described above formulated in pharmaceutically acceptable formulations. The compound(s) can also be administered adjunctively with other therapeutic agents used for treatment and/or prevention of these diseases or medical conditions.

5.8.2 Activators of CLK-1

Compounds identified by the methods of the invention that activates or enhances the activity of CLK-1 are capable of causing higher ubiquinone synthesis in a subject. These agents can be used in diseases where ubiquinone supplementation is used as a treatment, such as in Friedreich's ataxia (Rustin et al. (1999) Lancet 354: 477–479), where subjects are treated with a synthetic ubiquinone, idebenone. These agents can also be useful in diseases where a subject's ubiquinone levels are low, and where supplementation can be beneficial, e.g., Parkinson disease (See Shults et al. (2002) Arch Neurol. 59: 1541–1550).

Parkinson's Disease (PD) affects 1% of the population over the age of 55 and leads to motor symptoms, such as tremor, rigidity and bradykinesia (slowness of movement) when about 80% of the substantia nigra is degenerated. Besides the appearance of Lewis bodies, filamentous, cytoplasmic inclusions with alpha-synuclein as a major protein component, oxidative stress and mitochondrial dysfunction have been strongly associated with PD pathogenesis. Thus, brains of PD patients demonstrate oxidative stress-related changes, such as damage to DNA, lipids, and proteins. In addition, tyrosine hydroxylase and monoamine oxidase generate ROS as by products during their activity in dopamine metabolism. These events are comprehensively reviewed by Betarbet et al (2002, Bioassays 24:308–318).

Six out of eight models for Parkinson's disease are based on the induction of oxidative stress by exposure to methamphetamine, 6-hydroxydopamine, 1-methyl-4-phenyl-1,2,3,6-tetrahydropryridine, paraquat, rotenone, and 3-nitrotyrosine. Induction of PD, characterized by a substantial degeneration of striatal dopaminergic terminals associated with reactive gliosis can occur as fast as after 5 days treatment with 5 mg/kg, i.p. of methamphetamine injected three times, every 2 hr. CLK-1 activators can be tested in such models for alleviation of PD symptoms.

In a related embodiment, the invention features a method for treating a subject with Parkinson's disease or symptoms of Parkinson's disease by administering to that subject a effective amount of a compound which increases ubiquinone level. Preferably, te compound acts by activating or enhancing the activity of CLK-1. The invention also includes novel pharmaceutical compositions which comprise therapeutic agents discovered as described above formulated in pharmaceutically acceptable formulations. The therapeutic agent can also be administered adjunctively with ubiquinone or its synthetic equivalents.

5.8.3 Antibiotics

Antibiotic compounds identified by the methods of the invention are capable of causing DMQ hydroxylase inhibition in a pathogen, leading to a reduction or inhibition of its growth. Preferably, these compounds are expected to be effective against a variety of species of bacteria, including infectious pathogenic bacteria. The invention also includes novel pharmaceutical compositions which comprise antibiotic compounds discovered as described above formulated in pharmaceutically acceptable formulations.

In a related embodiment, the invention features a method for treating a subject infected with an infectious agent by administering to that subject a therapeutically effective amount of an antibiotic compound which causes DMQ hydroxylase inhibition, preferably specific inhibition in the infectious agent as determined by the assays of the invention. Such administration can be by any method known to those skilled in the art, for example, by topical application or by systemic administration. The antibiotic compounds identified by the methods of the infection can be used to treat infectious diseases in animals, including humans, companion animals (e.g., dogs and cats), livestock animals (e.g., sheep, cattle, goats, pigs, and horses), laboratory animals (e.g., mice, rats, and rabbits), and captive or wild animals.

Specifically, infectious diseases caused by bacteria including but not limited to, gram positive cocci, such as Staphylococci (e.g., *S. aureus*), Streptococci (e.g., *S. pneumoniae, S. pyrogens, S. faecalis, S. viridans*); gram positive bacilli, such as Bacillus (e.g., *B. anthracis*), Corynebacterium (e.g., *C. diphtheriae*), Listeria (e.g., *L. monocytogenes*); gram negative cocci, such as Neisseria (e.g., *N. gonorrhoeae, N. Meningitidis*); gram negative bacilli, such as Haemophilus (e.g. *H. influenzae*), Pasteurella (e.g., *P. multocida*), Proteus (e.g., *P. mirabilis*), Salmonella (e.g., *S. typhi murium*), Shigella (e.g. *Shigella flexneri*), Escherichia (e.g., *E. coli* O157:H7), Klebsiella (e.g., *K. pneumoniae*), Serratia (e.g. *S. marcescens*), Yersinia (e.g., *Y. pestis*), Providencia species, Enterobacter species, Bacteroides (e.g., *fragilis*), Acinetobacter species, Campylobacter (e.g., *C. jejuni*), Pseudomonas (e.g., *P. aeruginosa*), Bordetella (e.g., *B. pertussis*), Brucella species, Fracisella (e.g., *F. tularensis*), Clostridia (e.g., *C. perfriugens*), Helicobacter (e.g., *H. pylori*), Vibrio (e.g., *V. cholerae*), Mycoplasma (e.g., *M. pneumoniae*), Legionella (e.g., *L. pneumophila*), Spirochetes (e.g. *Treponema, Leptospira* and *Borrelia*), Mycobacteria (e.g., *M. tuberculosis*), Nocardia (e.g., *N. asteroides*), Chlamydia (e.g., *C. trachomatis*), and Rickettsia species, can be treated by antibiotic drugs discovered by the methods of the invention.

In yet another embodiment, antibiotic compounds of the present invention can be used to treat contaminated items, such as crops, wood, metal or plastic and the like, by methods such as, but not limited to, spraying or dusting of that agent onto the contaminated item, or impregnating that compound into the item.

5.8.4 Formulation and Administration

The compounds identified by methods of the invention may be formulated into pharmaceutical preparations for administration to subjects for treatment of a variety of infectious diseases. Thus, the compounds and their physiologically acceptable solvates may be formulated for administration by inhalation or insufflation (either through the mouth or the nose) or oral, buccal, parenteral, topical, dermal, vaginal, rectal administration and drug delivery device, e.g., porous or viscous material, such as lipofoam.

Preparations for oral administration may be suitably formulated to give controlled release of the active compound. For buccal administration, the compositions may take the form of tablets or lozenges formulated in conventional manner. The compounds may be formulated for parenteral administration by injection, e.g., by bolus injection or continuous infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The pharmaceutical compositions of the present invention comprise a therapeutic compound as the active ingredient, or a pharmaceutically acceptable salt thereof, and may also contain a pharmaceutically acceptable carrier, and optionally, other therapeutic ingredients. The term "pharmaceutically acceptable salts" refers to salts prepared from pharmaceutically acceptable non-toxic acids and bases, including inorganic and organic acids and bases.

For administration to subjects, compounds discovered by using the assays of the invention are formulated in pharmaceutically acceptable compositions. The compositions can be used alone or in combination with one another, or in combination with other therapeutic or diagnostic agents. These compositions can be utilized in vivo, ordinarily in a mammal, preferably in a human, or in vitro. In employing them in vivo, the compositions can be administered to the mammal in a variety of ways, including parenterally, intravenously, subcutaneously, intramuscularly, colonially, rectally, vaginally, nasally, orally, transdermally, topically, ocularly, or intraperitoneally.

As will be readily apparent to one skilled in the art, the magnitude of a therapeutic dose of a compound in the acute or chronic management of a disease will vary with the severity of the condition to be treated, the particular composition employed, and the route of administration. The dose, and perhaps dose frequency, will also vary according to the species of the animal, the age, body weight, condition and response of the individual subject. The determination of effective dosage levels, that is the dosage levels necessary to achieve the desired result, will be within the ambit of one skilled in the art.

Optionally, for treatment of an infectious disease, a second antibacterial compound may be used in combination with the antibiotic compound identified by the method of the invention. The second antibacterial compound may be naturally occurring or synthetic. Suitable naturally occuring antibacterial compounds include, but are not limited to, aminoglycosides (including but not limited to dihydrostreptomycin, gentamycin, kanamycin, neomycin, paromycin and streptomycin); amphenicols (including but not limited to chloramphenicol); ansamycins (including but not limited to rifamycin); b-lactams such as carbapems (including but not limited to imipenem), cephalosporins (including but not limited to cefazedone and cefroxadine), cephamycins (including but not limited to cefbuperazone); monobactams (including but not limited to aztreonam), oxacephems (including but not limited to flomoxef) or penicillins (including but not limited to ampicillin, carbencillin, methicillin, penicillin N, penicillin O and penicillin V); lincosamides (including but not limited to clindamycin and lincomycin); macrolides (including but not limited to carbomycin and erythromycin); polypeptides (including but not limited to gramicidin S and vancomycin); tetracyclines (including but not limited to apicycline, methacycline and tetracycline); and others such as cycloserine, mupirocin and tuberin. Suitable synthetic antibacterial compounds include 2,4-diaminopyrimidines (including but not limited to trimethoprim); nitrofurans (including but not limited to nifuradene); quinolones and quinolone analogs (including but not limited to enoxacin, lomefloxacin, nalidixic acid and ofloxacin); sulfonamides (including but not limited to sulfamoxole and sulfanilamide); sulfones (including but not limited to diathymosulfone); oxazolidinones (including but not limited to linezolid); and others such as glycylcycines, clofoctol, hexedine, methenamine, and nitroxoline. A potential combination could be with antibiotics to which ubiquinone-deficient bacteria are resistant, such as aminoglycosides including phleomycin, as described by Collis and Grigg (1989) J Bacteriol. 171: 4792–4798 (test whether exposing bacteria to phleomycin induces resistance to our test cpds)

The "adjunct administration" of a compound identified by the method of the invention and a second compound means that the two are administered either as a mixture or sequentially. When administered sequentially, the compound may be administered before or after the second compound, so long as the initially administered compound is still providing the desired therapeutic activity. Any of the above described modes of administration can be used in combination to deliver the compound and the second compound. When a compound identified by the method of the invention and a second compound are administered adjunctively as a mixture, they are preferably given in the form of a pharmaceutical composition comprising both agents. Thus, in a further embodiment of the invention, it is provided a pharmaceutical composition comprising a compound identified by the method of the invention and a second compound together with a pharmaceutically acceptable carrier.

6. EXAMPLES

The JF496 System

The invention may be better understood by the following description of illustrative examples which are not intended to be limiting.

JF496 is useful for complementation assays using eukaryotic clk-1. As with all other ubi mutants, JF496 has a weak growth in liquid culture, and cannot use succinate as a unique carbon source. These characteristics were used to develop a gain-of-function assay, where JF496 was transformed with a eukaryotic clk-1 (here from *C. elegans*) and then wild-type growth was identified. Transgenic *E. coli* ubiF (Kwon et al., 2000 *FEMS Microbiol Lett*, 186, 157–161), and clk-1 from proteobacteria (Stenmark et al., 2001 *J Biol Chem*, 276, 33297–33300) have been tested in JF496.

Sequencing UbiF411 (SEQ ID NO:1, FIG. 3) of an *E. coli* ubiF mutant, JF496 (ubiF411) shows that the ubiF411 allele has a point mutant at nucleotide 488 compared to the sequence of wildtype ubiF (SEQ ID NO:2, FIG. 4) changing a GGT codon to a GAT codon and results in an amino acid substitution in UbiF, G163D, (delineated by the brackets in FIG. 5; SEQ ID NO:3 and SEQ ID NO:4, respectively) in the monooxygenase domain. This mutation alters the enzymatic activity of the UbiF protein

6.1 Materials and Methods

Bacterial strains—JF496 (ubiF411) is provided by the *E. coli* stock center at Yale University; BL21 (DE3) is from Novagen (San Diego, Calif.).

Site-directed mutagenesis—pET-16b vector (Novagen) containing *C. elegans* clk-1 is used to generate point mutants. Mutagenesis is executed with the "Quickchange® site-directed mutagenesis kit" (Stratagen®). The primers (BioCorp Inc.) used to introduce the E147A/E148A mutation described herein are SHP2224 (CACAAGATTA CGTGATGCGG CGCTTCATCA TCATGATAC, SEQ ID NO:5), and SHP2225 (GTATCATGAT GATGAAGCTC CTCATCACGT AATCTTGTG SEQ ID NO:6). TOP10 *E. coli* (Invitrogen) is used for transformation. Purification of plasmid DNA is made with the "Qiaprep® spin miniprep kit" (Qiagen). Mutagenesis is verified by sequencing (Mobix Lab). Primers SHP1511 (GGCATATGTT CCGTGTAATA ACCCGTGGAG C, SEQ ID NO:7), SHP1513 (GGCATATGGG AAAAGAAGGT GCAATGGC, SEQ ID NO:8) and SHP1514 (GGGGATCCTC AAATTTTCTC AGCAATCGCA ATAGC, SEQ ID NO:9) are used to confirm the validity of the clones (when tested, at least 2 out of 3 clones were positive).

Growth conditions—For complementation assays, plasmids are freshly transformed by electroporation into *E. coli* JF496 ubiF(DE3) and grown overnight at 37° C. in 5 mL LB with 50 μg/mL ampicillin. The cultures are diluted 1/10 and $OD_{600}$ measured. A bacterial volume corresponding to an $OD_{600}$ of 0.03 in 5 mL is taken, centrifuged and resuspended in 100 μl of M9 medium. It is then added into 5 mL M9 containing 1 mM $MgSO_4$, 20 μM $CaCl_2$, 0.5 μg/mL thiamine, 0.12% casamino acids, 40 μg/mL D-L-methionine, 100 μg/mL L-asparagine, trace metals and 50 μg/mL ampicillin. This medium is supplemented with 0.5% glucose or 0.5% succinate. *E. coli* JF496 is grown at 37° C. for 8 hours. Samples (700-μL) are taken at 2-hour intervals and the $OD_{600}$ is measured in order to determine the growth rate.

Immunoblot analysis—First, the amount of bacterial culture that is sufficient to produce a signal in immunoblotting is determined. A bacterial pellet is washed with $ddH_2O$ and resuspended with SDS sample buffer supplemented with 100 mM DTT and 50 ng/μL DNAseI. For the next step, a 12.5 μL bacterial sample is mixed to 12.5 μL SDS sample buffer (Bio-Rad) supplemented with 100 mM DTT and heated 5 min at 85° C. Proteins are resolved using SDS-PAGE (12% resolving gel and a 4.5% stacking gel). Benchmark™ prestained protein marker (Invitrogen) are used as molecular weight standards. After electrophoresis (90–100 V/3 h 30 min), the proteins are transferred onto a nitrocellulose membrane (Trans-Blot® Transfer Medium, Bio-Rad) as described in the user's guide (70 V/1 h 25 min). Immunoblot analysis is performed as described in the Novagen guide. Detection is performed with the His-Tag® monoclonal antibody (1:1000, Novagen). Goat anti-mouse HRP conjugated (Novagen) is used as secondary antibody (1:5000). The ECL Western blotting detection reagents (Amersham Biosciences) are used for the detection procedure.

6.2 Exemplary Screening Procedures

Transform JF496 (or an equivalent *E. coli*, or any other bacteria deficient in UbiF activity) with a ubiF, a homolog of ubiF, a functional mutant of ubiF, an enzymatically functional fragment of ubiF, an enzymatically functional fragment of a homolog of ubiF, or an enzymatically functional fragment of a functional mutant of ubiF from bacteria, including from human pathogens. Collectively, these test cells are referred to as JF496-ubiF.

Transform JF496 (or an equivalent *E. coli*, or any other bacteria deficient in UbiF activity) with a clk-1, a homolog of clk-1, a functional mutant of clk-1, an enzymatically functional fragment of clk-1, an enzymatically functional fragment of a homolog of clk-1, or an enzymatically functional fragment of a functional mutant of clk-1 from eukaryotes, including from humans or other mammals. Collectively, these test cells are referred to JF496-clk-1.

Grow in parallel JF496-ubiF and JF496-clk-1 in liquid culture, using a minimal growth medium containing succinate as a unique carbon source. These two strains are able to develop on succinate-containing medium because each of UbiF or CLK-1, respectively, is active, allows Q production, and sustains growth on a non-fermentable carbon source such as succinate. In addition, grow in parallel JF496-ubiF and JF496-clk-1 in liquid culture, using a minimal growth medium containing succinate as a unique carbon source supplemented with ubiquinone ($Q_1$). Growth is monitored for a maximum of 8 hours, and evaluated by a spectrophotometrical read out at 600 nm, or any other procedure that allows to follow bacterial growth.

Any compound that inhibits JF496-clk-1 growth but not JF496-ubiF growth is a clk-1- or CLK-1-specific inhibitor. This class of compounds are not generally toxic to *E. coli* because they do not interfere with JF496-ubiF growth.

Any compound that inhibits JF496-ubiF growth but not JF496-clk-1 growth is a ubiF- or UbiF-specific inhibitor. This class of compounds are not generally toxic to *E. coli* because they do not interfere with JF496-clk-1 growth. ubiF- or UbiF-specific inhibitors will specifically act on bacteria and inhibit their growth. These inhibitors can be developed as antibiotics.

Any compound that inhibits JF496-ubiF growth as well as of JF496-clk-1 growth, but not JF496 growth on a minimal growth medium containing succinate as a unique carbon source supplemented with ubiquinone ($Q_1$) is a DMQ-hydroxylation-specific inhibitor. This class of compounds are not generally toxic to *E. coli* because they do not interfere with the growth of J-P496 supplemented with $Q_1$. This class of compounds targets a common feature of UbiF and CLK-1 important for DMQ hydroxylation, including the active site of the enzyme.

6.3 Results

Figure 1:
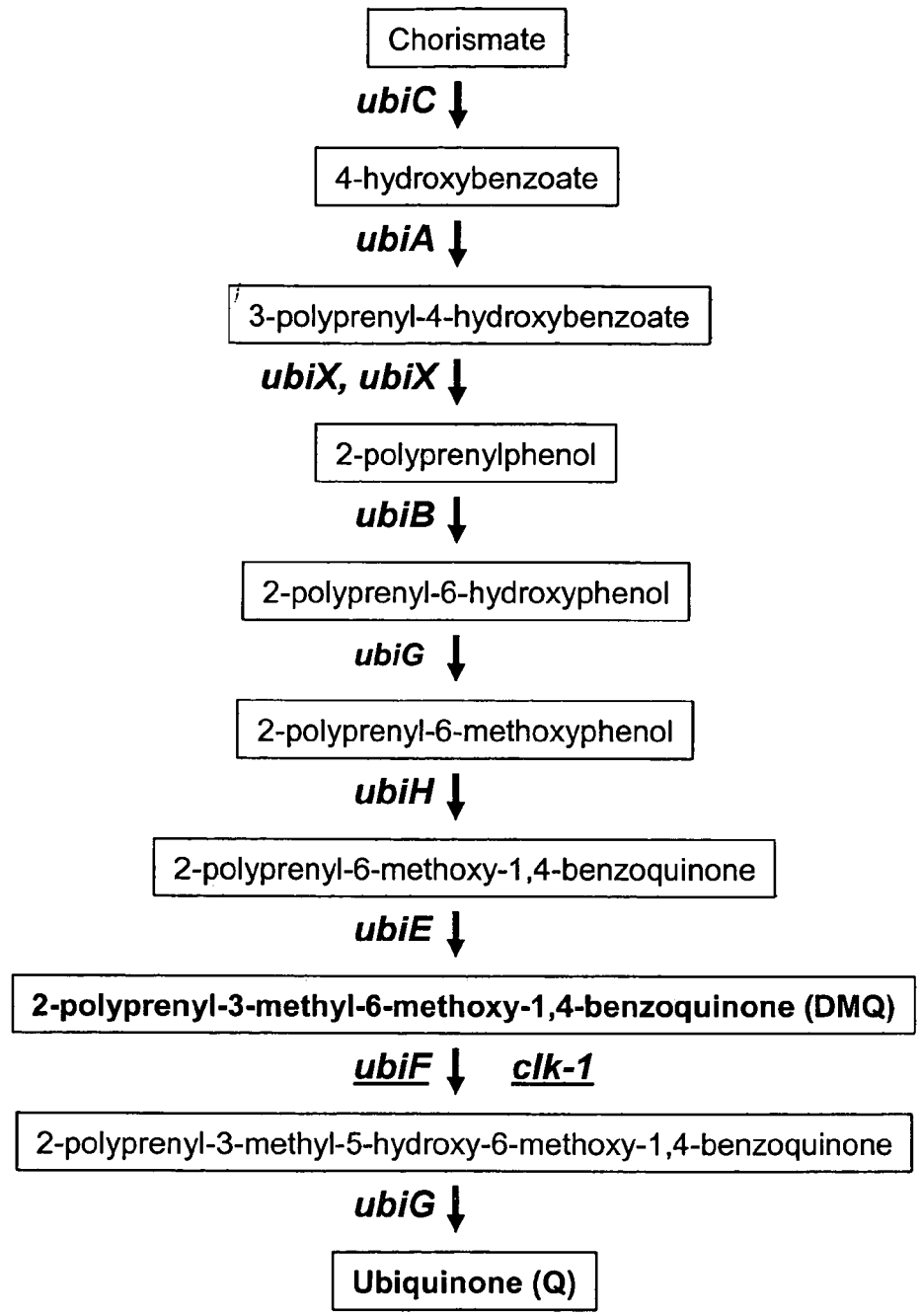
FIG. 1 illustrates the nine steps of the Q biosynthesis pathway.
Figure 2:
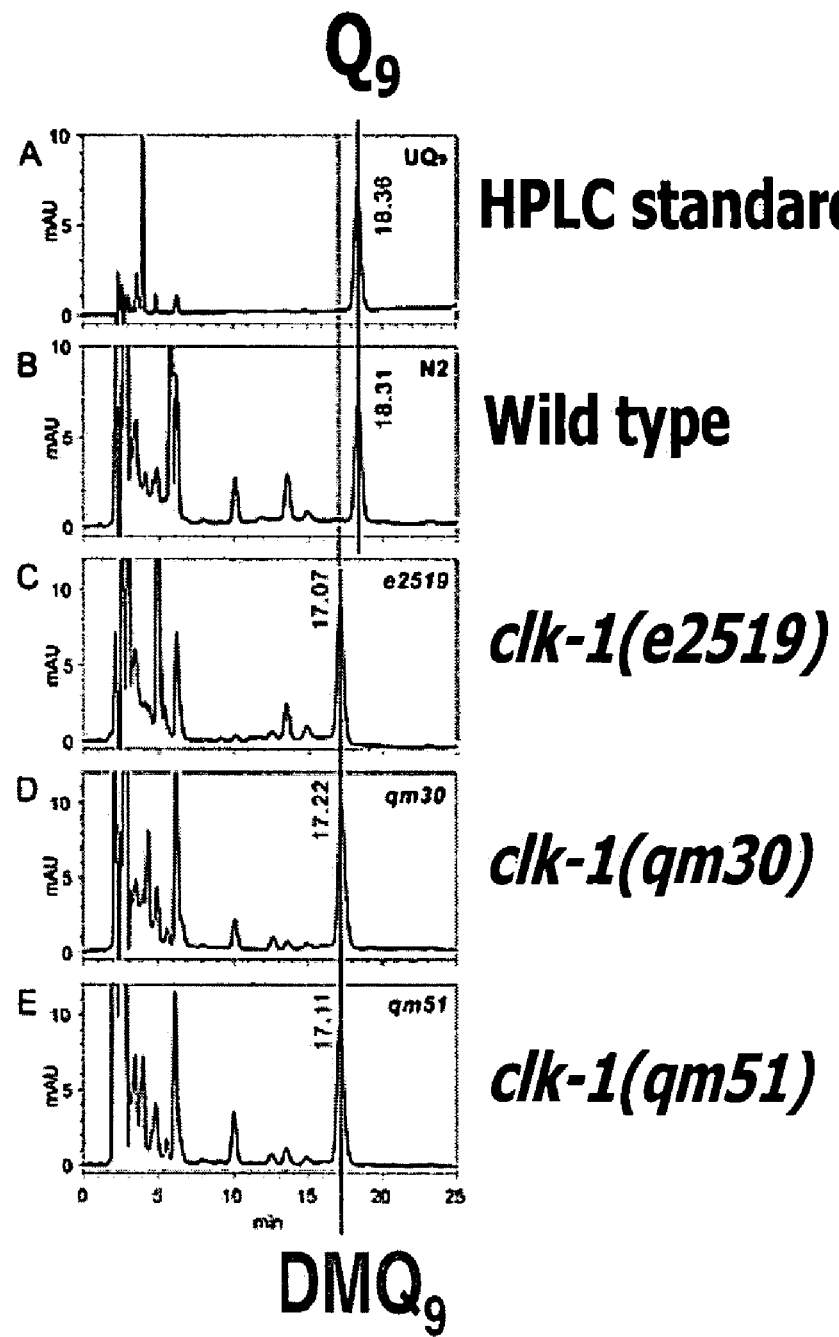
FIG. 2 illustrates an HPLC analysis showing that *C. elegans* clk-1 mutants accumulate DMQ.
Figure 6:
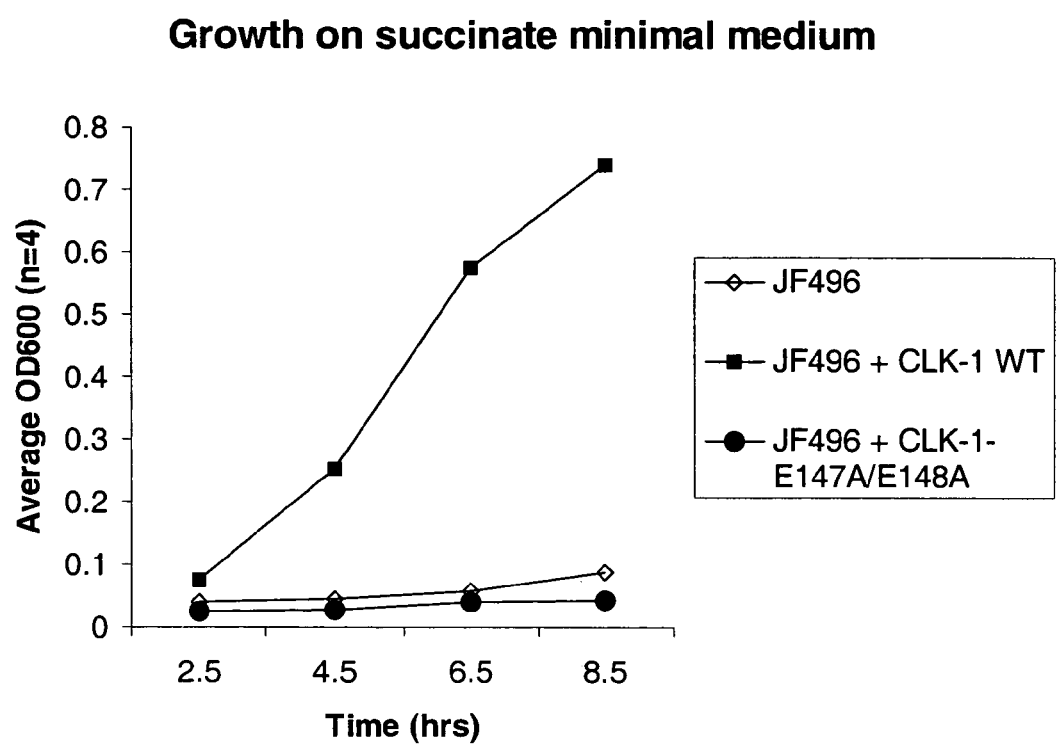
FIG. 6 illustrates the dependency of *C. elegans* clk-1 rescue of JF496 on a functional iron binding consensus sequence.
Figure 7:
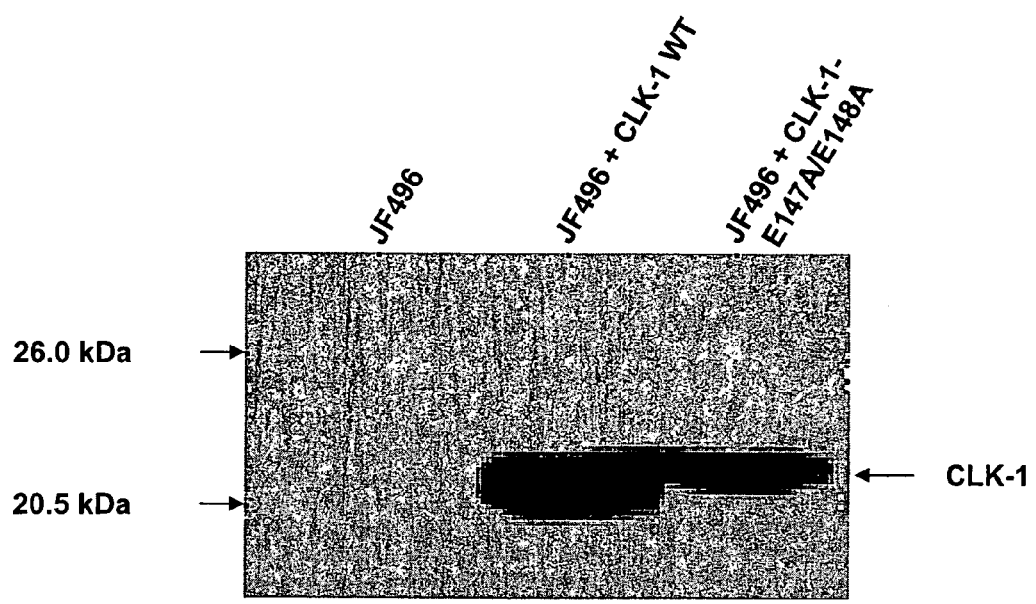
FIG. 7 illustrates CLK-1 protein levels in transformed JF496.

It was found that the *C. elegans* clk-1 is able to rescue the JF496 growth defect, which proves that a eukaryotic clk-1 is able to express a functional enzyme in prokaryotes and replace the function of the endogenous ubiF (FIG. 6). This rescuing activity is dependent upon a functional CLK-1, as a double mutant version of clk-1 (E147A/E148A) in the putative iron-binding site of CLK-1 cannot rescue JF496 (FIG. 6), even when a full-length protein is expressed in the transformed bacteria. FIG. 7 shows an immunoblot analysis of protein extracts derived from JF496 expressing either CLK-1 (wt), or CLK-1 (E147A/E148A) which shows the presence of CLK-1 in both cases. Thus, the failure of CLK-1 (E147A/E148A) to rescue JF496 is due to a loss of function and not to a lack of expression in the transformed bacteria.

7. STRUCTURE AND FUNCTION ANALYSIS OF CLK-1

The JF496 system was used for studying the structure and function of *C. elegans* CLK-1 variants. The system was also used to demonstrate that recombinant mammalian CLK-1 proteins are able to complement the function of UbiF in *E. coli*.

7.1 Materials and Methods

Bacterial strains—JF496 (ubiF411); BL21(DE3).
Expression vectors—pET16b vector (Novagen) was used to express the different clk-1 variants, *E. coli* ubiF is cloned in pET101-Topo (Invitrogen), which is based on pET16, and allows Topo cloning.

pET16-*C. elegans* clk-1; pET16-mouse clk-1.
pET16-human clk-1 was constructed as follows: hclk-1 cDNA was obtained from Invitrogen, and was PCR amplified using SHP2468 and SHP 2469 primers. The PCR fragment was subcloned in pCDNA3.1-V5-His-Topo (Invitrogen). hclk-1 was then subcloned in pET16b, as a NdeI/BamHI fragment.

pET101 *E.coli* ubiF was constructed as follows: ubiF was amplified using SHP 2756 and SHP 1955, and was introduced in pET101 by Topo cloning.

Site-directed mutagenesis—pET-16b vector (Novagen) containing *C. elegans* clk-1 is used to generate point mutants. Mutagenesis was conducted with the "Quick-change® site-directed mutagenesis kit" (Stratagene®). The primers were obtained from BioCorp Inc. TOP10 *E. coli* (Invitrogen) is used for transformation. Purification of plasmid DNA was made with the "Qiaprep® spin miniprep kit" (Qiagen). Mutagenesis was verified by DNA sequencing (Mobix Lab). Primers SHP 1511, SHP 1513 and SHP 1514 were used to confirm the validity of the clones.

Growth conditions—as described above in Section 6.1

7.2 Results

C. Elegans CLK-1 Variants

A selection of CLK-1 variants were constructed by site-directed mutagenesis and cloned into the JF496 system to assess their enzymatic activity relative to the wild type. The respective strains of JF496-clk-1 variants were cultured as described and the growth rate of each were measured. The results as shown in Table 4 indicate that certain residues and regions are not tolerant of amino acid substitution (amino acid substitution is indicated by one-letter codes).

TABLE 4

Activity of *C. elegans* CLK-1 variants in JF496 system

| Clone designation | Mutation | Activity in JF496 system |
| --- | --- | --- |
| CDB 720 | E30A | Inactive |
| CDB 721 | Y37A | Active |
| CDB 718 | E60A | Inactive |
| CDB 719 | H63A | Inactive |
| CDB 716 | H118A | Inactive |
| CDB 717 | Y119A | Inactive |
| CDB 707 | E147A | Active |
| CDB 691 | E147K | Active |
| CDB 699 | E148A | Inactive |
| CDB 694 | E148K | Inactive |
| CDB 708 | E147A/E148A | Inactive |
| CDB 714 | H150A | Active |
| CDB 715 | H151A | Inactive |
| CDB 709 | Q174A | Active |
| CDB 698 | I115H | Inactive |
| CDB 711 | S51P | Active |
| CDB 710 | Y90G | Active |
| CDB 689 | C107A | Active |
| CDB 690 | C177A | Active |
| CDB 700 | C107A/C177A | Active |
| CDB 728 | E112A | Inactive |
| CDB 723 | E148K/L149N | Inactive |
| CDB 724 | E62L | Active |
| CDB 725 | E147A/H151Q | Partially active |
| CDB 726 | G32D | Inactive |

7.3 Results

Mammalian CLK-1

FIG. 8 shows that the expression of mouse clk-1 cDNA (mclk-1) in JF496 rescues bacterial growth under selective condition. The experiment shown was performed in M9 buffer containing 0.5% glucose. The expression of mclk-1 cDNA was capable to sustain growth of the JF496-mclk-1 clone in this medium. In comparison, growth of the control bacteria comprising the vector pET16 was very slow. This indicates that a mammalian CLK-1 can function in bacteria and functionally replace ubiF activity.

FIG. 9 shows that the expression of human clk-1 cDNA (hclk-1) in JF496 rescues bacterial growth under selective condition. The experiment shown was performed in M9 buffer containing 0.5% glucose. The expression of hclk-1 cDNA was capable to sustain growth of the JF496-hclk-1 clone in this medium. In comparison, growth of the control bacteria comprising the vector pET16 was very slow. This indicates that a second mammalian CLK-1 can function in bacteria and functionally replace ubiF activity. The results also indicate that the rescuing capacity of hclk-1 is lower than that of mclk-1 or *C. elegans* clk-1.

Overall, the results obtained with mammalian CLK-1 proteins validate the inventors' approach of using a prokaryotic cell system, such as *E. coli* and especially JF496, for drug screening. This approach allows direct testing of the drug target of a subject or a myodel animal, and does not involve a surrogate such as a nematode orthologue in the assay.

Contrary results obtained with yeast orthologues of clk-1, also known as coq7, apparently suggested that eukaryotic clk-1 may not be able to complement the UbiF deficiency in *E. coli*. Both *Saccharomyces pombe* coq7 (Berthold et al. 2003, Protein Sci., 12: 124–134) and *Saccharomyces cerevisiae* cannot complement the UbiF-deficiency in JF496 bacteria. The results presented here indicate that other eukaryotic CLK-1 proteins, such as mammalian CLK-1, can complement the UbiF deficiency and allow the testing of these CLK-1 in a UbiF-deficient prokaryotic cell.

7.4 Results

Prokaryotic UBI F

FIG. 10 shows that the expression of *E. coli* UbiF in JF496 rescued bacterial growth under selective condition. The JF496-ubiF was cultured in M9 buffer containing 0.5% glucose. The expression of *E. coli* UbiF from a plasmid was capable to reconstitute the Q biosynthetic pathway in JF496. In comparison, growth of the control bacteria comprising the vector pET16 was very slow. The JF496-ubiF cells can be used in secondary assays to determine the specificity of the activity of a test compound.

The results also indicates that a prokaryotic UbiF, such as those from prokaryotic pathogens, can be introduced into JF496 to complement its deficient ubiF activity. Such JF496-ubiF(pathogen) cells can be used to screen for antibiotics against pathogens.

8 HIGH THROUGHPUT SCREENING ASSAY

The rationale of the screening methods of the invention is illustrated by the JF496 system which comprise *C. elegans* clk-1, mouse clk-1 or human clk-1. To take advantage of the convenience and economy of using bacterial cells, the effects of test compounds are investigated initially in JF496-clk-1 cells. CLK-1 inhibitors are identified by their effect on the ability of a target CLK-1 to complement for the growth of JF496-clk-1 cells in the presence of limited carbon source and hydrogen peroxide. Positive compounds are then tested in a secondary toxicity assay to identify those that act independently of CLK-1. Specificity against CLK-1 can be further tested using another test cell strain comprising a UbiF protein using the same format and conditions. Compounds identified as specific inhibitors of CLK-1 in these bacterial screens are further screened for their ability to inhibit endogenous CLK-1 in mammalian cell lines as described in Section 9.

8.1 Materials

Bacteria were diluted from an overnight preculture in to M9-LB (50:50; v:v) to an $OD_{600}$ of 0.03. The M9-LB medium contained 1 mM hydrogen peroxide. 1% DMSO was added to the positive control. A volume of 100–200 ul of JF496-pET16-mclk-1 ($OD_{600}$=0.03) was distributed in 80 wells of flat-bottom 96-well plates (columns 2 to 11). Negative control consisted of JF496-pET16, and JF496-mclk-1 served as positive control. A compound was deposited in each of the wells containing bacteria. Compounds dispensing takes place in a fume hood. Plates were incubated at 37° C. for 6 hours with or without shaking. $OD_{570}$ was measured after shaking for 5 seconds in the plate reader (AD340, Beckman).

Test compounds were thawed from −80° C. at room temperature for 4 hours and stored at 4° C. for the period of screening (approximately 1 month). Bacteria and compounds are distributed in wells with multichannel pipettes (Eppendorf). These procedures are adapted to use a multidrop 96/384 (Titertek) for bacteria dispensing, and a Biomek FX (Beckman) for compound dispensing.

8.2 Screening Method

The screening steps were carried out according to the following protocol:
1. Grow JF496+pET16-clk-1 strain overnight
2. Dilute the strain at a final $OD_{600}$ of 0.03
3. Dispense the diluted bacteria in 96-well plates using an appropriate volume (100–200 μL, for example)
4. Add the test compounds at an appropriate concentration (50–100 μM, for example)
5. Grow the bacteria for about 6 hours (other time periods can be used).
6. Evaluate growth using an optical density readout.
7. Select compounds with a consistent inhibition activity
8. Re-test the selected compounds using the same format.

Compounds with an inhibitory activity can be further investigated using a number of counter screens. This step is preferred since the growth inhibition assay can identify false positive compounds which is toxic or which have a detrimental effect on growth that is independent of CLK-1 activity.

Two counter screens can be performed as follows:
1. Toxicity Assay

This assay uses the JF496+pET16 strain, which corresponds to the non-complemented mutant bacterial strain. Using this strain allows observation on growth in the absence of CLK-1 (M9-LB medium without hydrogen peroxide). 100 mM $Q_1$, which is a synthetic ubiquinone, is added to the growth media, which mimics the presence of ubiquinone that is absent from JF496 or JF496+pET16. The results are interpreted as follows:

Any compound that inhibits growth does so independently of CLK-1 activity, and can be ruled out as a CLK-1 inhibitor.

Any compound that does not inhibit growth of JF496+ pET16 is a potential CLK-1 inhibitor.

2. UbiF/CLK-1 Specificity

This assay uses the JF-496+ubiF strain which is complemented by the UbiF activity expressed from a plasmid can be grown in the presence of hydrogen peroxide. Compounds that inhibit bacterial growth in the presence of CLK-1 are selected to be tested in this setting. The results are interpreted as follows:

Any compound that inhibits CLK-1 but not UbiF is CLK-1 specific.

Any compound that inhibits both CLK-1 and UbiF, but that is not toxic to JF496 (by virtue of the "toxicity" assay) is likely targeting a mechanism common to both enzymes.

9 MAMMALIAN CELL SCREENING ASSAY

Compounds identified as inhibitors of CLK-1 in bacterial screens are further screened for their ability to inhibit endogenous CLK-1 in mammalian cell lines. This exemplary assay uses HPLC to measure the levels of the chosen quinone (Q9 in mouse, Q10 in human) under control and test conditions, and where it is detectable, also permits analysis of the Q precursor, DMQ, in the same sample.

Briefly, following lysis, cellular quinones are extracted in hexane-ethanol (twice), and samples are run on HPLC to separate the quinones, which include an internal quinone standard (Q6). The area under the peak is estimated and in correlation with the efficiency of extraction of Q6, the concentration of Q9/Q10 is determined as ng/ug protein.

9.1 Materials

Ubiquinone-6 (C9504), ubiquinone-9 (C9888) and ubiquinone 10 (C9538) were provided by Sigma. Ethanol (HPLC grade, A995-4) was provided by Fisher. Methanol (HPLC grade, 270474) and hexane (HPLC grade, 27050-4) were purchased from Sigma. All cell culture medium was obtained from Invitrogen (DMEM 11995-065, FBS 10082-147, Penicillin-Streptomycin 15140-122, Trypsin-EDTA 25300-062, Non-essential amino acid solution 11140-050). Cells were cultured as described in protocols supplied by ATCC. The amount of cells needed to obtain a suitable quinone profile was determined empirically for each cell line.

The stock solutions of the quinone standards were prepared by dissolving pure ubiquinones in ethanol (HPLC grade) at concentration of 50 ug/ml. These solutions were kept at −80° C. The working standard solutions were prepared by diluting the stock solutions to give appropriate final concentration.

9.2 Assay Method

The extraction of quinone from cells was performed by the following procedure. Confluent cell dishes were rinsed with PBS, then 5 ml of PBS were added to each dish and cells scraped into the buffer. After centrifugation at 1000 rpm for 5min, the PBS was removed by aspiration. 500 ul of PBS and 500 ul of 3% SDS were added to resuspend the cell pellets, and Q6 standard was then added. 2 ml of ethanol was added and vortexed at full speed for 20 seconds. Hexane (2 ml) was added to this, and vortexed at full speed for 2 min. Samples were centrifuged at 2200 rpm for 5 min at 4° C., and the upper layer was decanted into eppendorf tubes. This extraction was repeated once. Speed-Vacuum (30 min at medium speed) was used to evaporate hexane. Finally the quinone extract was resupended in the mobile phase (Methanol/Ethanol 70:30) before running on HPLC.

The HPLC system consisted of 126 solvent module pump (Beckman), a model 7255i injector (Beckman), an autosampler (Model 508, Beckman), and a UV detector (set at 275 nm). The column was packed with $C_{18}$, and the flow rate was 1.8 ml/min. An isocratic method using a mobile phase consisting of 70% methanol and 30% ethanol, and a gradient method where the composition of ethanol increases from 30% to 70% over 5 min after 6 min, were both tested. This procedure was performed at room temperature. Both systems separated well the various quinones, with a shorter run time being achieved with the gradient system.

Those skilled in the art will recognize, or be able to ascertain using no more than routine experimentation, many equivalents to the specific embodiments of the invention described herein. Such equivalents are intended to be encompassed by the following claims.

All publications, patents and patent applications mentioned in this specification are herein incorporated by reference into the specification to the same extent as if each individual publication, patent or patent application was specifically and individually indicated to be incorporated herein by reference.

What is claimed is:

1. A prokaryotic test cell which is deficient in endogenous DMQ hydroxylation activity, and which comprises a target DMQ hydroxylase from a vertebrate animal.

2. The prokaryotic test cell of claim 1, which comprises a mutation or a disruption in a gene that encodes an endogenous DMQ hydroxylase, wherein said endogenous DMQ hydroxylase comprises an amino acid sequence that shares at least 50% sequence identity with SEQ ID NO: 4.

3. The prokaryotic test cell of claim 2, wherein said test cell is a *Escherichia coli* cell and said gene that comprises the mutation comprises the nucleic acid sequence of SEQ ID NO: 1.

4. The prokaryotic test cell of claim 1, wherein the transcription and/or translation of a gene that encodes an endogenous DMQ hydroxylase is inhibited, said endogenous DMQ hydroxylase comprising an amino acid sequence that shares at least 50% sequence identity with SEQ ID NO: 4.

5. The prokaryotic test cell of claim 1, which is a *Escherichia coli* cell.

6. The prokaryotic test cell of claim 1, which comprises a polynucleotide encoding a vertebrate CLK-1 protein, said polynucleotide being operably linked to a prokaryotic expression regulatory region.

7. The prokaryotic test cell of claim 1, wherein said target DMQ hydroxylase is a vertebrate CLK-1 protein comprising an amino acid sequence that shares at least 50% sequence identity with SEQ ID NO: 13 or SEQ ID NO: 15.

8. The prokaryotic test cell of claim 1, wherein said target DMQ hydroxylase is mouse CLK-1 protein or human CLK-1 protein.

9. The prokaryotic test cell of claim 1, which is JF496-mclk-1 or JF496-hclk-1.

10. A kit comprising the prokaryotic test cell of claim 1, 3, 4, 5, 3, 6, 7, 8, or 9 for screening for a test compound that modulates the activity of the target DMQ hydroxylase.

11. A method of screening for a test compound that modulates the activity of a target DMQ hydroxylase, comprising:
(a) contacting a prokaryotic test cell with a test compound for a time sufficient to allow said test compound to modulate DMQ hydroxylase activity in said test cell, wherein said test cell is deficient in endogenous DMQ hydroxylase activity and comprises a target DMQ hydroxylase from a vertebrate animal; and
(b) detecting a change in DMQ hydroxylase activity, wherein an increase or decrease in DMQ hydroxylase activity in the test cell contacted with the test compound relative to the DMQ hydroxylase activity in a test cell not contacted with the test compound, indicates that the test compound modulates the activity of said target DMQ hydroxylase.

12. The method of claim 11, wherein said test cell is a *Escherichia coli* cell.

13. The method of claim 11, wherein said target DMQ hydroxylase is a vertebrate CLK-1 protein comprising an amino acid sequence that shares at least 50% sequence identity with SEQ ID NO: 13 or SEQ ID NO: 15 test cell is a eukaryotic test cell.

14. The method of claim 11 or 12 wherein said detecting comprises determining the levels of one or more quinones in said test cell.

15. The method of claim 14, wherein said quinones are any of $DMQ_9$, $DMQ_{10}$, $Q_9$, and/or $Q_{10}$.

16. A method of screening for a test compound that inhibits the activity of a target DMQ hydroxylase, comprising:
(a) contacting prokaryotic test cells with a test compound for a time sufficient to allow the test compound to modulate DMQ hydroxylase activity in said test cells, wherein said test cells are deficient in endogenous DMQ hydroxylase activity and comprise a target DMQ hydroxylase from a vertebrate animal; and
(b) determining the growth rate of said test cells under selective condition, wherein a decrease in growth rate of said test cells relative to test cells under the same selective condition and not contacted with said test compound, indicates that said test compound inhibits the activity of said target DMQ hydroxylase.

17. A method of screening for a test compound that enhances the activity of a target DMQ hydroxylase, comprising:
(a) contacting prokaryotic test cells with a test compound for a time sufficient to allow the test compound to modulate DMQ hydroxylase activity in said test cells, wherein said test cells are deficient in endogenous DMQ hydroxylase activity and comprise a target DMQ hydroxylase from a vertebrate animal; and
(b) determining the growth rate of said test cells under selective condition, wherein an increase in growth rate of said test cells relative to test cells under the same selective condition and not contacted with said test compound, indicates that said test compound enhances the activity of said target DMQ hydroxylase.

18. The method of claim 16 or 17, wherein said test cell is an *Escherichia coli* cell.

19. The method of claim 16 or 17, wherein said test cell is a *Escherichia coli* cell comprising the nucleic acid sequence of SEQ ID NO: 1.

20. The method of claim 16 or 17, wherein said target DMQ hydroxylase is a vertebrate CLK-1 protein comprising an amino acid sequence that shares at least 50% sequence identity with SEQ ID NO: 13 or SEQ ID NO: 15.

21. The method of claim 16 or 17, wherein said target DMQ hydroxylase is mouse CLK-1 protein or human CLK-1 protein.

22. The method of claim 16 or 17, wherein said test cell is a JF496-mclk-1 or JF496-hclk-1.

23. The method of claim 16 or 17, wherein said selective condition comprises culturing said test cells in a minimal medium that comprises succinate or glucose.

24. The method of claim 16 or 17, wherein said selective condition comprises culturing said test cells in the presence of hydrogen peroxide or copper sulfate.

25. The method of claim 16 or 17, further comprising providing a culture of said test cells at an optical density at 600 nm of about 0.03 prior to step (a), wherein said test cells are JF496-hclk-1 or JF496-mclk-1 and said selective condition comprises culturing in M9-LB medium comprising 0.5% glucose and 1 mM hydrogen peroxide.

26. The method of claim 16 or 17, further comprising testing said test compound for toxicity.

27. The method of claim 16 or 17, wherein said selective condition comprises culturing said test cells in a minimal medium that comprises only a single source of carbon.

28. The method of claim 16 or 17, wherein said selective condition comprises culturing said test cells in the presence of oxidative stress.

* * * * *

UNITED STATES PATENT AND TRADEMARK OFFICE
CERTIFICATE OF CORRECTION

PATENT NO. : 7,132,274 B2
APPLICATION NO. : 10/841316
DATED : November 7, 2006
INVENTOR(S) : Hekimi et al.

It is certified that error appears in the above-identified patent and that said Letters Patent is hereby corrected as shown below:

Col. 65 line 54 in claim 10, the phrase "3, 4, 5, 3, 6, 7, 8 or 9" should read --2, 3, 4, 5, 6, 7, 8, or 9--;

Col. 66 lines 28-29 in claim 13, the phrase "test cell is a eukayotic test cell" should be deleted;

Col. 66 line 30 in claim 14, the phrase "claim 11 or 12" should read --claim 11, 12 or 13--.

Signed and Sealed this

Eighteenth Day of March, 2008

JON W. DUDAS
*Director of the United States Patent and Trademark Office*